(12) United States Patent
Webster et al.

(10) Patent No.: US 6,927,054 B2
(45) Date of Patent: Aug. 9, 2005

(54) ISOLATED HUMAN PROTEASE PROTEINS, NUCLEIC ACID MOLECULES ENCODING HUMAN PROTEASE PROTEINS, AND USES THEREOF

(75) Inventors: Marion Webster, San Francisco, CA (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 187 days.

(21) Appl. No.: 10/060,333

(22) Filed: Feb. 1, 2002

(65) Prior Publication Data

US 2002/0115186 A1 Aug. 22, 2002

Related U.S. Application Data

(62) Division of application No. 09/734,675, filed on Dec. 13, 2000, now Pat. No. 6,365,391.
(60) Provisional application No. 60/235,557, filed on Sep. 27, 2000.
(51) Int. Cl.$^7$ .................................................. C12N 9/50
(52) U.S. Cl. ....................... 435/219; 435/183; 435/212; 435/252.3; 435/320.1; 536/23.2
(58) Field of Search .................................. 435/183, 212, 435/219, 252.3, 320.1; 536/23.2

(56) References Cited

PUBLICATIONS

Yamaoka et al. Accession O60235. Oct. 16, 2001.*
Mariotti et al. Accession Q6JE90, Jul. 5, 2004.*
International Search Report, Aug. 22, 2002, PCT/US01/29960.
WO 00 50061 A (Univ Ohio State RES Found; Lang JAS C (US)) Aug. 31, 2000 figure 1.

Database EMBL Online! Oct. 28, 1999 Lang and Schuller: "Homo sapiens serine protease DESC1 (DESC1) mRNA, complete cds" retrieved from Database accession No. AF064819 XP002208302 abstrcact.

The Sanger Center (UK) and the Washington University Genome Sequencing Center (USA): "Toward a complete human genome sequence" Genome Research, vol. 8, No. 11, Nov. 1998 pp. 1097–1108.

XP002208301 ISSN: 1088–9051 the whole document & Database EMBL Online! Mar. 16, 2000 Sulston and Waterson: "Homo sapiens BAC clone RP11–16P17 from 4, complete sequence" retrieved from EMBL Database accession No. AC096653 ZP002208303 abstract.

WO 01 36645 A (Burgess Catherine ;Quinn Kerry E (US); Rastelli Luca (US); Vernet) May 25, 2001 SEQ ID NO:11.

* cited by examiner

*Primary Examiner*—Ponnathapu Achutamurthy
*Assistant Examiner*—Christian L. Fronda
(74) *Attorney, Agent, or Firm*—Celera Genomics; Lin Sun-Hoffman

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

4 Claims, 43 Drawing Sheets

```
  1 CGCCCTTATG CTGAAGCCAT GGATGATTGC CGTTCTCATT GTGTTGTCCC
 51 TGACAGTGGT GGCAGTGACC ATAGGTCTCC TGGTTCACTT CCTAGTATTT
101 GACCAAAAAA AGGAGTACTA TCATGGCTCC TTTAAAATTT TAGATCCACA
151 AATCAATTTC AATTTCGGAC AAAGCAACAC ATATCAACTT AAGGACTTAC
201 GAGAGACGAC CGAAAATTTG GTGGATGAGA TATTTATAGA TTCAGCCTGG
251 AAGAAAAATT ATATCAAGAA CCAAGTAGTC AGACTGACTC CAGAGGAAGA
301 TGGTGTGAAA GTAGATGTCA TTATGGTGTT CCAGTTCCCC TCTACTGAAC
351 AAAGGGCAGT AAGAGAGAAG AAAATCCAAA GCATCTTAAA TCAGAAGATA
401 AGGAATTTAA GAGCCTTGCC AATAAATGCC TCATCAGTTC AAGTTAATGC
451 AATGAGCTCA TCAACAGGGG AGTTAACTGT CCAAGCAAGT TGTGGTAAAC
501 GAGTTGTTCC ATTAAACGTC AACAGAATAG CATCTGGAGT CATTGCACCC
551 AAGGCGGCCT GGCCTTGGCA AGCTTCCCTT CAGTATGATA ACATCCATCA
601 GTGTGGGGCC ACCTTGATTA GTAACACATG GCTTGTCACT GCAGCACACT
651 GCTTCCAGAA GTATAAAAAT CCACATCAAT GGACTGTTAG TTTTGGAACA
701 AAAATCAACC CTCCCTTAAT GAAAAGAAAT GTCAGAAGAT TTATTATCCA
751 TGAGAAGTAC CGCTCTGCAG CAAGAGAGTA CGACATTGCT GTTGTGCAGG
801 TCTCTTCCAG AGTCACCTTT TCGGATGACA TACGCCGGAT TTGTTTGCCA
851 GAAGCCTCTG CATCCTTCCA ACCAAATTTG ACTGTCCACA TCACAGGATT
901 TGGAGCACTT TACTATGGTG GGGAATCCCA AAATGATCTC CGAGAAGCCA
951 GAGTGAAAAT CATAAGTGAC GATGTCTGCA AGCAACCACA GGTGTATGGC
1001 AATGATATAA AACCTGGAAT GTTCTGTGCC GGATATATGG AAGGAATTTA
1051 TGATGCCTGC AGGGGTGATT CTGGGGGACC TTTAGTCACA AGGGATCTGA
1101 AAGATACGTG GTATCTCATT GGAATTGTAA GCTGGGGAGA TAACTGTGGT
1151 CAAAAGGACA AGCCTGGAGT CTACACACAA GTGACTTATT ACCGAAACTG
1201 GATTGCTTCA AAAACAGGCA TCTAA (SEQ ID NO:1)
```

FEATURES:
5'UTR:       1-7
Start Codon: 8
Stop Codon:  1223
3'UTR:       1226

Homologous proteins:

|  | Score | E |
|---|---|---|
| gi\|7661558\|ref\|NP_054777.1\| DESC1 protein [Homo sapiens] >gi\|61... | 371 | e-102 |
| gi\|4758508\|ref\|NP_004253.1\| airway trypsin-like protease [Homo ... | 349 | 3e-95 |
| gi\|6467958\|gb\|AAF13253.1\|AF198087_1 (AF198087) adrenal secretor... | 277 | 1e-73 |

BLAST to dbEST:

|  | Score | E |
|---|---|---|
| gi\|1679749 /dataset=dbest /taxon=9606 ... | 190 | 3e-46 |

EXPRESSION INFORMATION FOR MODULATORY USE:
library source:
Expression information from BLAST dbEST hit:
Primary cancers

FIGURE 1A

Expression information from PCR-based tissue screening panels:
Human Testis
Human placenta
Human fetal lung
Human fetal kidney
Human fetal heart
Human fetal brain
Human bone marrow

FIGURE 1B

```
  1 MLKPWMIAVL IVLSLTVVAV TIGLLVHFLV FDQKKEYYHG SFKILDPQIN
 51 FNFGQSNTYQ LKDLRETTEN LVDEIFIDSA WKKNYIKNQV VRLTPEEDGV
101 KVDVIMVFQF PSTEQRAVRE KKIQSILNQK IRNLRALPIN ASSVQVNAMS
151 SSTGELTVQA SCGKRVVPLN VNRIASGVIA PKAAWPWQAS LQYDNIHQCG
201 ATLISNTWLV TAAHCFQKYK NPHQWTVSFG TKINPPLMKR NVRRFIIHEK
251 YRSAAREYDI AVVQVSSRVT FSDDIRRICL PEASASFQPN LTVHITGFGA
301 LYYGGESQND LREARVKIIS DDVCKQPQVY GNDIKPGMFC AGYMEGIYDA
351 CRGDSGGPLV TRDLKDTWYL IGIVSWGDNC GQKDKPGVYT QVTYYRNWIA
401 SKTGI (SEQ ID NO:2)
```

FEATURES:
Functional domains and key regions:
Prosite results:
[1] PDOC00001 PS00001 ASN_GLYCOSYLATION
N-glycosylation site Number of matches: 2
    1    140-143 NASS
    2    290-293 NLTV

[2] PDOC00005 PS00005 PKC_PHOSPHO_SITE
Protein kinase C phosphorylation site

Number of matches: 2
    1    41-43 SFK
    2    266-268 SSR

[3] PDOC00006 PS00006 CK2_PHOSPHO_SITE
Casein kinase II phosphorylation site

Number of matches: 5
    1    94-97 TPEE
    2    152-155 STGE
    3    270-273 TFSD
    4    307-310 SQND
    5    375-378 SWGD

[4] PDOC00007 PS00007 TYR_PHOSPHO_SITE
Tyrosine kinase phosphorylation site 362-369 RDLKDTWY

FIGURE 2A

[5] PDOC00008 PS00008 MYRISTYL
N-myristoylation site

Number of matches: 3
    1      54-59 GQSNTY
    2     337-342 GMFCAG
    3     346-351 GIYDAC

[6] PDOC00009 PS00009 AMIDATION
Amidation site 162-165 CGKR

[7] PDOC00016 PS00016 RGD
Cell attachment sequence 352-354 RGD

[8] PDOC00124 PS00134 TRYPSIN_HIS
Serine proteases, trypsin family, histidine active site 210-215 VTAAHC

[9] PDOC00124 PS00135 TRYPSIN_SER
Serine proteases, trypsin family, serine active site 349-360 DACRGDSGGPLV Membrane spanning structure and domains:

| Helix | Begin | End | Score | Certainty |
|---|---|---|---|---|
| 1 | 11 | 31 | 2.281 | Certain |
| 2 | 203 | 223 | 1.014 | Certain |
| 3 | 291 | 311 | 0.791 | Putative |

BLAST Alignment to Top Hit:
Alignment to top blast hit:
>gi|7661558|ref|NP_054777.1| DESC1 protein [Homo sapiens]
    >gi|6137097|gb|AAF04328.1|AF064819_1 (AF064819) serine
    protease DESC1 [Homo sapiens]
    Length = 422

Score = 371 bits (943), Expect = e-102
Identities = 176/403 (43%), Positives = 267/403 (65%), Gaps = 4/403 (0%)
Frame = +2

FIGURE 2B

```
Query:    14  KPWMIAVLIVLSLTVVAVTIGLLVHFLVFDQKKEY-YHGSFKILDPQINFNFGQSNTYQL  190
              +PW+I ++I +SL V+AV IGL VH++ ++QKK Y Y+ +        ++   FG+  +
Sbjct:    16  EPWVIGLVIFISLIVLAVCIGLTVHYVRYNQKKTYNYYSTLSFTTDKLYAEFGREASNNF  75

Query:   191  KDLRETTENLVDEIFIDSAWKKNYIKNQVVRLTPEEDGVKVDVIMVFQFPSTEQRAVREK  370
              ++ +   E++V    F  S  ++ ++K+QV++ + ++ GV    ++++ +F STE     +K
Sbjct:    76  TEMSQRLESMVKNAFYKSPLREEFVKSQVIKFSQQKHGVLAHMLLICRFHSTEDPETVDK  135

Query:   371  KIQSILNQKIRNLRALP-INASSVQVNAMSSSTGELTVQASCG-KRVVPLNVN-RIASGV  541
              +Q +L++K+++   P ++   SV++   ++ +  +   +     CG +R   L   + RI    G
Sbjct:   136  IVQLVLHEKLQDAVGPPKVDPHSVKIKKINKTETDSYLNHCCGTRRSKTLGQSLRIVGGT  195

Query:   542  IAPKAAWPWQASLQYDNIHQCGATLISNTWLVTAAHCFQKYKNPHQWTVSFGTKINPPLM  721
                +  WPWQASLQ+D  H+CGATLI++ TWLV+AAHCF  YKNP +WT SFG  I P  M
Sbjct:   196  EVEEGEWPWQASLQWDGSHRCGATLINATWLVSAAHCFTTYKNPARWTASFGVTIKPSKM  255

Query:   722  KRNVRRFIIHEKYRSAAREYDIAVVQVSSRVTFSDDIRRICLPEASASFQPNLTVHITGF  901
              KR +RR I+HEKY+   +  +YDI++   ++SS V  +++ +  R+CLP+AS    FQP     +   +TGF
Sbjct:   256  KRGLRRIIVHEKYKHPSHDYDISLAELSSPVPYTNAVHRVCLPDASYEFQPGDVMFVTGF  315

Query:   902  GALYYGGESQNDLREARVKIISDDVCKQPQVYGNDIKPGMFCAGYMEGIYDACRGDSGGP  1081
              GAL     G SQN LR+A+V +I      C +PQ Y +  I P M CAG +EG  DAC+GDSGGP
Sbjct:   316  GALKNDGYSQNHLRQAQVTLIDATTCNEPQAYNDAITPRMLCAGSLEGKTDACQGDSGGP  375

Query:  1082  LVTRDLKDTWYLIGIVSWGDNCGQKDKPGVYTQVTYYRNWIASKTGI  1222
              LV+  D +D WYL GIVSWGD C +  +KPGVYT+VT  R+WI SKTGI
Sbjct:   376  LVSSDARDIWYLAGIVSWGDECAKPNKPGVYTRVTALRDWITSKTGI  422  (SEQ ID NO:4)
```

Hmmer search results (Pfam):
Scores for sequence family classification (score includes all domains):

| Model | Description | Score | E-value | N |
|---|---|---|---|---|
| PF00089 | Trypsin | 274.8 | 1.9e-86 | 1 |

Parsed for domains:

| Model | Domain | seq-f | seq-t | hmm-f | hmm-t | score | E-value |
|---|---|---|---|---|---|---|---|
| PF00089 | 1/1 | 174 | 399 .. | 1 | 259 [] | 274.8 | 1.9e-86 |

FIGURE 2C

```
   1 TTATATTCAT AAAAGTAGGC AGTAAGTTGA AGATTTATTC ATATAGGATT
  51 TAGTAGCTGC AGCTTTAACC TGTGGCTTCT GTAGCTTTTG TAATCTGGCA
 101 GTGCGCATCT GCTATATTAT CTAAATGTTT CCTCAAAAGG AGAAACACTC
 151 TAACAACTTA TCACCCTAGT CTGCTGGCCA CCATTTTCCC TCAGATGCTC
 201 ACAGCTTCTT CCGTGGGATT TGAAGATATG ACTTCCATGA CACTTGATCA
 251 GTATGTCAAT GGGTATTGAA CCACTCTTCA GCTCTGATCC CACGGTTCAG
 301 TTCCTTTCAG TGTGACTATG TGTCTTGGTG GTGGGAGATG TGATTCTTTT
 351 ATCTACTTTC TCCATTTATC TTACTCAGAG GAACTGTGCT CTAATAGGGA
 401 AATAGATTGA AAGCTTATAA ATTTCCTTGA GTTTAACTT TTCTCCTTTG
 451 GTCTTTTTTT CTTTTCAAAT GACTTGAAGA CACATTGATA AGATTCTATG
 501 AGAAAATGAA GAGTTGAACA AATTGAATAT GTATGAGTGA ATGAATAGAT
 551 TAATACATAA ATGATAAATT TATTAAATAA TTTGAACGAA ATCAATCGAG
 601 AGGCACCGAG AATAAATTTG TGTCCTAGAA GTAAGAAGAC CTGAGTTTGA
 651 GATAACTAGT AGTTCTATTA TACTGGAGAA ATTACTTAAT CATCACTGGA
 701 CTTCATTTTT CTCATATGGA AAGTAATTCA ATCACACTAA ACAATCTTTA
 751 AGGTCTCCTT CACTTATAAA TGTATGTTTT AAGCCATTTA GGAGGTTAAA
 801 TAATGTCATG TCCCATGGGA CTTCTGTTTG TTGTTCTATT CAAGCATGTT
 851 AGCTTGTTTC TATCACAGGA CCTGCTGCCT TTCCGCAGCC AGTTCTCTAG
 901 ATTATTTTTA ATCAGTCGGT GCACACATGG TCAATATTTA CTCAATAGAA
 951 TTCAGGTTTC CCAAATTCCA TGAGGATTCT TGATTAATTT TATTACTTAT
1001 GCCAAAACTA TTATCTTCTT AACTATTTTA GGTCCAAACA GTTTTAACTT
1051 TTATCCTGGC ATTTATATAT AAAAAACTTT TGTAAGACCG GGTGCAGTGG
1101 CTCATGCCTG TAATCCCAGC ACTTTGGGAG GCCGAGGTGG GTGGATCACC
1151 AGGTCAGGAG ATGGAGACCA TCCTGGCTAA CACCATGAAA CCCTGTTTCT
1201 ACTAAAAATA CAAAAAATTA GCCGGGCGTG GTGGTGGACG CCTTTAGTCC
1251 CAGCTATTCA GGAGGCTGAG GCAGGAGAAT GGCGTGAACC TGGGAGGCAG
1301 AGCTTGCAGT GAGCAGAGAT CACACCACTG CACTCCAGCC TGGCAGCCTG
1351 GATGACACAG CGAGACTCCG TCTCAAAAAA AAAAAAAAAA AAAAGAAAAA
1401 AACTGTTTTA TAGTCAAAAG AAAAACTTTC TATAAATCAA CCAATCCTGT
1451 GAAGAAAATA TGAAAATATAT CCTCTGTTTC CAAAAAAATT TAGGCTATCA
1501 ATATATACAC ATAAAGAGAT AAACTCTGAT AAATTGGATA AATAAAATTC
1551 ACTATAATAG CAAGTTTTAG AGAACAAGCA CGGGAGTTAG TCGACCTGGG
1601 CCCTTAAACA GATATCCTCT CTCTCATCCT GTGTTATTTC CTGTGTAATG
1651 TTGGTATCAT TCCTGCCTGA CTCTCATAGA TTTATATGAT TCCTACTCTG
1701 TCCAGGTGCC TTATTGGGTC TTAGCGGTAA AAAGATGAAC AAGGCTAATG
1751 CAGCCCATTG AGAAGCTATC TGTAAGTGAA CATACATGCA AACTAATACT
1801 TGATTCAATG TGAGAAGCAC TGTTGCTGAT CATAGGTGCC AGAAGAACAG
1851 CAAAGAGTTA TTTTTTCCTC CAAAATTGTG GAAAATTTT TATCCCCGGT
1901 GTGATGCAAT ATAAAATACA CAGCACCACC TTTGAAGTAT TCTTGCCAAA
1951 TGAATTTAAC CAAAATCTAA TCAAGACTTC AGAGCTAAAG AAAATCTAAA
2001 GGTAATCCAA TTTATAGGAA ATGAGGGATA TAAAAGAACA AGTTAAATAA
2051 TACCACAGGA AAGCATTCAG ACAAGTCCAG AAAGTAAGAT ATTCTAAAGG
2101 ATGTTTAGCT TGATCTCTTC AACAGTCAAT GTCATTAAAA ACTAAAAAAG
2151 AAGCAGGACT CTTTTAGATT AAAAGAGATT AAAAAGGCAT AACAAACAAG
2201 TGCACTGCAT GGTCCTCGAT TATGTCTTGG CTTTTACAAA TCATGTGTAA
2251 TTATAATGAA ACCATGGAGG GAACTTGAAG ATGGACTGGG TATTAGATGA
```

FIGURE 3-1

```
2301 TATGGCAGAA ATATCATTAA TTTTTTAGGA GTGTTAAGAG TATCATGGTT
2351 ATGTTGGATA TATCCTAATT GTCTATAATA ATGATTTGGT AAAAAGTCAC
2401 GATGTTTTAT TTCACATTAA AATATAGCAG CAGAAAAAAT AAATGAGCCA
2451 AATACAGTAA AATTTTCAAC AATTGATATA ATAATGTGAT ATATATATGG
2501 ATGTTCAATT ATACTATTCT TAGTAATTTT TTATGTCTGA ACATTTTCAT
2551 AATACTTAAA AATAAAAGAT AAAAGATAAA AATAAATGAG ATAATAGATT
2601 TAAAATCACT TTGTAAACTC TAAAAGGATA GACAGATAAA AGAGATAACA
2651 AAGTGCTGGA GAAAGGAGGA ATGGTCCCTT TTCAAGCATG TATGCCACCT
2701 TGGACCATGC TGCTAAGAGA AACCATTCCT GACCACCACA AAGAGGCCAC
2751 CAAATGCCTC TAAAATAGAA AGCAGGAGCA ACATTAGGAT TCCCAGATCC
2801 TGATATTTTT TTTTTAACAC ATCTTCTCAG ACCAAGATGA CATTGAACAA
2851 AATTAAAGAC CTTTTTGCAG GGAAAGGTAG GCTACAGCAA CTTGAACTTG
2901 TCTAAGGAGA GCTGGAAAAC CTGCAAGCAT TGCTATCTGA GAGTAACCAG
2951 TGGGCCCTTC CTTTTCTCAG GACAGTGGGA TTTGGCACCC GAAGCAGAAA
3001 TGCTGAAGCC ATGGATGATT GCCGTTCTCA TTGTGTTGTC CCTGACAGTG
3051 GTGGCAGTGA CCATAGGTCT CCTGGTTCAC TTCCTAGTAT TTGGTAGGTA
3101 AAATTAAAGA TTTCACTCTA TTTGATTTTA TTTTTCTGCA AAGCTCCATT
3151 TACATATATG TAAATGTAAC TTCATCTAAA AAATTGCACA TTTACCTTCA
3201 AATTTCCACA GAGTATATTT AACTGTTTCA GTCATTTCAT CAACAAACAA
3251 GTACTAAATT CTTATTATAT GTGAGTACTT TTCTGGATAT TCAAGATACA
3301 GCTTTAAGCA AAGTAGACAG ATTTCTAATT TCCTTAGAGC TCTCAACCCA
3351 GAATTCTTTT GAGAATCTAC ACAAAAAGAT CAAAAATTGT AATTGTCTGA
3401 AACTTACTAG TAATTATAAT AAACAACTCA TCACTTATTA TATATTAAAA
3451 TGAAAAGCTA TGATAAATTA GTTATTAAAA TTGGCTCTTT TACTCATGAA
3501 CCATCATTTT CTGTCCAACA TTTCTAAGGC AAAAGAAAAA CACTTGTCTA
3551 ATAAAATAAG GAATTTCAAA ATGATTGAAA ACCTATACGT ATGACACAAT
3601 ATTATCATTT ATTTTTAGAG AAAAAAAATT TTACTCTTTC CAAAACAATA
3651 TTCAGGGATT ATATTTTTAT CAACTAATAT ATTTGTAATT ACACAAATAA
3701 TGCACTTCAA GATTCTCTTT TTACATTCAG TCTCTTTCTG GGGAGAATGC
3751 AAGCCATTTA CATTTTTTCA CAAATCTCTA CAATGTGACT CTCACATGGA
3801 TGTATGTGAT AAAACAAATA ACTCAGGCTG CTCACTTTAA CGCTCTTATC
3851 TGCTGTCACC TTCACAGAGT CAATGGGGGA GCAAAGACTC TACTTGGAGC
3901 CTTAAAGGGC TTAAGATCAT AGTCCTAGGC CTTATATGAT AACCCCAGCT
3951 GTAGTTTATA CCATTGGCAA AAGATTCTCA GGTCACTTTA TTTGGTTGCA
4001 TAAAAGTCTC TTTACAATGA GAGTAAGGTT TGTTAACAGT ATGGATTATA
4051 TGGGTAAGTA ATCAGGATGT CCAAAAATGT ATTACAAGGT CCAGAGATTT
4101 CCCACTTAAG ACATATGCCT TCCTGATATC CCTGTTTCTT TCCTTGGTTT
4151 GTAGTCTCGA AACCCACTCC CTCTTCCCTG AGCCAGGCTT CTCAAGGATT
4201 GAGGTTGTTT TGTATTTTTC CCATTCTCTA TCTTTAACTC TGTATCTTTC
4251 TTACTCCCTC TGGGCCTTAC TCCTCAGATT ACCAAATTCC TTAGGAGTCT
4301 CAACTGCTTT CCTTTCTTAC ATTTCCTAAT AGATTTATCC CTGTTTCATG
4351 CTCGTCTTGT CTTCAATCTC AGACAGCTCT TCTCTACACT TTCTTTTCAG
4401 GTTTTTCTTA GTGTGCCTGG CTCTCTTGTT AAAAATCAAA ATTCACAAGG
4451 ACATTCACTT ATCTCTACTT CCACTAGAGT GTATGATGGT ACACATTTCA
4501 ACTCAGCAAG GAGCAATGTA GCAATGAAAT GTTCAAGCTC TACAGCTAGA
4551 CTGGATTTAA AACTTGGACA GGCCACCTAC TAGTTACAGA ACAATTTACT
```

FIGURE 3-2

```
4601 TAATGCCTCT GTGCCTTAAT TTCCTTATCT GTAAAATGAA GGTGATACCA
4651 ATCTTAGAGA GCTGGTGTGG GGATTAAATG GGCTAATACA TAAAAAGTGC
4701 ACAGGACAGT GCCTGCCATA TTGTAGAAAC TCAATAAATG GCAGCTATTA
4751 TAATTGATAT AAAACATTAA CTGTTATTTT TTAAATAAAA CTCAATTATG
4801 AAGAGGCTCA GGGACATATT CAAGATTTAT ATTGGCCCCA TTGTAATTGA
4851 GTTCTGAAAT CTTTGTCCAA ACCATTTAGT TTCCTATTTT TCATTTCCAT
4901 TGCAGACCAA AAAAAGGAGT ACTATCATGG CTCCTTTAAA ATTTTAGATC
4951 CACAAATCAA TAACAATTTC GGACAAAGCA ACACATATCA ACTTAAGGAC
5001 TTACGAGAGA CGACCGAAAA TTTGGTGAGT CAGGTAAACT TCTTTTTATC
5051 ATAGAATAAT GCAAGTGGAA GGGATTTTGT GGATCATTTC TCCATTTCTA
5101 AAAACATGAT TTTCAGACCG CCAACATTAG AATCATCTTG CAGATTGCTA
5151 GGCCCCATCC CAGACCTGCT TAATCAGAGT ATGATGAGAT GGGTAGGTGG
5201 GGAGAGGAGA GTAAGGGAAT CTGCATGTCT AACAAATGGG TGATTCTAAT
5251 AAGCCTCTCT TTCTAACTCA GCTACCTTAT TTAAAGGTAA GAGAATTGAG
5301 GCCAAGATAT CCTAGCCCGT TTCTTCCCCA ATTCCACCAC GTTTCCCCTG
5351 TAGAAAAGCC TAATCATACC AAAACTAGTT TTTATAAGTC CACACACTTG
5401 TTTGTAAGAC CACATTTTAA GATTTGAGT ATTTTCAGAA TTTACGTTCA
5451 TCTTGTAAGT ATATTGATAA AGACAAAAAA CCAGACTTAT TTTGTAGTAA
5501 TCAAGTCAAA TGCTAATAAT TTTGTTAAAG CTAAAGTGCA AGACTGCTCC
5551 CAAAAAGAAA AAAAGCACAC TCAGTTGTAT AATCATTCCA CTCAGAATGC
5601 CCATGAACTC TCACTCAAAA ACTAGGTTCA AATTAATTTT TCTAACAAGG
5651 AAGCACAGAA GCAGAGACTT ATTTTAAAAA GAAAGAAATG ACAAATGTAT
5701 TGGTTTGTTT TAATCAAAGA ACCATTTTA AGACACTTTC TTTCCCAAAT
5751 CATCTACCAT TTTTTCCTGT CATCATTTGC TCTTTGTCCA TAGTATACCT
5801 AATGGCATCA TATTTACAAT AATATTGTAG AGTTTATAAT CTCTATTTTC
5851 AGTTAACATT AAATCATTCA CAATTTCTTA ATTTTGTGGT TTCATCTTTC
5901 CCAACCAATA ATTAATGTCT ACAGATTGAT ATAGATTCTG CATTCTTTCA
5951 CATGCAGAGC ATCTTATAAA AGAGCATTTG CAATCAGTTC TTAAGTTATG
6001 CTAGGATGAA CGGGGAGCCT GCACCAATAC ACCCAAATAC CTTCTCTACT
6051 CCTCCAGTCC TAAGTGACTC CACATAACCT CCTCGATGCA AAAAGAGAAA
6101 ACTCTTAACT TGCCTTAGTT AAAAAGATAA ACACACCTTT GAATGATGGA
6151 AAATGTTACA ATTTACTGGG AAATTTTGAA ATTTGTTTCA TTTATATTTT
6201 ATGGCCAACA TTACTGCTAC TGTTGTTGTT GTAAGTTAAC TAGGCAATTC
6251 TGTCTTTACT GAAGTAAACG GACAAGAATG CAATAGGTCT TAAAAGAAGT
6301 GAGAGAAATG CAGAGGTGCA TGTTGAACAG AAACTCTATT TAAAAGTGGA
6351 GTTTTAAGTT TCACCTAAGC ATGTGTTCCT TCAAAGGCTA AGGCTAAGTT
6401 AAGTAAGGAC ACATTATCAT CATGGGTACC TGCAAGGCCC TTCTCTGGTT
6451 GTCATTATTT ATTTATCCTC CTTTATCACC ATAGCATAAG CCCTTACCCT
6501 CCCCCCTTGC AGGAAATCAT TCTATGTTTC ATGTGGTATT CTTTTGTTTG
6551 TATTCATTCT TACAAAAATA TGTTTTGCTA TTTTGCGTAC ACTTGCTTTT
6601 AACTTACATT TTGTGTTATA AATCACTTTT GTTTCATCTC TTTTTACTGA
6651 GAACTTTTTA AAAGATATAT GTTACTAAAT ATACCTTTAG TTTATTGCTG
6701 TTAGCTGCTA ATTCATAGTG TGTATCTTCC ATATTTACCT GCCTGTCATG
6751 CCAAGAAATG CCACACTAAA CAGACTCCTA CTTACCCCCT TATAGACCTA
6801 TGCAAGTACT TCTGGAAGCA GAATTACTAG GTCATTGAAT GTACATATAC
6851 TTAACTTGAC CAATTGGTGC AGGTTTGCTC TTCAAAATGG CTGACTCAGT
```

FIGURE 3-3

```
6901 GTGCACGCCC ATCTACAATG CATGAGGATT TCTATGTCCC CACATCTAAC
6951 CAACACTTAG TGTCTTAGTA TGTTTAGGCT ACTACAACAA AAAATACCAT
7001 AGGCTGGGTA TCTTAAACAA CAAACAATTA TTTCTCATAG TTCTGGAGGC
7051 TGAAGATTCC AAGATGAAGA TGATCAAGGC TCTAGCAGAT GTCTGGTGAG
7101 AGCCTGCTTC CTGGTTCATA GAATACCATC TTGCTGTGTC CCTCATGGCA
7151 GAAGCCATAA GAGAACTTTC TTTTGTAAGG ACACTAATGA CTTTCATGAG
7201 AACTCCACCC TCATGACCTA ACTATCCTCC AAAGGCCCCA TCTCCTCTAT
7251 CATCGGTTTG GGAGTTAAGG TCTCAAAATA TAAATTTCAG GGGAACACAA
7301 ACATTCAGTC CACAGCACTT GGTATTATTT GGCTTTCTAA ATTTGCCACC
7351 CTAATATGTA TAAAGTAGTA TTTTATTTGT GATTTAATTT GCATGTTTCT
7401 AATTACTAAT GAGTTTGTGC ATTGTTACGT ATAATTATTA ACTTTTTGGA
7451 CTTTCATTTC TATAAATTGC CTGTACATAT TATTTGCCTA TTTTTCTGTT
7501 AAACTTGCTT TTTCACCTTA TTTGTATTGC TTTGCAGAAG TTCTTTACAT
7551 TTTCTGGATA TTGATAGTGT GTTGGTTGTG GACACTGCGC TTATCCATTC
7601 TGTCTTCTAC TAATATGGAC CGTGTTGTTC TTTATGAAAC CGAAATCTGT
7651 AACTGAAGTA ATCATTTTTT CACTGTTTTG CCTTATGATT GTATTTTGAA
7701 GCTTTTCTTT AAGAAGTCCT TCTTCCCTTC TAAGACATAA AAATATTTTA
7751 CTATGTTACT TATTAACCTT ATAGTTTTAT CTTTTACATT AGGTCTCCAA
7801 TACATGTGGA ATCCACCTTT GGATGTGTTA GGTAGATTCA GTTTTTTAAT
7851 TCATATAGTG AGCCAGTTTT TGAATATAAC TAGTTAAAAT ATCTTGGCTT
7901 TTCCTAATAT ATGGTATTAT TATTGAGTTC ATTGCATGCA TTTCTTGGCA
7951 CCTGGGTCTT GCAGAAAAGG AAACATGAAT CTGTCTCCTC AAATTGCTTC
8001 CAATCTTTTT GGAAAGATGT GAGTAACACA CATGGAATTG AATATCATGA
8051 CATGATATAA TTAAGGGCTA AATTACATGT TGAGGACAGT AAGTACAGAA
8101 AAACTTCAAA ACCAAACAAG GGTTCCCATG GTCAGAAAAG GCTTTATATT
8151 ATTTTACCTT TGTTTAAATG AGACAGGTGT TTTTCTCCTC CCATCCCGCA
8201 CCAGGTTAGC TTTAGAAGAA TTACAGGAAG AGTTTATGCC TCATCCTGAG
8251 CCACACCTGT TTGTTGTTGC TAAATCCCAA TGAATACAAC CAGATTCTTC
8301 TCTCTGTCCT ATATGGGTGC TAATTAGACA ACCAAGGAAG AACAGGTTGC
8351 ACGTCCTGTT CTTCCTCACA TTGGGCTTTA CTGATTTGAA TGCAAATTGA
8401 GATGCAAAAG TAAAAATGAG TTCATATTTA GATATTGCTA TAATCCGCCC
8451 CTGTTCCCTG AGATAGTGGA GCAGACATAT CTCATCTCTC ATATCATTCT
8501 TCAGAGAAGG GTCCATTAAT CAGACATTAC TGATGTCTGA TTACTGCCGG
8551 CTGGCCATCC TGCAGGTGGA GAAGCATGGC ATCCAGCAGA AACTGACAGC
8601 ATGCACTTTG AGGGAGGGAA GGATAAGCCA GGAATTTATG CTGAATAAGC
8651 TGCCTAAGTA TACATGTTCA ATAAGTTCTA GGGGAAGTCA CAAATACTTA
8701 TGAAAGGAGA AACATAACTA TGTGCAATTG AGCTTTATGT CTCTTCATGT
8751 GTTGCATGTT CAAAAAATGG TGGCATTAGC ATGATCCAAG GGTGGAGTTT
8801 TCAGCCATTT GATGTTCAAA GGTGAAGCAG AGGACACAAA ACCCTTACTA
8851 TGCATCCTCT GTGAGTCAGC CAAAACCAGT CTGGACTGCT AGCTAGATTA
8901 ACAAAGAAAA AAAGAGAAAG AAGATACAAA TAAGCACGAT CAGAAATGAT
8951 AGAGGTAACA TTACAACCAA TCCCACAGAA ATACAAAAGA TCGTCTGAGA
9001 CTCTTATGAA CACTTCTATG TAGATAAACT AGAAAATCTA GAGGAAATGG
9051 GTAAATTCCT GGAAAACAC AATCTTCCAA GATTGAATCA GAAAGAAATT
9101 GAAACCCTGA ACAGACCAAT ATTGAGTTCA TACTTAAATC AGTAATTTAA
9151 AAAACTTACC AGCCAAAAGG AAAAAAAAAG GCCCAAACTA GATGGATTCA
```

```
9201 CAGCCAAATT CTACCAGACG TACAAGAAAT AGCTAGGACC AATTCTAGTG
9251 AAACTATTCC AAAGAATTGA GAAGAGACTT CTTCTTAAAT CATTCTATGA
9301 AGTCAGCATT ACCCTAACGC CAAAACCTCA CAAAGACAGA ATGAAAAAG
9351 AAAATTACAG GCCAATATCC CTGATGAACA TAGATATAAA AATCCTCAAC
9401 CAAATACCAG CAAACCAAAT CCAGCAGCAC ATCAAAAAGT TAATTTTCCA
9451 AAATCAAGTA GGCTTTATTT CTGTGATGCA AGACTGGTTC AACATATGTA
9501 AATCAATAAA TGCGATTTAC CACATAAACC GAATTAAAAA CAAAAATCAT
9551 ACAATTAGCC AGGCATGGTG GCTCACACTT GTAATCCCAG CACTTTGGGA
9601 GACCATGGTG GGCAAATTAC CTGAGGTCAG AAGTTCGAGA CCAACCTGGC
9651 CAACATGGTG AAACCCCATC TGTATTAAAA ATACGAAAAT TAGCCGGGCA
9701 TGGTGGCAGG TGCCTGTAAT CCCAGCTACT CGGAGGGCTG AGGCAGGAGA
9751 ATCACTTGAA CCCAGGAGGC AGAGGTTGCA GTGAGCCGAG ATCGTGCCAT
9801 TGCACTCCAG CCTGGGTGAC AGAGCAAAAA TCCATCTCAA AAAAATTAAA
9851 AATTTAAGAA AATTAAAAATC ATACAATCAT CTCAATATAT GTAGAAAAAG
9901 CTTTTGATAA AATTAAACAT CCCTTCATAA TAAAAACACT TAGACTAGGC
9951 ATCGAAGAAA CATACTTCAA AATAATAAGA GCCATCTGTG ACAAACCCAC
10001 AGCCATCATC ACACTGAATG GGCAAAAGCT GGAGGCACTA TCCTTAAGAA
10051 CAGGGAAAAA GACAAGAATG TTCACTCTCA CTACTCCTAT TCAACATAGT
10101 ACTAGAAGTT CTAGAAAGAG CAATCGAGCA GGAGAAAGAA GGAAAATGCA
10151 TCCAAATACG AAAAGAGGAA GTCAAATTAT CTCTCTTTAC TGACAATATG
10201 ATTATATGCC TAGAAAACCC TAAAGACTTT ACAAAAAGTT TCCAAAACTG
10251 ATAAACAACT TCAGTAAAGT TTCAGGATAC AAAATCAATG TACAAAATTC
10301 AGTAGCATTT CTAAACAATA ATGTCCAAGC TGAGAACCAA ATCAAGAACA
10351 CAATCCCATT TTCAATAGCG ACACACACAC ACAAATGAAA TACCTAGGAA
10401 TACATCTAAC CAAGGAGGTA AAAGATCTCT ATAAGGAGAA TAAAAAAACA
10451 CTATTGAAAG AAATCGGAGA TGACACAAAT GAATGCAAAA ACATTCCATG
10501 CTCATGGATT GGAAGAATCA ATATTGTTAA AATGTCCCTA CTGCCCAGAG
10551 CAATCTACAG ATTCAATGCT ATTCCTATCA AACTACCAAC ATAATTTTCC
10601 ACACAAAGTT AGAAAAAGCT TTTGTAAATT TCATATGGTA CAAAAAAAAA
10651 AAGCCCCAAT AGCCAAAGGA CTCCTAATAA AAAAGAACAG AGCCAGAGGC
10701 CTCACATTAT CTGACTTCAA ACTATACTTT AAGGCTACAG TAATCAAAAC
10751 AGAATGGCAT TGGTCAAAAA CAGACATATA AACCAATAGA ACAGAATAGA
10801 GAACCCAGAA ATAAAGCCAC ACATCTACAG CCATCAGATA TTCAATAAAA
10851 TTAACAAAAA TAAGCAATGG GGAGAGAACT TTCTATTCAA TAAATGGTGC
10901 TGGAATAGCT AGCTAGTCAG AAGCAGAAAA ATGAAATTGG ACTCCTATCA
10951 CTAAATACAA AAACTAACTC AAGATGCAGT AAAGAATTAA ATGTAAGACC
11001 ACAAACAATT AATACAAGAA CCCTAGAAGA AAACCTAGGA AATACTGTTG
11051 TAGACATCAG TCTTGGCACA GAATTTAGGA CTAAGTCCTC AAAAGCAACT
11101 GCAACAAAAA CAAAAATTGA TAAGTTGGAC CTAATTAAAC TAAAGAACTT
11151 CTGCACAATA AAAGAAACTA TCAACAGAGT AAACAAACAA CCTACAGACT
11201 GGGAGAAAAT ATTTGCAAAC TATGCATCTG AAAAGGTCTA ATGTCCAGAA
11251 TCTGTAAAGA ACTTAAACAA CTCAACAAGC AAAAGAAACC AAGTAACGCC
11301 ATTAAAAAGT AGGCAAAGAA CATGAACAGA TGCTTCACAA AAGAAGACAT
11351 ACAACGCAGT CAAGAAACAT ATGAACAAAT GCTCCACATC ACTAATTATC
11401 CAAGTAATGC AAATCAAAAC TACAGTGAGA TAATATCTCA TACCAGTTAC
11451 AATGGCTATT ATTAAAGATT AAAAAAATAA CATGCTGATG AGACTGCGGA
```

FIGURE 3-5

```
11501 GGAAAGAGAA TGCTTAAATA CTGTTGGAAA CGTAAATGGG TTCAGCCACT
11551 GTGGAAAGCA GTTTGGAGAC TTCTCAAAGT ACTTAAAATG GAACTACTAT
11601 TCAACCTAGC AATCCTACTT ACTGGGTGTA TACCCAAAGG AGTATAAACT
11651 TTTTTCCCAG AAAGACAGCT GCACTCTCAC ATTAATTACC ACAGTATTCA
11701 CAATAGCAAA GATGTGGAAT CAACCTAGAT ATCCATCAAT GGTGGATTGG
11751 ACAAAGAAAC TGTGAGATAT ATATGTATAT ATATCTATAT ATACCATGGA
11801 ATACTATGTA GCCATAAAAA AGGATGAAAT CATGTCCTTT GCAGCAACAT
11851 GGATGTAACA CCACAAGGAA GGCACTTTTA TCTCCTCTTT ACAGGTAAGA
11901 GAACCAAGCT TCTGAAATTA AGGTCCATAG CTGGAAAATG ATGGAGGGGA
11951 GATTTGAAGT CATCTAGGCA ACTCCACACA TGTGCTCTTT CCACTAAATT
12001 GTTCTACTGT CAGGAAGGGA CTCAGCTAAG ACAGAAGATA AAATTATTAA
12051 AATCTAAATC AATTCTTCTC TCATTTCATT TTTTAAATCC ATGAAGATTA
12101 TAAATCCTCT ATGCTGTGCT AGCTAACTTT TTCTTGACAG ATACATTAGG
12151 TATACTTATT AGAGAAAAAT ATTCTCTTTC TCATTTCCCT GTATCAGTTT
12201 TTGGTGAGGA AGGCAAAGGT AGGAGGAACT GTAATAGAGA AAGATGAAGG
12251 AAGCTGATGG ATATATTGAC ATGTGTATGT ACATCTAGTG TGAACAATCT
12301 ATAGTTGGAA GAAAGGTGTG GATGGGTATG CTTTTTGAGG GAAGTTTTTG
12351 AGAAAAGAAG TAATATGAAC TATTTCTAAA TTTCCTGATA AAGTTGTAAA
12401 TACAGCATAG TCTTCACAGG AGAATCTATT TAGTTTATCA TCATCATTCA
12451 GCAAATACAG CATGATGTTA GGCACTATAA AAGGCTAAGA AAAATGATTC
12501 TCTCTCTCTC ATAAACTAAT CCAATTTAGA GATTTAGAAG ACAACAAATC
12551 TGGAGAGGAC ATGAACCTTC TAAATAATGA CCTTCCCTTG CTTTGGGTAT
12601 CCTGGTTTTA AATATTTTTA GTACAGCTTT AAATAGATCC AAATGAGATA
12651 TTTTCCTCTT TTACAAAAGC AATTCAAAGA TCTAGGTTTT TGTTGTACAC
12701 TGAGAATTAA TACTTTTTTC TTTAAAATCC TTAATTGCAA ATCTTTAAAT
12751 TCTATAAATA TTTTGCCTTG TGATCTCAGA AATATAAGCC AATTTGGGAT
12801 ATGGATATCT AAATATATTGC TACTTGTTAC ACGTGAGTAG TGACAGATGT
12851 CTGTCCATTT CTTTCTGACA TTCCACAAAG AAACACTGAA GAAGGACCAG
12901 TGCAATCAAA GAAATGACTG ATGGCATCAC AAAATATCAC ATCCCATTTG
12951 ATGATCTGAT TACCTTTTTG TTTAGGGTGA TCAGAAAGTC ACAGTTTCAT
13001 GGCACCCTCC ACACCCACAC ACCTTGTATG ACACTGGATC CAACTGCTTT
13051 CTCCAATAGA CACAGCACTT AAAGATGTGG CAGTTAGGCT TGACCCCAAG
13101 AAGGCCAAAA AGCCTTCTGT GAGCATCACT CAGTGCTCAG GTTGACTAAG
13151 CTCTATCCAG GCTTGAGAGA ATGGTTCATA GCTGACTTCT TGGATCCAAA
13201 AAAAAAAAAA AAACACCTAG AGTTTTATAC AGATATGATA CGAACTTAAA
13251 AGGACTGCAC TAAAAACTAC CAAGATTATG ATTCTTATTT TTGGAGAGTA
13301 AAGAAAATAG GCTGCCTTTG GAGAGGGGTG CAACAGTTTC TGATCCTCTT
13351 ACAAACTGCT TGCTGCCCAT CAGTGGGTAG GAGGTCTTAG TGAGAACCTA
13401 CCTGCATGCT CATCCTGAGG TAGGCACTGT GAAGGCGTTA ACAGGCTCTG
13451 AAGCTACATG GCCCTGGTTT CAGTGAACTC TGTGGTGTCA ACTTGGGCAA
13501 GTCACTTCCT CTTCTATGAA ACGTGAATAA TCATAGTACT CACCTTAGAG
13551 GGCTGATTTG AAAGCAAATG AGCTCAAACA CAATGACATC TGTGCTTGGT
13601 GCATATATGG CAGACAACAG TGATTCCCAC TATTATAATT ATTACAGTCT
13651 TACCAAGGAG GAGCTTTCCA CAAATAATCA ATTACCTAAA ATGTCCAAAA
13701 ACAGGAAAAA AAAATCTCTT CCGATAATTC ATGTGTAATT TTCTTTTTTC
13751 TCTAGGAGCA TTGATCTCAA CCTGATGTAA AGCAAGCACT TTAAAAAGTC
```

FIGURE 3-6

```
13801 TTATAAAATT TTCCTGGTAA ATGCAAAACT TTCTGATAAA TAAATTCTCA
13851 CCTTTTTATC AATTTGTTAA TTCAACAAAA ATATACTACA TACCAACAGC
13901 ATGCAAAGCA CTATGCTAGA TTTTATAGAC TATGAAAAGA TAAATTGCCA
13951 TCTCTATGCA TAAAGGGTTT GCCATTTAAT AAAAGAGACT ATATATTTGC
14001 ATAAATATAT AGTGAATATA TTGCATAAAT ATATAATATA TGTTTACATT
14051 AAAGAATAAA AGGTATAAGA GGGATAAGAA AAATTGAGAC AGAGGGAAGA
14101 CAGGTCAGTT TGAGATTAAC GAATATCCCC AAAGAAGGTA TTATCTGAGA
14151 TTGGCCTTGA AGGATAGTTG TGATTCAGGA ACACAGAACT TGCAGAATGA
14201 GAAGGTTGTT ACAGACCAAA GGAACAGCCT GAGAGGCGTG AGTATGCAGG
14251 AAAATGAGGG CCATGCCTGA AAGTACTGGT GGTGTTGAAG ATGGAGCCAG
14301 GCAAGTTGGT CACAGAGGGA GAGGACCTTG AATGTCTAAC ATTGTGGACA
14351 GAGGCTCAAA GGCTCAAATT CCCTATTTTT ACCTTGAGTT CAATCCTTGT
14401 GGCAATGAAA CCTCAGTGAA GCTTTATTTA AGGCTAAAAG TGTCTTTTAA
14451 AAATCCCTCT TATATAATAT CCTTTGCATG TTACTCTTGT TGTAATTAGG
14501 AGAAAGCAAT AGGATCTAAA GTTTTTTTTC ACAGCATGGT TTTGGTTTCT
14551 TTAATTCTAA GGAGCTCACC TGGTGTTACG TTGGAAAAAA CAGCTTTTAT
14601 ATCTCATTTA TATTCCATAT GCCAGTCTGC AGTGACATAT CTATCTGAGG
14651 TTTACAGTGT TAGCCACAAA ACACTCCCTA AGTGAATACA TTGACTGCTG
14701 TAAGGGGAGC CAGTCAGGAA GCACCTGCAG AGAAAAGCAG GCAACATGTA
14751 TAAACAGAGT TAATTCAGGA ATGAAAGCTG AATGGCTGGG CGAGTCTGTT
14801 TGTTTGAGTT GACAGCCTCT CCCTCACTCT TTCATTAAAT ATCCAACTAA
14851 CCTTCAATTG CCCTCTTGGA ACTTAATCTC AGTGTAATTT CCAGCATGTC
14901 AAAATTATCA AGCAGAAAGA GATACTACCC TGAAAGAGGG TCTTTTGTTC
14951 AATGCTAGGA GACAAACTCC AACTACAAAA TTCTAGAAAT GCCCTAAAGA
15001 GAGAGATAGG ATAGATTTAC AAATTGCTAA TGCTATTAGG TTGTATAGAT
15051 AACAATAGAT TTATAACAAC CTGGCACACA GCTTTAAATA TATAAGTTTC
15101 TCTGAAACTT CTGGGAACTT GGAATGCCAG AACGTTGGCA AAAAGAATGC
15151 TTCTAATAAT GAAAGCCATC ATCTGCCATG GAAACAATTT CAGGGTCTTT
15201 AGAAAGCTAG TTTATACATA AGCTCCATTC TACAATAAAA CTTATGTTCA
15251 TGTTTTTTCT GATTTTCCTC CTGCTGTAAA TTCATTTTAT CAGAATTCTT
15301 TTTACCAGTC CCTCTGCCCC ATTTCTCAAA GCGTTGTCCT CAGACTACCT
15351 GTATCACCTA AAGATTCTAA GGCCTCCTCC GATGTAGTAA ATGAGACTTT
15401 TCTAGAGAGA GAGTCCTAGA ATTTTATAAA GAAGGATCCT TTTTATTATT
15451 GTGATCACCA AAGTTACTTC TGCCTAGATT CTTCTCATGT TATTTTTACA
15501 GCTCCTATCT TCCCAGACAA CCTAACAATT CAAAGATAAA ATTGGTGCTT
15551 GGTTTAGACA TTCATAGCAG GCACGGTGCC AGATTGATGA TGTCATCCAG
15601 AGTCAAAAAC TTCATCCAAT GCCTTCACCA AAAAGTTACA AATGGCCAGG
15651 AATCAAATGT GGTTGAACTT ATTCAGAGGG TAATTACAAA ACAAACTTCT
15701 TTAAATACCC AACTGCTATT TGCTTTTTTC CTTCTAAATT GTATCACTTC
15751 TCTCCCTGTT CCATTTTGTT TGCCTTTTTA TTTTTTGGAA TCCCTCACCT
15801 CCATACTGAG TAGTAGAGCT GGCTGTGGGT GATGAGAGAG AAATTGTTAT
15851 AACAAAGTCA CCCTTTCAAA AACATGTCTT CCAAAAGAAT TTTGTTTCTA
15901 GCAGATAAAC CCCACACCAC CTCAGCTAAA TGGGGCTTTC TTTATTTAAG
15951 TACCAATAAA GACATATTTT GGATACTAGC AATTTATTTT CCAAATGCTA
16001 TCTTTGATCT TAAGTTTAAG GCTATTACCA AATCTATATC TCTACAAGTT
16051 TTATACTTTA GGTCAATAAA TTACTTGATA ACTTATTACT ATGTGTTCTA
```

FIGURE 3-7

```
16101 CAAAAGAAAC CGAAGTAAAA TTTACATCAC ATTTAACAGG GTGGTTGTGT
16151 GATTGAGTGG GAAGAGGCGG ACCCTACAGA TAGAAGACTT GGGTTTCAGT
16201 CCCAGCTTAC TAGTATCTGC GTGATGCCAG GGAAATTCAC ATAATGCCTC
16251 TGAGTCACAG ATTTCTAACA GGAATGAAGA TACTTCTTCG CAGAATTGTC
16301 ATTAGAGTTA AAGAAGATAA CAAATAATGT GGTTCCTGAT GAGGTATTTA
16351 TGAATTCCTG AGCATGCTAA GGAAGTTATA ACTTGTTTCT TGATCCCTGA
16401 AACAGCTTTC CCTATATTTG TGTGTGTGTG TGTGTGTGTG TTTCAGTCAT
16451 GCAAGTTGGT TTTTCTTCTC ATTCCTTGAG AATTTAGGAT ATTTTGTGCG
16501 CACATTTGGT TCTTCTGTCC AACATGAACT GTAGTACCTT ACCCACATTG
16551 AGATGACACT ATTTCTACCA AGTGAGTGCT AGGGGATACT GCAAGCCGAA
16601 TGCCAGGTGT GAGAGACCAC AGCATCACAA TACCGTGGCA GTAGATTAAA
16651 GCTGTGCATA TGGACTAAAA GCAGTGGCTT TGCTTCTCCT ACCTTGGTGA
16701 CATAAACTGA GTAACAAATT TGACCTAATA CTGGAATACC ACCTAATTCT
16751 TTTTTCCTCC CTGATTTACC CTAGAGTCCA CAATTGACAA TAATTTAAAA
16801 ATTTTGGCTC TCTCTTAAAT CCCTAATGCC TCCTCCTTAC ACCTTACAAG
16851 CAAAGACCTG CAGAGCTAAG ACCTGTAATG CCAGGATGGA GGCTAGAGGA
16901 CCATCAGCAA TTAACTACCA AAACTTACCC AACATTTTAT ATCTGTTTAA
16951 CCTTCATAGC CTTATGAGTA GCAGATCAAT ATCTTTGTTT TACAGGTTAG
17001 AAAACTGAGG CTCAAATTGA TTCAGTAACT TTGCCAAGAT TGCCCAGTTT
17051 GGGAAAAGTA GTATACGCTC AAATCCAGGA CTGAGGCAGG GTTTTCTTTG
17101 TCACCACTCA AAGCCTCTCT GAATATCCTA TCTCTGCTCT GTATCTCTCT
17151 GCTACTCCTT CTATGGTGTT TTAGCAAGAT ATCTTCTACT CCAGAAACCT
17201 ACTCTAGCAC AGTAGAATTA CTTGGGTAGG TTTTTTAAAA ATATGAGTGC
17251 CTAGGTCCCC TCTAGACCAA TCGAAACCAA AATTCTTGGA GAGGATCCCT
17301 GGCATCCATA AATTTTTTTA ATTCATCAAA TGATTCTGTT GCACTGTGAA
17351 AGCTGAGATC CACCAATTTA AATAATGATG TTAGTTCTGT GAAAAAATTT
17401 TTGATTGCTT TAACATTTAA TCAAGGATAT ATTCCTATTA TAAAATATAT
17451 TATTAACACA TAGTTTCTCT CTTGTTGTGT AACAGGTGGA TGAGATATTT
17501 ATAGATTCAG CCTGGAAGAA AAATTATATC AAGAACCAAG TAGTCAGACT
17551 GACGTATGTA TGTTTGGGCA AAGGTGGAAT CACAAGACTG GAGGGAAAAG
17601 GAACAAAGGA GACAGGGACT CTCATGTATT GTATGTCTCC ATGGACTAGG
17651 CTTTTGGCTA GAATTTTTCA TAAACATTAC CTTTAAAGCA GTCTTGAAGT
17701 ATAGGGCTGA CCACCGTTTT GTCAACAAAA AGACTAAGAT TCAGGAAGGG
17751 TAAGAAATAT GTTCAAAGTT CACCAACTGA CAGTTTCCCA AAGTGACAGA
17801 ACCAGGAATC AAACCCCATT AACTTATTGT GAGGCCTGGA ACCTACCAGA
17851 ACCCATGACG TGGGGAAAAC CCAGCAGCTT GTCGTTGCAT GCACCAAGTT
17901 ATATTATGTT GACAATTATA TTATTTCAAC CACGTTAAGC AGGCAAACTT
17951 GGCTATAAAA TGGGTTCACA AATTTTACCT GTAATGTAAC CGAATGACAT
18001 AAGGCATGCC TAAACAAAAA GATATTCCTG TTGTAATAAA TTTTCTTTCT
18051 GTCATGGTGG AGGGGGAAGA CTCATATCAG TTGCAGATAT TGCTCAGAAG
18101 TTTCAATTGT GTTATTTTGA AAAACTACAT AGCAGAACAC GCATGTCATA
18151 TACACAAATC CATGAGCCTG TATGACTCAT ATTTCTTAAA GATAAAGAAA
18201 AATAATATAT TCAGATTTTG ATTTATTTGA AGAAAATAAT TATCCCTTTC
18251 TCACCAATAG ACTAATAATG CTTTGTTGGC AGGTGTACTC AAAGTTCTCT
18301 ATGTCTTGAC TGAGTAACTA GTGACTTCCG TAAGGATTTT ATAACATAAA
18351 TTGGGTAATT CCTACAATAC TTAGGAGGGA AAAAGCATAT AAATGCTAGA
```

FIGURE 3-8

```
18401 ACTTTCTAGA TTTCATGTTT TCTGTTTTCA AATTCTCCTT TACCATATTA
18451 TTGTAGCAAC ATTATTATAC TCCTGTGAAC TCCTTTGGAT GGTAGCCATC
18501 ACTATATAAT ACCTGGTAAA AATGTTAATT CCTCAGATTT AAGAAGTAAA
18551 ATTAGTCATC TGTTTGCCAA TTTGACATAA AATTCTAGTT ATTTAGATCT
18601 TTATATTCCA GAGCCTAAAT GAACAAAAAT ACATAAATTG TCTCAGAATT
18651 TCCTTTTAGC CAAAAGATTC AGGGAGATGG GCCTCTAGAG TTTTTCACAG
18701 TTTTTTTTTT TTTTGTAAAA AAAAAAAAAA AAAAAAAAAG GAGAGATAAC
18751 AGATCAATAT ATATTAGTTT CAAGGTTTTT TGTTTTTTTT TTTAAACAAA
18801 AACCTGTAAT TGCTTTTCCT ATTTTAACAG TATTTAAAAG TTTAGTTCCT
18851 CAGGTAACAG AACTTGAACC TGTTTATATG ATCAAAGTTC AAGAAATTGG
18901 GCATGTTTAA TTTGGAGAAG ACTCGGGGAC CACAATATTG TTGTCTTCAA
18951 ATATTTGGGC TAGAGGAGGA AATTATTTTA TGTATGTTCC AACTGGTAGA
19001 CCTAAGCCTT ATGGAATGGG AGATATAGGG AGACATATTT CAACTCAAAA
19051 TGATGAACTC TTAAAAGCAG AGCTGACCAA AGAGAAACAA GCCTCTTTAG
19101 AAAATTAAAC TTACTATCTT TTTAATTACT GCACTGTCAT TAGAGGGCCA
19151 ATTGTCATGG ACCCTGTAGA AGTGATTCAG GTATCAAATA TACAATTGAT
19201 TAGCCTAAGA AAACATGAAG GCTTCTTCTA ACTCTCAGAG CTTGTAATTT
19251 TGATGATGAT TTTTTATATC TGTCATTCCT AGCTGCTGTA ACAATCCTTC
19301 AAATTAATGG GGGAAATGCA CTGAAAACAT AATGAAAGCT AGAAGAGGGA
19351 ACATATGAAA TGACCTTGGG TCAGAATGAC ATGAGAGGAT CAGCACTTGA
19401 CACTCTCAGC AACTGAGGGA TCATTCAGGG GAGGAAGATA CAGGTAAGAC
19451 TGAAGGACAA TTCCAGGTGT ATTCTTTGAA AATGTACCTT TCTTTTGTGT
19501 GTCACAGTCC AGAGGAAGAT GGTGTGAAAG TAGATGTCAT TATGGTGTTC
19551 CAGTTCCCCT CTACTGAACA AAGGGCAGTA AGAGAGAAGA AAATCCAAAG
19601 CATCTTAAAT CAGAAGATAA GGAATTTAAG AGCCTTGCCA ATAAATGCCT
19651 CATCAGTTCA AGTTAATGGT AAGGAGGTCC CCTTCTATGT GATATGAAGT
19701 TGTCTATTAG GTCCATGTTT TGACGAATCT CAAATTTATT TGTCATTATT
19751 TCCATTTCAA ATAATAGCTA GAATTCAGAT GAAAAAATTC AAGTTAAAGA
19801 TGTGACATTT CAAGGTGTAT TAGTCTCTAA CGTAAGCATG TCTGAAGTTA
19851 GTCATCCAGT GGTTTTCCCG ACAGTAATTG ATTGGCACTC ATCCCAAAAT
19901 ATAGGCAAGC ATTTACAACT AACAGAGAGT TAATCCCACC CAGGCACTGC
19951 CTCCATGACT AAGCAAGTGA AAATACTAGG GGTTTAGCAA TAATTGTTTT
20001 TCTGGGTGGG ACCTTCCTAA AACACAAATT CATGTGTTGC CATACTTTTA
20051 TTGATAGTTT CTATATATGG TGATATACAA TTTTTGTTAG CTTTTTTTCC
20101 TATGGGCATT TGGGAAAATG GCAAGCCAAC TTTGAAGTTG TTAGAGTCAT
20151 TTTACCATTA ATGCTTTAAA AATCACAGTC TAGGAAAACA TCACTGAAAC
20201 TATGTGTACA TTGTTCCACT TTTCTCTTTT TTTTGTTCA CCCTTAGCCC
20251 ATTATACCAT TATCACTTCC CTCAATTAAG GAGAACAAAC CTTTATCAAG
20301 GTCTATCTCT ATGGCCTTTA CCTTAAGTAA CTAATTTCTT TTTATATTCC
20351 AGTGACGTAC GCAAATTCAC CTTTATAGAA GTGAAATTCA CACAAAAGA
20401 GTTGAGGAAT TCAGTAATTA AAAGGAGCTA AGAATCAAAT TTAAATCTCT
20451 AATTTCTTAA AAGGCTCCAA TTAAAAAGG TTTCTATAGT CAAACACATC
20501 TTAAAAATTC TGGCTTTGAT ACTCGTTTCT TGGAAATTCT TCCTTATAGT
20551 GTCATATTAA AAATTCTAAG GCAGCCAGCT AGAGAGAAAC TTGTTTACCC
20601 TCGTCCGCTA AGCTGTTTGC ACAGCATCTT CTTCCAACAG ACAAGTATAG
20651 ATTTCTCCTA CAAATTTCAA TGGATACCAG ACCTAAGTGT TACAGAAGAG
```

FIGURE 3-9

```
20701 ATTCAGGGCA AGCGATTTTT ATCAGACATG AAACAGGACA CTCTGCCCTT
20751 GTAAGGGTCT AGCTGACACT TCAAGAGGAA ACCAGATAAG GAAGTAAAAA
20801 ATGTGAGGTA ATGGAATGGG CAGATGTTTG CTGATGTGAG AACGAGTCAG
20851 CTACTTAGGG AATAAAGCTG AGGACCTCTC CCAGCCAGAA GGGAGGAACC
20901 TGACAAGTGC TTAATCCATC TTCTTTGTTA GATGGGGAAG CAAATGAATA
20951 GAAGTTGTGA AACAATGGGC ATTCTGATAA TTTACATGAT GCTTTCTGTG
21001 TAATTTCCAA TAAATAGTTA ATTTGTCAGG AATGTAAAAG CCTGAACTAT
21051 CTGAAACCAG AGTAAAGCAT AAATTGTTCA TTGGCTGCCT GGTCTTTTTG
21101 TTTTTTGTAG GCTCAGCTTC TAAACTTCAG CTTATTTTAA TAATTGTACT
21151 AAATTAAATG GTAGGATATG CTAATGGAGA ACCTGATTTG AGAGTCACCT
21201 GAGGCTGGGC ATGGTGGCTC AAGCCTATAA TTCCAGCACT TTGGGAGGCC
21251 GAGGCGGGTG GATCACCTGA GGTCAGGAGT TCAAGACCAG CCTGGCCAAT
21301 ATGGTGAAAC CCCGTCTCTT CTAAAAATAC AAAATATTAG TCAGGCCTGG
21351 TGACGGGCAC CTGTAATCCC AGCTACTTGG GAGACTGAGG GGGAAGAATC
21401 ACTTGAACCC GGGAGGCGGA GGTTGCAGTG AGCCAAGATC GCGCCACTGC
21451 ACTCAAGCCT GGGCTTGACA GAGCAAGACT CCATCTCCAA AAAAATAAAA
21501 AATAAAAGAG TTACCTGACC AATTCTAACT CCACTAAGTC ACCACAGGAC
21551 CACCCAAATA ATTGGCTCAT GCCTTTGTCT TCATTTTCTC ATCTGTAAAA
21601 TTCCAATGGT AATGTTTGTT CTTCCTGAAA TCACAGAGAG ATTATAACGA
21651 TATACAAGGA AATAGAAAAC ACAATGTGAA ATAAAGAGGC TGTTACTAAT
21701 GAGAAAACTA TTATGTTGTG CATATGCTTT GGAAACCTGA AATCATTAAT
21751 TTGAGTGATT GACTAGTAGC AGAAAGATAG ATCCTTGAAA GTTTCAGAAT
21801 GTTCAATGTA GAAAGAACAG TGTTTGTTAG TGATATGGGA GCCTAGGGGG
21851 TGTTGCTTTT CTGGCCAGAA ACCTCTGTGG CCAGTGGTTG GTGCCTTTGC
21901 CCAAGTTTTG CTCTGGCCCA CTGGGCTTGT TCTGCCCACT TGACCTGGCA
21951 GACTGTGCCC ACCTTCCGCT ACCAGCCTGG ATCCCATGCC CACCAAGGCC
22001 AACCCAGGCA TGGAGCTGTG AGGGTTGTCT GAGCGAGCAC AGGGTCTGGC
22051 CACTGCCCAC AGCCAGGCAC ACTGGCTGCA GCATGACGGG CAGCTCCAGG
22101 CACTGGCACA GGTGTGCTGT CTCTCTGTGA GGCTGTGGCT GGACAAAGCT
22151 CACTGCAAGC AGCTTCCCTG GCAGGCACCT GGGAATGTGG TGGCACCCAG
22201 GAAGCTTGGA GATGCCAGGA ACTGCAGGGT CCCAAAGAGG GAGTCACAAC
22251 CCTGGCTTGG GGAGCTCCCA GGTCTGGGAT CCCTAAAGGG CTGCAGCTTT
22301 TCTCTCTTTT TACCCACAAT GTGGCCAGCA AGGGGTATGT TTCATTCCTG
22351 TTTGTGTTAC AGCTCTTTTA GTCTTGCTAT TTGGCAGGTC CTGAGTTCTT
22401 GTCCTGAGAC CAAGAAGAAT GAGGTATGCA GACAAGTGGA GGGTGAGCAA
22451 GACGAAGAAA GGTTTACTGA GCAAGAGAAC AGCTCACAGG AGACCCACAG
22501 TGGGCAGCTC CTCTTCATAG CCAGGGTGTC CCAACAAGTG TCCAGCTCCT
22551 AGCAAAGAGG AGGCCCTGGA GGTAGAAGCT CCTCTCTGCA GGCAGGTTGT
22601 CCTGTTGAGT GTTCAGCTTT CAGCACACAG TAGGCAGTAG GCCCTAGAGT
22651 GGTCTATCTC CTCTCTGCAG GCAGGTAGTC CCATGGTCTC CCAGTCACCT
22701 CTCCATCTGC AAGGGTCCAA TGCTGCCTCC AGCACCTCTC TGCCCACCCC
22751 TCCGTGCCTG ACCAAGCTGC TCCCCCACCA GTGGGCAACT CAGCCCAGCC
22801 CCATTGTGGT AGCTCCAGG GTGGCAGGCT CTGGGGGCT CCCAGGGATG
22851 GGCTCCAAGG ACTGTCCACC TTCTCCCCAC GCCCTCCCTG CAGTGGCCAT
22901 GGTCAAGAAT GGCAATGTGG GGCCAGGTTC CGGAGCAGGA GAGGCTCCAG
22951 GCCTGGGAGC AGGTCCTGCC TGGTCACGTG AGGTTGGGGG TGGCACAGTC
```

FIGURE 3-10

```
23001 GGCTGCCTCA GGGATGTGGG ACACAGGGGA CCCACCACCA TCACTGCTAC
23051 TCCCGCATCC GCTCCTGCTA CCACTGCTCC AGACAGCCTG TAGCTGCCAT
23101 CACTAGCACT TAAGAAAGGC ACATTCAGTG GACAGCTCAG GAAAATCTTT
23151 ACGTCAATTT TTTATAGGCA AAAACATTGT TTCCTGGGCA AACAAAATTT
23201 ATGGACTACC AATAAATAGA AAACTGTAGA GATTCTAGAT TAAGTCTAGA
23251 AATAATCCTG TAGCCCAAGA TTTATTTATA ATTTGTCAAG AATCTGTATT
23301 TTGTTTTGAC AAAAAAAAAA CTGTGTGGTG TGGGTCCTTC AGGAGACACA
23351 GTGTGACAAA GCAAAGCTAA AATCAACTTC TTTGCATTGC AAACACCAAG
23401 GCTGTAGTCA AGCAGCTCAC TGCCTATGTG TCAGATGACT TTGCTTCATT
23451 TTTCATCATG ATACTTGTAG TCTATAGAGC CCTGAATATT AACTAGCTTT
23501 CTCCCAACTC AGAACCGTGT TAGGAGGTGG TTGCTTTCAA AACTAAAGTG
23551 TTAATGTTTA TTTCCATTTC TATACCAGGA AAGTAAAAAT CTTTGGTCAA
23601 AATTAGAAAT CTTTAACAAC TAGTTACTTG TGTATTGACA GTTTGTTTCC
23651 AGGTGTAATC ATTCTCCCTT AAAATCCGGT TATATTCACG ACCATTATAC
23701 TTATCCTGGT ATCATTCCTG GAAATGGCTA ACTTGCATCC TGCTCAGACT
23751 AAGTTGACAA AGTTTCAATT GAAGAATTCT AACTTTATGC TATTTTCCAC
23801 TTTATTGCAT TACAAAGGAC AAAATATATA GTTTTCTTAA AAATGAAATA
23851 AATTTACTGC CTTAAACTAC ATTTGACGGT AAACTGAGTT CCTTCCATAG
23901 AATAACCACT AACAGCAATC GATGGTCCTG AGCAATTGAC TCTTCACCAT
23951 ACAATGATTT GGGATGCCTT TAAGGGTATA TTTGAATTGA ATATTTTCAA
24001 AAGCTCCCAC TTTGTAGAGT TTATCATCAC TAGTTTCCCC AGTGGAATTT
24051 GTAGAAAGTT AGTAGAATGA AACAATCTTA TTTTGTATAA TGAGGAATAG
24101 AATACTGAGA ATGTGTCTGA GAAACATGGC ACTGGTAGGA AAAAGTAAAC
24151 AGTTTATTCT CATCTGCTCA ATAAGCTAAG TCATTTTAAC TTGAAAATCA
24201 TCAAAATTTT CATGAAACCT TCCACCAACT TTATTTTTCC CCAGCTTTAG
24251 TAAGATATAA TTGACAAATA AAAATTGTAT ACTGTATACA ACATGATGCT
24301 TTGATACATG TATACAAGTT TAAATATTTG TGTTTCCTTA GTCAAACTCC
24351 TCACTTTTTT GGAAGTTGAC AGAATTTAAT CTTGGATTGT GTCCAATAAC
24401 TAGCTTTTAC CACTATTCAG TATATTTTGG ATAAGAAACA CATAACAGTT
24451 TATTCTTTAA AAAAGCAATT TTACTATTTA GGAACTGTGT TTAAAAAGCA
24501 TTTTAAATAT CATTTATGCA AGAGTTTTCA AGGTTTTTTC ATTCTAAACC
24551 CTTTAACCAA AAAAAAAAAA AAAAAGATTT ATGTGAAATT CGAAGTAAAT
24601 AGAAGAGATC AAAGCAGATC TGTTCTGGCT GAGGCTGAGT TTGAGACCTG
24651 TAAGACAGTC TACTTGCCAT ATGGCTTGGC TGTGTCCCCA CCCAAATCTC
24701 ATCTCGAATT GTAGCCCCCA TAATTCCCAC ATGTTGTGAG AGGGACCTGG
24751 TGGAGATAAA ATTAAATCAT GGGTGCAGTT TCCCCCATAC TGTTCTATGG
24801 TAGTGAATGA GATCTGATGG TTTTATAAGA GGCTTCCCCT TTCACTTGGC
24851 TCACATTCTC TGACTTGCTT GCCACCATGT AAGACATGCC TTTTGCCTTC
24901 CTCCATGATT GTGAGGCCTC CCCAGCCACA TGGAACTCTG AGTCCATTAA
24951 ACCTCTTTTT CTTTATAAAT TACCCAGTCT CAGATATGTC TTTATCAGCA
25001 GTGTGAAAAC AAACTAATAT AACCTGTTTC CTCTGTCCCA TTTATCCATC
25051 TTCTGAAGTG GAATGCAAAG AAGCTTTACC CCGAACTGCT GGAAAACCAT
25101 AGTTCTCTAT TAATACAAAC TATTTGTGGG CTTTAGTCAT CCACTATTTG
25151 TGCCTTACTC ACCCATTGCT TGTGATAGTA TCCACCTAAT TAGAGGCTGC
25201 CTATAAGTCT CTACAAAAAC TGTACACAGA TGTTGTTATA TCAGATAGCC
25251 ATTCTCCTAA TTAATCTATA TGTTCAACTG TCTAGAATCC ATATATGGTC
```

FIGURE 3-11

```
25301 AGTATCCTCT GATTATTCCT GGTCATTGAG ACCAACCAGG AAAATATCAA
25351 ATTATCACTA TTTGTTTTAT CTTCTTTTTC AGCAATGAGC TCATCAACAG
25401 GGGAGTTAAC TGTCCAAGCA AGTAAGTCAA GTTAGCTTAT ATAAACAAGT
25451 TCAATTTTCA CATCAGAAAG GACATTTTCA AATATTTGCT CATACTTGCC
25501 CATCTGTCCT CCAGATTTTC TTTGAGAGAT AATAACTATT TGTACGATAG
25551 ATTTAAATAC ATTTTTTTTC TAACTCATGG ACTGATCTTT TAGTCATGTT
25601 CAAGAAAAAA ATTGCCATGG TAACCTTCTG GGGCAATTTG AAGAAAGCAT
25651 TTATTTTTGA TTGGGAATAT TGGACTTGTT TTTCTAATTT TTAAAAATGC
25701 CATAAAATGT ACTTTCTGCT ACAAAATAAA ATAATAAGAA AGTAATCAAT
25751 AGGAAGGACA TAAAACCCAT TGTCTGTGAC TGACAATTTG TCTGTGAAAT
25801 ATGCTAAGGT CAGGAGTTCG AGACCAGCCT GACCAACATG GAGAAGAAAA
25851 CCCATCTCTA TTAAAAATAC AAAAATTAGC CAGGTGCGGT GGCAGGTGCC
25901 TGTAGTCCCA GCTACTTGGG AGGCTGAGGC AGGAGAATCA CTTGAACCTG
25951 GGAGGCAGAG GTTGCAGTGA GCCAAGATTG CACCACTGCA CTCCAGCCTC
26001 AGCGACAGAG TGAGACTCCA TCTCAAAAAA GAAGAAAAAA ATATGCTTAA
26051 TAGATTCATC TTAATCGCTA ACAGTGGCTT CATTAAATCA CTTCAAATCA
26101 CTGTGGCCTA AATTTTGAAA GATTTTACAA AAAACAGTGA TGAATTTGAG
26151 CAATGATGTT CATGCATTTG CCTCTGTGAC TTGCAAACAC CCTAAGTATT
26201 TTTATCCATG TGTTTATTCA TTCAACAATA TCTTTTAACA TCTACCAAGT
26251 GCCAGAAATT AGACCAGGAG TTGGTGGTAC CATTGTGAAT AAAACATGAT
26301 CCCTGCTCTA AAATTAGAAT TCCAAAGTAG AGAAAGATAT AAATAAATCA
26351 GGAAGTATGA AAATAATGTG ATTAATGCTA TGACAGAGGA AGTGCATAGT
26401 GCTATGAGAG TTGATCAGAG AGTCAGCTAA CCTGTTCTCA CACAGTAAGA
26451 AAGTGAACCC TGAAATGTGA GAGAGAAGAG GCCATGAATC CAGTGACAGG
26501 TGGGGTAAGT GTCCTGGGCA GGAGGAGTAG TATACGAAAA TGTCTTCAGG
26551 CAAGTAAGAA TGGGGTCATT TCCTGTAATT ACAAGATGTT TCTTATAACT
26601 TAATGATCTC ATCTTTTTTC AGGTTGTGGT AAACGAGTTG TTCCATTAAA
26651 CGTCAACAGA ATAGCATCTG GAGTCATTGC ACCCAAGGCG GCCTGGCCTT
26701 GGCAAGCTTC CCTTCAGTAT GATAACATCC ATCAGTGTGG GGCCACCTTG
26751 ATTAGTAACA CATGGCTTGT CACTGCAGCA CACTGCTTCC AGAAGTAAGT
26801 TATTGACCTT AAGTTAGAAC CCACTTCTGC TAAAAAGCCC TGAGTTTTGT
26851 CATATTCTTG GTAACAATTA ATGTCTCAAA TATTACTGAA GTAAAATAAG
26901 AAAAAGTTAT TTCAGGTTCT TTTCTAAAAT AATGTTACAC TTGCATACTT
26951 AATCAGAAAT TTGATGGGAA TAAGTAACAG TCATTATCCT AGTATCCATC
27001 AATCATTTCC TCAAAGTTTT TAATAAGGAA ACTGTGTAAA GAAATCAGAA
27051 CTATTTTGTG ACATCCTAAC ACAAAATATT CACTAATAAC ATGTACCATT
27101 AATCTTTTGT CAAACAATGC TCTCCACTTA AAACTAGTGT CTGTTTCTGC
27151 CAAACACTTG GGCCAGTCTC ATACTGATCT TAAATAATCA AACTAATTCC
27201 AAAGTAAAAT GGAAATTTTC AATAAATGCC GGAAGTTGGT AACCGTGATG
27251 ATGGAGAACT GCAGATCAAA TTTAGAGCAT TGACATATGA AGATCTGTGG
27301 AATCAGAACA GTTTACAACC AAAATGAGAG ATTGCTAGCA TGATAAAGAC
27351 AGGCACTTCA AAAGAGATTC CTCGGAGTAT CAAAGGATTC ATAGAGGCCC
27401 TTGGGCCACT CAATGTGACC TTCCCATAAT AGAGCATCTC TTCACAATAG
27451 TGACACAAAA GACAAAGCTG AAGTGAAGAA TAGCAAATTG TGCTATCCTA
27501 TAATTGTTTC TGAATGCATA CATTTTATTA AATATATGAT TAAATGACTT
27551 TTTATAACTT TTAATCTTAC TTTTCAAGAT AATAACCAGT CATTTTTATC
```

FIGURE 3-12

```
27601 ACTATTACAT TTAGAATTTT AGATTTGTTT CTAAGTAGAT TAACTGTATC
27651 GCCTTTCTTC TTCATTGCCA ATTATTACAG TAATAACAAA GACTTCTTGA
27701 GTATCTCTAT ATAATAGGTG GCAGCAGGAT TTAGTGGGAA AAATATGTCC
27751 CAGGCAGTTG GAGAGCTGGG CAAATTATTG AACCTTAGTG TATTAGGTAA
27801 TAGATAGGCT AGATCTTTTC ACATTCTTTT TGACCTATAA AATTCTAACT
27851 TTTGTTACTA TAATAAATTT CATTTGCCTA GGAGCATAAA TCTTTATAGA
27901 GACTCTTAAT ATTCCAAAGA ATATACATAT TAAGAATCTA GGCTTGGCAT
27951 GGTGGCTCAT GCCTGTAATC CCAGCATTTT GGGAGGCCGA GGCAAGAGGA
28001 CCACTTGAGC TCAGGAGTTC AAGACCAGCT TGGGCAAGAT AGTGAAACCC
28051 CATTGGGCAT GGTGGTGCAT ACCTATCATC CCAGCTACTT GGGAGGCTAA
28101 CGCAGGAGGA TCCCTTAAGC CCAGGAGTTT GAGGCTCCTG CAAGCTATGA
28151 TTGCACCACT GCACTCCAGC CTGAGTGACA ATGCAAGACC CCATCTTAAA
28201 AAAATAGTAA TATATTTTTA AAAATAATCT ACATAAATTC TTAATGTTTG
28251 AAAGATGTGA GAGCTCAGTA AGCTGATATA TTAGAAAGCC AGAAATCCCT
28301 TATGCTGGTG TCTGGTTTTT CAAAGTAATG GGAAACTTAC TTTGCCAAAG
28351 TTAGCCATTT TTGTGGTAGA TAGTTCTATT TTTGCAAATA TCTTTATAGC
28401 ATTGAACACC AAATCTATAC TCTATTAACT TCTACCATCA ATATTTGTTT
28451 TTCTTTTAAT CTGGAACAAC AGGAACCAAT TTTATTTCTT CATTCATATA
28501 ACAGCTATTC TTTAGTTTCT CTTTTTCAGA CCAAACATAA AATGAGGGAG
28551 AATATCCAAA CCATAAGTGA AAATAAATAT CATTACTGTG AGCTTTAGTT
28601 TGCTAAGGAT AATGACCTCC AGCCCTATCC ATGTCCCTGC AAAGGGCATG
28651 ATTTTGTTCT TTTTATGGCT GCATAGCATT CCCATGGTGT ATGTATACCA
28701 CATTTTCTTT ATCCAGTCTA TCACTAATGG GCATTTAGGT TGATTCTATG
28751 TCTTTGCTAT ACCGAAGAGT GCTAGAGGGA GAGGATCAGG AAAAATAACT
28801 AATGGGTACT AGGCTTAATA CCTGGGTGAT GAAATAATAT GTACAACAAA
28851 ACCCCATGAC ACAAGTTTAC CTGTGTAACA AACCTGCACA TGTAACCCTG
28901 AACTTTGAAA AAAGTATATA TATGCACACA CATATATATG CATACATATA
28951 TATGTGTGTA TATATATGCA TATATGTGTG TGTGTATATA TAAAAAAAAA
29001 TATATATATA TATATATATA TATAATTACC TCATTTTTCC AGAACCAACT
29051 TCCAGATGCC CTACCACATT GGTTCTTATT CTCTGAACAT TCGAGACTTT
29101 GTCAGTGTCT TCCTTAAAAT ATGCTTCCAA TAACTAAATA CACCAAGACA
29151 GATGTGTGAC TAGTGTCACA CATAACAAAA TAAAGCAGGA AGTCTTCTGA
29201 AAAATACAAA TAATGTAAAT TGGTGGGAGA CAGTGTTTTA TAAAGGGAAG
29251 AGCAGAGAGA GGCAGGCAGA TATGTGATGT GAATCAAATA GTTTAACCTA
29301 TCCAGGCTTT ATTTTCCTTA AGTATAAAAC ACAGTCTTTA CTAGATGATC
29351 TTTCATTGCT ACTAAATGAT TTTTCCGATT CCTGTATGTA CCATAATCCA
29401 CCCATTGCCC AAGCCCACAA GCTAGAAGTC AACCGCATTT ACCACATTTG
29451 ATCATCTCTC AAAGGACTAT GCAGTCATCT AATAGACTTT ACCACATCCA
29501 TTCTTGACCT TCAAGAATCT ACTCCCCAGA AAGAACAAAC ATGTTTTTTA
29551 AAAATGTAAA TGAGACTACA TTATTCTCTG GCTTAATTAT CCAGTAGATT
29601 CCCATATCAC TTCAATAAAA TTTAAGCACT TTATCATGAC CTATAAAACA
29651 CTCTAAAATC TAGTCCCTGC TTACCTCTCC AAGCTCACCC CCAACCATTC
29701 TTTCCCTTGT GTTCTGACTG CAGCCCATCC AACCCAAGAC CTTGGGATTT
29751 TTGCCTGGAA ACTTGTTTCC CTCATCTCCT CACACTGACC CTCTTTTACT
29801 ATGTCTTAGC CCAAATGCGT TATCAAAATA ATCATAATGA CCTGTTAGTA
29851 CTCTATTCCG TTACCCTATT TTATTTTGTT CATAGCCTTT ATCAATGTTT
```

FIGURE 3-13

```
29901 AAGATTATTT ATCTATTTGT TTGCTTGCTT TGATCCTTTT CCTTCTCTGG
29951 AATCTTATAC TCCTGTGAGC AGGCACCTTA GGTCCTGTTC ATCACTTTAT
30001 CCCCAGCAGT TCAGATAAGG CTCAGCACAC AGATGCTCAG TAAATATTTG
30051 TGGAAGGGAT AAATGAATGA TATTTTATGT GTATTACAGT TCTAAAATTC
30101 AATAGTTTTG TATTAAATAT CAGTTCTAAT ATGGCATTTA TATGATTTTA
30151 TCTTTCAAAA CATTAGCAAT AGATTATATT TAAATGATAA AAGAAAACTA
30201 TAACTGCAGC CAAGTATTCT CAGGATTGTA TTTCTCTTAT ATTAGCCTAA
30251 ATGCAATTAA TCTAGCTCAT ATACTTTGGG CAGCTTATAT ATATTCTGTT
30301 AATTTCTAAC CTTTTCCAGG TATAAAAATC CACATCAATG GACTGTTAGT
30351 TTTGGAACAA AAATCAACCC TCCCTTAATG AAAAGAAATG TCAGAAGATT
30401 TATTATCCAT GAGAAGTACC GCTCTGCAGC AAGAGAGTAC GACATTGCTG
30451 TTGTGCAGGT CTCTTCCAGA GTCACCTTTT CGGATGACAT ACGCCAGATT
30501 TGTTTGCCAG AAGCCTCTGC ATCCTTCCAA CCAAATTTGA CTGTCCACAT
30551 CACAGGATTT GGAGCACTTT ACTATGGTGG TGGGTATCTC AGGATAGCTA
30601 ACAGAGCGCT AAGCCCTGTC TAAGGCAATG TGATTTCATC TCCATCAATA
30651 TTATCCTGAC AGCCATTTCC ACACAGTCTG GTTGGATTAG TTAGGGTTCT
30701 TACTTTGTGT GACAGAAATT CAATTCACAT TAACCAGTGC AGAATAAAAA
30751 ACAAAGAAAC AAAAACTTCC ACAAATTTGG CTCATGTAAT TTGAAGTCA
30801 AAAAAGTGTA GTAAGTTTCA CTTCAGACAC AGGGGTTTAT ATGATGTCAT
30851 CTGGCTCTGT GTCTCTGAAT TTGAATTTTT TGCCCCTTCT TTTCTCTATG
30901 TTGGCTTCAT TCAGAGGGAT GCTAGCTTCA CCTAGTGTCA GAGGTGGCTA
30951 ACAACACCTC AACACATCAT CCTCAACAAA GAAAAAATAC ATAGAAAGGA
31001 ATATTTATTT CTTTTCTTTG CCAGAATTCA CATTAATTTC TATTGTTCCA
31051 GCTGTGTCTA GGAGGACTCA GATTGAGTGG CTAACTCAAA TATTCTTTAT
31101 GCCTATGTAG CAAAATTTGC TTCAGTACTG AAGAAGCTAA TTTAAGTGTG
31151 ATGGTGAATA AGAATAGTGT AGAGATAAAT TGTCAAACTA TTTGTCCCCT
31201 CTAAAAGTAT TCAACTTGAT ATACTAACTT AGTCTTGTAA GAAATAATGA
31251 TGATTTAGTT ACTGAATGTT CTAGGCAATC TTAGTGAGAC ACGCTCTGGA
31301 TTCTAACATG TGGTCCAGGT ACATATGTAT AACAAAGCTA GAAAGTTTCT
31351 TTAACACTGG GCTTGAGAAA ATGCAAAAGG GCTTTCTGAG AATGACTAAA
31401 TCTATTTGCA GGATTCTATA CAATTTATTT ACATACAAGA AATTATAAAG
31451 AATAAGCTTT TGATTCTCAG TCTACCATTA AGGAACTAGG AATAACCTTT
31501 CACTCACATA GGCAGGAATC GGTTTTAGGG TCTCTAGATT TTTTCCAGAT
31551 GTCCCATGTG GTTTTGTTTT ATCTTATACA GAGTGAGACA TGCATTGCTT
31601 TCTTTAAGGT TGTATTACCA ATCACAGAAA ATATTACCTA TGGTTTATTA
31651 ATTCTAGTAG ATCCAGTGCT GCTGTAAGCC TGACACCTCC CTAGGTCTGC
31701 ACTCTCTTGG ATGGATTTTC TCTGAAGATA GGGCTTGCAT TCTCTGCTTC
31751 ATAGTGGTGG GAAAGACATC ACAAATCCCC TTTGGCTTGG TGGGAAAAAT
31801 CACTTTCAGG AGTTTGAGAC TGGCACAGAA ACATACCTGT CATAATGCGC
31851 TGTGAGTGGC AACAGAATCT GACACTTATA GAGCACTCCA CCCTACTTGA
31901 ACACGGCCTC TCTTGGTGAG TGACCCACAG GTGCTTTTAA TCTATTAAAT
31951 AGATTAAATT AACCTATCAT TCTTAATCTG TTAAGTACAT TAATAGATTA
32001 AAAGCAGCCA TTCGTTACTC ACCAAGAGAG GCTATATTCA AGTCTGTAAA
32051 GCAAACCTTA AGAAGTTTTT TAAAATTGAA ATTGTACAAA GTATATTCTC
32101 TGATCATAAT GGAATCTAAC TAGACATCAG TAACAGAAAG ATAACATAAA
32151 AATCCCCAAA TGCTTACCAA TTAAAAAACA TATGTAAATA AAGAGAATAT
```

FIGURE 3-14

```
32201 CTCGAAGAAA TTTGTAAAAA CAAATAGAAC TAAATGAAAA CAAAAATATA
32251 TAAATATATG CCAGATGCTG CTAAAATAGT GTAGAAAGGG AAATTTATAG
32301 AAAATGCATA TTATAAGGAA AGATATCAAA TCAATAATTA AGTTCTCACT
32351 TCAAGAAACT AGAAAAATAA AAAATAAACC TAAAACAAAC ATAAGGAAGG
32401 AAATAATAAG AATAAGAATA GAAATGAATA AAATTAAAAA TAAACTATAG
32451 AAAATTGATA AATAAAAAGC TGATTATTTG ATAAAATCAA TATTTTGCTA
32501 GAAATGTCAT TAAGCATTTT TACAGAAGAT GAGATATAGC TCAGGGATGT
32551 CCAGAATTTA TGGGCTATGC TTTTCATGAC TTGGAATACA TTTTACCAAC
32601 CAGTTTAGTT TGCTGAAGAA GTTGTGGATT TGCACTGTCA CCTACTTACA
32651 ATACTTAGAT TGTCAGTTTC ACCTTACTCT TCTCACCATT ATTTTATTTT
32701 TATTTTTATT TTTATTTTTA TTTTGAAACA GAGTCTCGCT CTGTCTCCCA
32751 GGCTGGAGTG CAGTGGCGTG ATCTCGGCTC ACTGCAAACT CCGCCTCCCG
32801 GGTTCACGCC ATTCTCCTGC CTCAGCCTCC CGAGTAGCTG GGACTGCAGG
32851 CGCCCACCAC CATGCCCGGC TAATTGTTTT GTAGTTTTAG TAAAGAAGGG
32901 GTTTCACCGT GTTAGCCAGG ATGGTTTTGA TCTCCTGACC TCGTGATCCA
32951 CCTGCCTCGG CCTCCCAAAG TGCTGGGATT ACAGGCGTGA GCCACCGCGC
33001 GCCAGGCCAT GAATGTTTTT AATTGATGAT ATAGTAGGCA ATATAAATGT
33051 GTGTGTGTGT GTGTGTGTGT GTGTATAATA TATATAAACC AATTGTATTC
33101 AAATAACAGA ATAATTTGAA AAATCTCTTA GCATATTTCT GAGTTACACA
33151 CTTAAATCTT CCGAGCACTT TTAAATATGT GTTTACAAAC ATTTCTTCAG
33201 AAATAAATCT TGGAAATCGT CTTCTAAAGA AACTGGTGTA TTAGGGTTTT
33251 TTCAAATGTA CTTAGTTTTT TTTTTAATTG ATGTATAAAA TTGCATGTAC
33301 TTACCATGTG CAACATAATG TGTTGAAGTA TAGTATATGT ACACTGTGAG
33351 TGTTAAATCT AGTTAACTAA GAAGCGTCTT ATTTTACATA ATTATCATTT
33401 TTGTGGCAAG AACACTTAAT ATCTACTCTT GTAGCGTTTC TCAAGAATAC
33451 GATATATCAA CAGTAGGCAA CCAGAAGCTG GGGGTCTTTA CAGGGGAAGG
33501 AGTTAGGGAG ATGCTGGTCA ACAAATTCAT ATTTGCAGTT AGGAAGAAAA
33551 AGTTCAAGAG ATCTCTCATC CATCATGGTG ACTATAGCTG ATGATATATC
33601 GTATTCTTGT ATTAGTTTTT TATAAATGTG TAACAAATAA TCACAAACAG
33651 TTAAAACAGC ACTCATTTAT TTTTATCTCA CTGTTTTCAT GAGTCAGACG
33701 TTCAGACACA GCTTAGTTGA GTCCTCTTCT CAGGGTCTCA CCAAACTGTA
33751 ATCAAGGTGT CAGCTGGGGT TGTGGCCACA TCTGTGGCTC CTTTGAAGGT
33801 CTCCTCAAGG TTTGCTGGCA GAATTCCTTT ACTCGCAGCT GTAGAATGCA
33851 TGCCAGCTTG CTGCTTTAAC TCTTTAGGAA AGTGTCTCAA CTCCAGCAAG
33901 GCTCGCCCTT TTTGAAATGG CTCAGCTGAT TAGGTCAGGC CCACCTTTGA
33951 TAATCTCCTT TTGATGAATT CAAAGTCAAA CTCATTAGAG GTCTTAATCG
34001 CATCTGTAAA ATTCCCTCAT CTTGGCCATA TAACATAACC TAATCATGAG
34051 AATGGCATCC CTCATATTCA CAGATCCTGC CCATATTTGG GAGGAGGGGA
34101 ATCACACAGG AATCTTGGGG ACTATCCTAG AATTCTGCCA ACCATGGGGT
34151 CATGGTTTCC CAATCAATAT ATGGTTTGGT ATAAAGAATC CCTGAATGCT
34201 TGTGCTATTC TTAGTTTTCT ACGTAGCCTG CCATAATAAT GGTTTCTAAA
34251 ACTCAGAACC TAGCTTACAG TCTGCAGCCA CCAACTTGTA ATACATTGGA
34301 AGTGAAATCA TTGCCGTTTA ATGCATTTAT ATATATATGA TGTATAATAT
34351 ATGTATATTT CACATATATC TTATATATGT GAAAGCTCAT CATAAACTTT
34401 AAATAATAAA ATAAATGTAC ATAGTATTAT AGGCATTTTA TCAAGCCAAT
34451 GGAGAAAACC ATCTAGGCAT GCAGAGTTTC TGGGAACAAT CTGGAACCCA
```

FIGURE 3-15

```
34501 CAAATAAAAG CTTTACAAAA GATAAAAGGC CTTCCTGAAA TATATAAGCT
34551 GATTATTTTT AAGGTTAGAT TTTACCAGGA AAAAGAATCC AAATGGCTTT
34601 CTTGCTTTGA GAAGTTTTTA TAAAAATGTG ATTGGACAAT AATTATCGTT
34651 AGATGTGCCA GATTTAACCA GAAATTCTTT TTTCTAGAAA CTGCTTATAT
34701 TAACTTCATT CTGTATTGAC AATTTTACCA TGAAAAAAAT ATTAGGAAAG
34751 TCTTCTCACT TCACTCTAGC CAAAGATGCT GATTGTAAAT ACTAGAATAA
34801 CTCTATTTTT CCTTAAGGGG AATCCCAAAA TGATCTCCGA GAAGCCAGAG
34851 TGAAAATCAT AAGTGACGAT GTCTGCAAGC AACCACAGGT GTATGGCAAT
34901 GATATAAAAC CTGGAATGTT CTGTGCCGGA TATATGGAAG GAATTTATGA
34951 TGCCTGCAGG GTAAGTTGGA GGGATTTTTT TATATTACTA ACTCAAAAAT
35001 TTGTATCTGG CTTAGAATAT ATTATATGTT CTTTACATAA GGACAAAACA
35051 TAGATATCAT GTCAGCTCAA AAAAGTTACA AATGCAAATT TCACAGCACA
35101 AAATACTTTT AAATGTTTTA TTAAGATAAA TGAAGTAAGA GTTTCTCTGA
35151 TGCTATCAAA CAAACAAAAT TAGAATTTCT TAACCAGAAA TCCAAAGATT
35201 AATAAAGCAG TTTATTTTCT CAAGCGGCTC ACATTCAAGA AAGAAAATAA
35251 TCATAAACAG AGAAGTATAA AGTGATGTTA TGAATAATAT AATGAAAAGC
35301 AAATATTTTT CTTGAAGGAA ACATTTTTGG AACAAGTATC AGAGAGATGA
35351 GACGTAAATA AGGCCTGAAG AATAAATAAC ATCCAATTTC AGAATAAGAA
35401 AATAATGTTA TAGAAAAGAC AAAAAGCATA GCCAAAATTA TGAAGGTGTG
35451 AAATTACAAT TCATATCTGA GGGAACTCCA AGTAATTGGT TGGGTCTCAG
35501 CATGAGGAGG ATGAGAAGAG AAACAAGTAG ATAACCATGA GAAGGTGGAT
35551 TAGGCCATGT TGTGATTCCA TGGGCCCTCC CCAGTGCCCT CATCTGCCTT
35601 CTAACATGGA TGTTTTCCAG CGAAGGTACG TTTCTTCCTG GAGACACTTG
35651 CTTTTTAACA TGAGATACTT TAGAACTCTA AGGAGGCCAC TCTATGTGGA
35701 AATGATGGAA TGGTATTGAT ATCAGGTGGC AGAAAGTCCT GTCCAGAGTC
35751 CCACAAACTG TACCACATGT GCGACCTCTA TCAGAAAAGG AGCAGGGACC
35801 TATGTGACAT AGAGGCTGGG CAAAAGCAGG ATCTGGTCCA CAGCCAGCCT
35851 CGGTTGCTAA TAATGTGGAG GGAGGCAGGC AGAATTTAGG GATTCCAACA
35901 AAAGGTCCAT ACCACGGGGA ACAGGTGGAA GGTGCAGGAG TCTTGGAGCA
35951 GACAGGACCG GGGAATTCAG GTGAACCATG ACATTACTGA AAAGCCTTAG
36001 GAGGGATTGG TGGTCATAGA GATGCTTCAC TGGATTGGGG AGCAGAGGTA
36051 AACTTGCTGC CTAACTGTGC AAAGTAAGTG ATAAAACAAG GCTTTAGTCA
36101 TAGAAAAATA CAGTAAGTTA TCAGGGCAGC GGTTCAGGTA CAAGGATCCA
36151 AGACAGGAAT ACAGTGATTG TAATTGGGGC ACATGGTGAG GGGCCTAGTC
36201 TGATACAACA GAAGTGCAAG CACCACCAAC ACCTCGTCTT TCTCCATAAG
36251 TCTTTCTCTC CAGAGCCCTC ATGACCTAAT CACCTCTTCT TAAGTCCCAT
36301 CTCTCAACAC TATTGTATTG GAGATTAAGT TTCCCCAACC TATGAACTCT
36351 TGGGCTCACA TTCAAACCAT AGCACCACCC AGCACAAAAG CACAGAGCTT
36401 CCAATCTGGT TTCTAGCTCC ATACCCTAGA ACCAAACAGT AAGAATCACC
36451 TCTGGAAATG TAGCAATAAT ATAATCATAA TTTTTAAAAT CCAGTGGAAG
36501 GATTGGAAGA TAAAATCAAG GAAATCTCTC AGAAAGAACA ACAACAACAA
36551 AAAAGACACA GAGGAGAAAA ATAATCAGAA AAATTAAGAA AACTAGAGGA
36601 TAAGCTCAGG AGATCCAACA CCAAATGAAT AGGAGCTCTG AAAACATAAA
36651 ACGCGAGTGT ACAATATAAA AAAAAATAAA GAATGCTCCT AGTTCTGAAG
36701 CTTACATGCA TCCTATTGAA GAAAAGGTCC AAGTAGTGCT GGGCACAATA
36751 AATGAAGTAC TTCTTTCCAA GACATACCAT CATAAAGGGT CAGAAGCCAG
```

FIGURE 3-16

```
36801 GGATAAGGAG AACAATCTTA AAACTTTGAA GGAAGAACCA TCAGAACTAC
36851 ATAGAACTCC TCAACAGTAA CTCTAGAAGG TAGACGATGG TGGAAAACAC
36901 ATTCAAATTT CAAAGGGAAG ATTATTTCAA CCTAGATTCC TACCCATGCT
36951 AACTAAATAT CAACTGTGAG GGTGGAATTA AGAAGTTTAG ACAAGCAATG
37001 ACTGAAAAAA ATGTACTTCT GATACCCTAC TTCTTAGGAA ACTACTTGAG
37051 AGGGTACCTC AGCAAAATGA GGGAATAAAT CAAGAAAGTG GAAGACGTAA
37101 GACCTGAAAC TGTTAGTCCA ACACTAAAGA GTGGTATCAG ATAATCCCAA
37151 CACCATAGCT CTGCACCAGG CTTAAAGTAA CCAGCTCGAA TTTGAGCAGA
37201 AGTAAGAAAA GATTGTGTGT ATGTGTATGT GTATGTGTGT ATGTGTGTGT
37251 GTGTGTGTGT GTGTGTTGAT ATGGTGGAAC AGCTTCAGAG GAAGTAAAAG
37301 AACTAACAAG CTATCTGATG TCCTTGAACA TTAGTAAACA TTATTGTGAG
37351 GTGTTGGTAG ATCTTTTGGA GCATTCAGCA TTTACCAGGT ACATAGAAAA
37401 CTATCCACAT GAAAAAAAGA GTTGTGTTAT TAATTCTAGG AAAGCAAAAA
37451 AAGATTTCTG TAATCCAAAT ATGTTACTTG ACTCTTCAAT TAATAAAATT
37501 TACACACTGG TACTAAATGT AGGCTGTTAA TTTAACCAAA AATAGAGATG
37551 CTATAATGTA AAGATGTGGT GTGGAAAAGT TGCAAAGAAG TTGTAAAACA
37601 ACTAAATCCC TAACTACGTA AGAGAAAATA AATATTTACT GTCTAAACCT
37651 AGAAGCTGTA ATTTGAGCAT ATTATCTAGT GATAAGGAGT TAGATACTAT
37701 AAGAAATCAT TAAACAAGCA TGAAGTGGCT ACCTCTTGGA GAACAGCTTG
37751 CGTGAGGTAA CATGGGACAT AACTGCTTTT CAAGCCTCTT CATGTTTTTT
37801 CGTTTTTGCC TTTTTTAACT AAGTGCTGTT TACTCTAACA AAATAAATTT
37851 TATTTTTTAA ATGTGAAAGT TGAACCTTAA GGCTCTTTGT AATATTAAAA
37901 TCCATGTCTC AATTAATTAT TCTGTGTTGA TAGTCTATAC ATGTACTGTC
37951 TAGTAACAAA ATATGTGATT CATCAAAATA TCTTAAATAA TGAGCTTTAT
38001 GTTTAGCTAA TTTTCTTTCT TTTTTCTTAT GTTTTTATTT TTAGGGTGAT
38051 TCTGGGGGAC CTTTAGTCAC AAGGGATCTG AAAGATACGT GGTATCTCAT
38101 TGGAATTGTA AGCTGGGGAG ATAACTGTGG TCAAAAGGAC AAGCCTGGAG
38151 TCTACACACA AGTGACTTAT TACCGAAACT GGATTGCTTC AAAAACAGGC
38201 ATCTAATTCA CGATAAAAGT TAAACAAAGA AAGCTGTATG CAGGTCATAT
38251 ATGCATGAGA ATTCAACTAT TTAGTGGGTG TAGTACAACA AAGTGATATT
38301 AAATTACTGG ATCTAGTAAC ATGAAACACA CAACGTAAGT TATTTAGAAT
38351 CACTTTAATC AACCAATAAT CCTTAGCCAA TTTATAAGGG ACTTTTATTT
38401 GTAAAGTAAT GGATCTGGCT TGAAAAATAC GGTAGAGATA CTTAGCTCTT
38451 TAAATCACGA ATGTTGAAGT ACCAGTGAGA CTCAATACAT ATTTTTGAAG
38501 ATAGTCCATG GGATTTTTAG AATGTCGTTG TCAAGGGTCT CCTTTTAACT
38551 GAGAAACTTT TTGAACTCAC AAAGTGTTCA AGAAACCCTT GTATAATTCC
38601 CTACATTTCT CTCGAGCTCA CAAATACTTT TTTTTCTTTT TCCTTATTCA
38651 ATCAGATTTT CCAAAGTACC TTTCCACCAT AAGAAATGAA TTTTCTACTT
38701 CTACACCCAT TTGAGAGACA CCAATAAAAG AAAGTCATAT GTAGGAAACA
38751 AAGTCTGATA GTAAAACAAG CCAGAGATCT TCTAACTTTT TTTAGTTATA
38801 AAACCTCTAA TTTTTGGTGA CTTTTCTACA CACACACACA CATA (SEQ ID NO:3)
```

FEATURES:
Start: 3000
Exon: 3000-3093
Intron: 3094-4905

FIGURE 3-17

Exon: 4906-5024
Intron: 5025-17485
Exon: 17486-17553
Intron: 17554-19507
Exon: 19508-19668
Intron: 19669-25382
Exon: 25383-25421
Intron: 25422-26622
Exon: 26623-26794
Intron: 26795-30319
Exon: 30320-30579
Intron: 30580-34817
Exon: 34818-34960
Intron: 34961-38044
Exon: 38045-38203
Stop: 38204

CHROMOSOME MAP POSITION:
Chromosome 4

ALLELIC VARIANTS (SNPs):

| DNA Position | Major | Minor | Domain | Protein Position | Major | Minor |
|---|---|---|---|---|---|---|
| 72 | A | G | Beyond ORF(5') | | | |
| 1894 | C | T | Beyond ORF(5') | | | |
| 1897 | C | T | Beyond ORF(5') | | | |
| 2123 | T | C | Beyond ORF(5') | | | |
| 2124 | G | A | Beyond ORF(5') | | | |
| 2648 | A | C | Beyond ORF(5') | | | |
| 2805 | A | T | Beyond ORF(5') | | | |
| 4036 | A | G | Intron | | | |
| 5056 | - | A | Intron | | | |
| 5445 | C | T | Intron | | | |
| 5608 | T | C | Intron | | | |
| 6243 | G | A | Intron | | | |
| 6273 | C | G | Intron | | | |
| 6294 | A | G | Intron | | | |
| 6312 | A | G | Intron | | | |
| 6506 | C | - | Intron | | | |
| 6714 | C | G | Intron | | | |
| 6815 | G | C | Intron | | | |
| 6994 | A | G | Intron | | | |
| 12478 | T | C | Intron | | | |
| 13493 | T | G A C | Intron | | | |
| 13522 | C | G A T | Intron | | | |

FIGURE 3-18

| | | | | | | |
|---|---|---|---|---|---|---|
| 13916 | T | C | Intron | | | |
| 13974 | A | G | Intron | | | |
| 15081 | G | A | Intron | | | |
| 15907 | A | G | Intron | | | |
| 17884 | G | A | Intron | | | |
| 17908 | G | T | Intron | | | |
| 20551 | T | C G | Intron | | | |
| 21222 | G | T A | Intron | | | |
| 21232 | G | A T | Intron | | | |
| 21353 | C | T A | Intron | | | |
| 21904 | C | T A | Intron | | | |
| 22132 | T | C G | Intron | | | |
| 22369 | T | A G C | Intron | | | |
| 22742 | - | G | Intron | | | |
| 22882 | C | T | Intron | | | |
| 23316 | A | - | Intron | | | |
| 23867 | A | G C | Intron | | | |
| 23954 | A | G | Intron | | | |
| 26548 | G | A | Intron | | | |
| 26573 | T | A G C | Intron | | | |
| 27400 | A | G C | Intron | | | |
| 27788 | G | - | Intron | | | |
| 28069 | T | G A | Intron | | | |
| 29269 | C | G | Intron | | | |
| 29537 | C | A | Intron | | | |
| 29726 | T | G C | Intron | | | |
| 30496 | C | T A | Exon | 277 | P | L Q |
| 30695 | A | C G | Intron | | | |
| 30752 | T | G C | Intron | | | |
| 30849 | A | T | Intron | | | |
| 30900 | G | A | Intron | | | |
| 30904 | G | T | Intron | | | |
| 31664 | T | C | Intron | | | |
| 32014 | T | C G | Intron | | | |
| 32197 | A | G | Intron | | | |
| 33074 | - | T | Intron | | | |
| 33505 | C | T A | Intron | | | |
| 33551 | A | T | Intron | | | |
| 33801 | C | A G T | Intron | | | |
| 34648 | T | C G | Intron | | | |
| 34754 | G | T | Intron | | | |
| 34867 | T | C | Exon | 321 | D | D |
| 35013 | C | T | Intron | | | |
| 35225 | C | A G T | Intron | | | |

FIGURE 3-19

| | | | | |
|---|---|---|---|---|
| 35517 | A | C T | G | Intron |
| 36885 | C | | G | Intron |
| 38527 | G | | A | Beyond ORF(3') |

Context:

DNA
Position

72   TTATATTCATAAAAGTAGGCAGTAAGTTGAAGATTTATTCATATAGGATTTAGTAGCTGC
AGCTTTAACCT
[A,G]
TGGCTTCTGTAGCTTTTGTAATCTGGCAGTGCGCATCTGCTATATTATCTAAATGTTTCC
TCAAAAGGAGAAACACTCTAACAACTTATCACCCTAGTCTGCTGGCCACCATTTTCCCTC
AGATGCTCACAGCTTCTTCCGTGGGATTTGAAGATATGACTTCCATGACACTTGATCAGT
ATGTCAATGGGTATTGAACCACTCTTCAGCTCTGATCCCACGGTTCAGTTCCTTTCAGTG
TGACTATGTGTCTTGGTGGTGGGAGATGTGATTCTTTTATCTACTTTCTCCATTTATCTT

1894   ACCTGGGCCCTTAAACAGATATCCTCTCTCTCATCCTGTGTTATTTCCTGTGTAATGTTG
GTATCATTCCTGCCTGACTCTCATAGATTTATATGATTCCTACTCTGTCCAGGTGCCTTA
TTGGGTCTTAGCGGTAAAAAGATGAACAAGGCTAATGCAGCCCATTGAGAAGCTATCTGT
AAGTGAACATACATGCAAACTAATACTTGATTCAATGTGAGAAGCACTGTTGCTGATCAT
AGGTGCCAGAAGAACAGCAAAGAGTTATTTTTTCCTCCAAAATTGTGGAAAAATTTTTAT
[C,T]
CCCGGTGTGATGCAATATAAAATACACAGCACCACCTTTGAAGTATTCTTGCCAAATGAA
TTTAACCAAAATCTAATCAAGACTTCAGAGCTAAAGAAAATCTAAAGGTAATCCAATTTA
TAGGAAATGAGGGATATAAAAGAACAAGTTAAATAATACCACAGGAAAGCATTCAGACAA
GTCCAGAAAGTAAGATATTCTAAAGGATGTTTAGCTTGATCTCTTCAACAGTCAATGTCA
TTAAAAACTAAAAAAGAAGCAGGACTCTTTTAGATTAAAAGAGATTAAAAAGGCATAACA

1897   TGGGCCCTTAAACAGATATCCTCTCTCTCATCCTGTGTTATTTCCTGTGTAATGTTGGTA
TCATTCCTGCCTGACTCTCATAGATTTATATGATTCCTACTCTGTCCAGGTGCCTTATTG
GGTCTTAGCGGTAAAAAGATGAACAAGGCTAATGCAGCCCATTGAGAAGCTATCTGTAAG
TGAACATACATGCAAACTAATACTTGATTCAATGTGAGAAGCACTGTTGCTGATCATAGG
TGCCAGAAGAACAGCAAAGAGTTATTTTTTCCTCCAAAATTGTGGAAAAATTTTTATCCC
[C,T]
GGTGTGATGCAATATAAAATACACAGCACCACCTTTGAAGTATTCTTGCCAAATGAATTT
AACCAAAATCTAATCAAGACTTCAGAGCTAAAGAAAATCTAAAGGTAATCCAATTTATAG
GAAATGAGGGATATAAAAGAACAAGTTAAATAATACCACAGGAAAGCATTCAGACAAGTC
CAGAAAGTAAGATATTCTAAAGGATGTTTAGCTTGATCTCTTCAACAGTCAATGTCATTA
AAAACTAAAAAAGAAGCAGGACTCTTTTAGATTAAAAGAGATTAAAAAGGCATAACAAAC

2123   TTGCTGATCATAGGTGCCAGAAGAACAGCAAAGAGTTATTTTTTCCTCCAAAATTGTGGA
AAAATTTTTATCCCCGGTGTGATGCAATATAAAATACACAGCACCACCTTTGAAGTATTC
TTGCCAAATGAATTTAACCAAAATCTAATCAAGACTTCAGAGCTAAAGAAAATCTAAAGG
TAATCCAATTTATAGGAAATGAGGGATATAAAAGAACAAGTTAAATAATACCACAGGAAA
GCATTCAGACAAGTCCAGAAAGTAAGATATTCTAAAGGATGTTTAGCTTGATCTCTTCAA

FIGURE 3-20

[T,C]
AGTCAATGTCATTAAAAACTAAAAAAGAAGCAGGACTCTTTTAGATTAAAAGAGATTAAA
AAGGCATAACAAACAAGTGCACTGCATGGTCCTCGATTATGTCTTGGCTTTTACAAATCA
TGTGTAATTATAATGAAACCATGGAGGGAACTTGAAGATGGACTGGGTATTAGATGATAT
GGCAGAAATATCATTAATTTTTTAGGAGTGTTAAGAGTATCATGGTTATGTTGGATATAT
CCTAATTGTCTATAATAATGATTTGGTAAAAAGTCACGATGTTTTATTTCACATTAAAAT

2124  TGCTGATCATAGGTGCCAGAAGAACAGCAAAGAGTTATTTTTTCCTCCAAAATTGTGGAA
AAATTTTTATCCCCGGTGTGATGCAATATAAAATACACAGCACCACCTTTGAAGTATTCT
TGCCAAATGAATTTAACCAAAATCTAATCAAGACTTCAGAGCTAAAGAAAATCTAAAGGT
AATCCAATTTATAGGAAATGAGGGATATAAAAGAACAAGTTAAATAATACCACAGGAAAG
CATTCAGACAAGTCCAGAAAGTAAGATATTCTAAAGGATGTTTAGCTTGATCTCTTCAAC
[G,A]
GTCAATGTCATTAAAAACTAAAAAAGAAGCAGGACTCTTTTAGATTAAAAGAGATTAAAA
AGGCATAACAAACAAGTGCACTGCATGGTCCTCGATTATGTCTTGGCTTTTACAAATCAT
GTGTAATTATAATGAAACCATGGAGGGAACTTGAAGATGGACTGGGTATTAGATGATATG
GCAGAAATATCATTAATTTTTTAGGAGTGTTAAGAGTATCATGGTTATGTTGGATATATC
CTAATTGTCTATAATAATGATTTGGTAAAAAGTCACGATGTTTTATTTCACATTAAAATA

2648  GTTATGTTGGATATATCCTAATTGTCTATAATAATGATTTGGTAAAAAGTCACGATGTTT
TATTTCACATTAAAATATAGCAGCAGAAAAAATAAATGAGCCAAATACAGTAAAATTTTC
AACAATTGATATAATAATGTGATATATATATGGATGTTCAATTATACTATTCTTAGTAAT
TTTTTATGTCTGAACATTTTCATAATACTTAAAAATAAAAGATAAAAGATAAAAATAAAT
GAGATAATAGATTTAAAATCACTTTGTAAACTCTAAAAGGATAGACAGATAAAAGAGATA
[A,C]
CAAAGTGCTGGAGAAAGGAGGAATGGTCCCTTTTCAAGCATGTATGCCACCTTGGACCAT
GCTGCTAAGAGAAACCATTCCTGACCACCACAAAGAGGCCACCAAATGCCTCTAAAATAG
AAAGCAGGAGCAACATTAGGATTCCCAGATCCTGATATTTTTTTTTTAACACATCTTCTC
AGACCAAGATGACATTGAACAAAATTAAAGACCTTTTTGCAGGGAAAGGTAGGCTACAGC
AACTTGAACTTGTCTAAGGAGAGCTGGAAAACCTGCAAGCATTGCTATCTGAGAGTAACC

2805  TCAATTATACTATTCTTAGTAATTTTTTATGTCTGAACATTTTCATAATACTTAAAAATA
AAAGATAAAAGATAAAAATAAATGAGATAATAGATTTAAAATCACTTTGTAAACTCTAAA
AGGATAGACAGATAAAAGAGATAACAAAGTGCTGGAGAAAGGAGGAATGGTCCCTTTTCA
AGCATGTATGCCACCTTGGACCATGCTGCTAAGAGAAACCATTCCTGACCACCACAAAGA
GGCCACCAAATGCCTCTAAAATAGAAAGCAGGAGCAACATTAGGATTCCCAGATCCTGAT
[A,T]
TTTTTTTTTAACACATCTTCTCAGACCAAGATGACATTGAACAAAATTAAAGACCTTTT
TGCAGGGAAAGGTAGGCTACAGCAACTTGAACTTGTCTAAGGAGAGCTGGAAAACCTGCA
AGCATTGCTATCTGAGAGTAACCAGTGGGCCCTTCCTTTTCTCAGGACAGTGGGATTTGG
CACCCGAAGCAGAAATGCTGAAGCCATGGATGATTGCCGTTCTCATTGTGTTGTCCCTGA
CAGTGGTGGCAGTGACCATAGGTCTCCTGGTTCACTTCCTAGTATTTGGTAGGTAAAATT

4036  TTCTGGGGAGAATGCAAGCCATTTACATTTTTTCACAAATCTCTACAATGTGACTCTCAC
ATGGATGTATGTGATAAAACAAATAACTCAGGCTGCTCACTTTAACGCTCTTATCTGCTG
TCACCTTCACAGAGTCAATGGGGGAGCAAAGACTCTACTTGGAGCCTTAAAGGGCTTAAG

FIGURE 3-21

```
        ATCATAGTCCTAGGCCTTATATGATAACCCCAGCTGTAGTTTATACCATTGGCAAAAGAT
        TCTCAGGTCACTTTATTTGGTTGCATAAAAGTCTCTTTACAATGAGAGTAAGGTTTGTTA
        [A,G]
        CAGTATGGATTATATGGGTAAGTAATCAGGATGTCCAAAAATGTATTACAAGGTCCAGAG
        ATTTCCCACTTAAGACATATGCCTTCCTGATATCCCTGTTTCTTTCCTTGGTTTGTAGTC
        TCGAAACCCACTCCCTCTTCCCTGAGCCAGGCTTCTCAAGGATTGAGGTTGTTTTGTATT
        TTTCCCATTCTCTATCTTTAACTCTGTATCTTTCTTACTCCCTCTGGGCCTTACTCCTCA
        GATTACCAAATTCCTTAGGAGTCTCAACTGCTTTCCTTTCTTACATTTCCTAATAGATTT

5056    GATATAAAACATTAACTGTTATTTTTTAAATAAAACTCAATTATGAAGAGGCTCAGGGAC
        ATATTCAAGATTTATATTGGCCCCATTGTAATTGAGTTCTGAAATCTTTGTCCAAACCAT
        TTAGTTTCCTATTTTTCATTTCCATTGCAGACCAAAAAAAGGAGTACTATCATGGCTCCT
        TTAAAATTTTAGATCCACAAATCAATAACAATTTCGGACAAAGCAACACATATCAACTTA
        AGGACTTACGAGAGACGACCGAAAATTTGGTGAGTCAGGTAAACTTCTTTTTATCATAGA
        [-,A]
        TAATGCAAGTGGAAGGGATTTTGTGGATCATTTCTCCATTTCTAAAAACATGATTTTCAG
        ACCGCCAACATTAGAATCATCTTGCAGATTGCTAGGCCCCATCCCAGACCTGCTTAATCA
        GAGTATGATGAGATGGGTAGGTGGGGAGAGGAGAGTAAGGGAATCTGCATGTCTAACAAA
        TGGGTGATTCTAATAAGCCTCTCTTTCTAACTCAGCTACCTTATTTAAAGGTAAGAGAAT
        TGAGGCCAAGATATCCTAGCCCGTTTCTTCCCCAATTCCACCACGTTTCCCCTGTAGAAA

5445    TTGCTAGGCCCCATCCCAGACCTGCTTAATCAGAGTATGATGAGATGGGTAGGTGGGGAG
        AGGAGAGTAAGGGAATCTGCATGTCTAACAAATGGGTGATTCTAATAAGCCTCTCTTTCT
        AACTCAGCTACCTTATTTAAAGGTAAGAGAATTGAGGCCAAGATATCCTAGCCCGTTTCT
        TCCCCAATTCCACCACGTTTCCCCTGTAGAAAAGCCTAATCATACCAAAACTAGTTTTTA
        TAAGTCCACACACTTGTTTGTAAGACCACATTTTAAGATTTTGAGTATTTTCAGAATTTA
        [C,T]
        GTTCATCTTGTAAGTATATTGATAAAGACAAAAAACCAGACTTATTTTGTAGTAATCAAG
        TCAAATGCTAATAATTTTGTTAAAGCTAAAGTGCAAGACTGCTCCCAAAAAGAAAAAAAG
        CACACTCAGTTGTATAATCATTCCACTCAGAATGCCCATGAACTCTCACTCAAAAACTAG
        GTTCAAATTAATTTTTCTAACAAGGAAGCACAGAAGCAGAGACTTATTTTAAAAAGAAAG
        AAATGACAAATGTATTGGTTTGTTTTAATCAAAGAACCATTTTTAAGACACTTTCTTTCC

5608    TATCCTAGCCCGTTTCTTCCCCAATTCCACCACGTTTCCCCTGTAGAAAAGCCTAATCAT
        ACCAAAACTAGTTTTTATAAGTCCACACACTTGTTTGTAAGACCACATTTTAAGATTTTG
        AGTATTTTCAGAATTTACGTTCATCTTGTAAGTATATTGATAAAGACAAAAAACCAGACT
        TATTTTGTAGTAATCAAGTCAAATGCTAATAATTTTGTTAAAGCTAAAGTGCAAGACTGC
        TCCCAAAAAGAAAAAAAGCACACTCAGTTGTATAATCATTCCACTCAGAATGCCCATGAA
        [T,C]
        TCTCACTCAAAAACTAGGTTCAAATTAATTTTTCTAACAAGGAAGCACAGAAGCAGAGAC
        TTATTTTAAAAAGAAAGAAATGACAAATGTATTGGTTTGTTTTAATCAAAGAACCATTTT
        TAAGACACTTTCTTTCCCAAATCATCTACCATTTTTTCCTGTCATCATTTGCTCTTTGTC
        CATAGTATACCTAATGGCATCATATTTACAATAATATTGTAGAGTTTATAATCTCTATTT
        TCAGTTAACATTAAATCATTCACAATTTCTTAATTTTGTGGTTTCATCTTTCCCAACCAA
```

FIGURE 3-22

6243    TTCTTTCACATGCAGAGCATCTTATAAAAGAGCATTTGCAATCAGTTCTTAAGTTATGCT
        AGGATGAACGGGGAGCCTGCACCAATACACCCAAATACCTTCTCTACTCCTCCAGTCCTA
        AGTGACTCCACATAACCTCCTCGATGCAAAAAGAGAAAACTCTTAACTTGCCTTAGTTAA
        AAAGATAAACACACCTTTGAATGATGGAAAATGTTACAATTTACTGGGAAATTTTGAAAT
        TTGTTTCATTTATATTTTATGGCCAACATTACTGCTACTGTTGTTGTAAGTTAACTA
        [G,A]
        GCAATTCTGTCTTTACTGAAGTAAACGGACAAGAATGCAATAGGTCTTAAAAGAAGTGAG
        AGAAATGCAGAGGTGCATGTTGAACAGAAACTCTATTTAAAAGTGGAGTTTTAAGTTTCA
        CCTAAGCATGTGTTCCTTCAAAGGCTAAGGCTAAGTTAAGTAAGGACACATTATCATCAT
        GGGTACCTGCAAGGCCCTTCTCTGGTTGTCATTATTTATTTATCCTCCTTTATCACCATA
        GCATAAGCCCTTACCCTCCCCCCTTGCAGGAAATCATTCTATGTTTCATGTGGTATTCTT

6273    AGCATTTGCAATCAGTTCTTAAGTTATGCTAGGATGAACGGGGAGCCTGCACCAATACAC
        CCAAATACCTTCTCTACTCCTCCAGTCCTAAGTGACTCCACATAACCTCCTCGATGCAAA
        AAGAGAAAACTCTTAACTTGCCTTAGTTAAAAAGATAAACACACCTTTGAATGATGGAAA
        ATGTTACAATTTACTGGGAAATTTTGAAATTTGTTTCATTTATATTTTATGGCCAACATT
        ACTGCTACTGTTGTTGTAAGTTAACTAGGCAATTCTGTCTTTACTGAAGTAAACGGA
        [C,G]
        AAGAATGCAATAGGTCTTAAAAGAAGTGAGAGAAATGCAGAGGTGCATGTTGAACAGAAA
        CTCTATTTAAAAGTGGAGTTTTAAGTTTCACCTAAGCATGTGTTCCTTCAAAGGCTAAGG
        CTAAGTTAAGTAAGGACACATTATCATCATGGGTACCTGCAAGGCCCTTCTCTGGTTGTC
        ATTATTTATTTATCCTCCTTTATCACCATAGCATAAGCCCTTACCCTCCCCCCTTGCAGG
        AAATCATTCTATGTTTCATGTGGTATTCTTTTGTTTGTATTCATTCTTACAAAAATATGT

6294    AGTTATGCTAGGATGAACGGGGAGCCTGCACCAATACACCCAAATACCTTCTCTACTCCT
        CCAGTCCTAAGTGACTCCACATAACCTCCTCGATGCAAAAAGAGAAAACTCTTAACTTGC
        CTTAGTTAAAAAGATAAACACACCTTTGAATGATGGAAAATGTTACAATTTACTGGGAAA
        TTTTGAAATTTGTTTCATTTATATTTTATGGCCAACATTACTGCTACTGTTGTTGTTGTA
        AGTTAACTAGGCAATTCTGTCTTTACTGAAGTAAACGGACAAGAATGCAATAGGTCTTAA
        [A,G]
        AGAAGTGAGAGAAATGCAGAGGTGCATGTTGAACAGAAACTCTATTTAAAAGTGGAGTTT
        TAAGTTTCACCTAAGCATGTGTTCCTTCAAAGGCTAAGGCTAAGTTAAGTAAGGACACAT
        TATCATCATGGGTACCTGCAAGGCCCTTCTCTGGTTGTCATTATTTATTTATCCTCCTTT
        ATCACCATAGCATAAGCCCTTACCCTCCCCCCTTGCAGGAAATCATTCTATGTTTCATGT
        GGTATTCTTTTGTTTGTATTCATTCTTACAAAAATATGTTTTGCTATTTTGCGTACACTT

6312    GGGGAGCCTGCACCAATACACCCAAATACCTTCTCTACTCCTCCAGTCCTAAGTGACTCC
        ACATAACCTCCTCGATGCAAAAAGAGAAAACTCTTAACTTGCCTTAGTTAAAAAGATAAA
        CACACCTTTGAATGATGGAAAATGTTACAATTTACTGGGAAATTTTGAAATTTGTTTCAT
        TTATATTTTATGGCCAACATTACTGCTACTGTTGTTGTTGTAAGTTAACTAGGCAATTCT
        GTCTTTACTGAAGTAAACGGACAAGAATGCAATAGGTCTTAAAAGAAGTGAGAGAAATGC
        [A,G]
        GAGGTGCATGTTGAACAGAAACTCTATTTAAAAGTGGAGTTTTAAGTTTCACCTAAGCAT
        GTGTTCCTTCAAAGGCTAAGGCTAAGTTAAGTAAGGACACATTATCATCATGGGTACCTG
        CAAGGCCCTTCTCTGGTTGTCATTATTTATTTATCCTCCTTTATCACCATAGCATAAGCC

FIGURE 3-23

```
              CTTACCCTCCCCCCTTGCAGGAAATCATTCTATGTTTCATGTGGTATTCTTTTGTTTGTA
              TTCATTCTTACAAAAATATGTTTTGCTATTTTGCGTACACTTGCTTTTAACTTACATTTT

6506     CAACATTACTGCTACTGTTGTTGTTGTAAGTTAACTAGGCAATTCTGTCTTTACTGAAGT
              AAACGGACAAGAATGCAATAGGTCTTAAAAGAAGTGAGAGAAATGCAGAGGTGCATGTTG
              AACAGAAACTCTATTTAAAAGTGGAGTTTTAAGTTTCACCTAAGCATGTGTTCCTTCAAA
              GGCTAAGGCTAAGTTAAGTAAGGACACATTATCATCATGGGTACCTGCAAGGCCCTTCTC
              TGGTTGTCATTATTTATTTATCCTCCTTTATCACCATAGCATAAGCCCTTACCCTCCCCC
              [C,-]
              TTGCAGGAAATCATTCTATGTTTCATGTGGTATTCTTTTGTTTGTATTCATTCTTACAAA
              AATATGTTTTGCTATTTTGCGTACACTTGCTTTTAACTTACATTTTGTGTTATAAATCAC
              TTTTGTTTCATCTCTTTTTACTGAGAACTTTTTAAAAGATATATGTTACTAAATATACCT
              TTAGTTTATTGCTGTTAGCTGCTAATTCATAGTGTGTATCTTCCATATTTACCTGCCTGT
              CATGCCAAGAAATGCCACACTAAACAGACTCCTACTTACCCCCTTATAGACCTATGCAAG

6714     TTATCATCATGGGTACCTGCAAGGCCCTTCTCTGGTTGTCATTATTTATTTATCCTCCTT
              TATCACCATAGCATAAGCCCTTACCCTCCCCCCTTGCAGGAAATCATTCTATGTTTCATG
              TGGTATTCTTTTGTTTGTATTCATTCTTACAAAAATATGTTTTGCTATTTTGCGTACACT
              TGCTTTTAACTTACATTTTGTGTTATAAATCACTTTTGTTTCATCTCTTTTTACTGAGAA
              CTTTTTAAAAGATATATGTTACTAAATATACCTTTAGTTTATTGCTGTTAGCTGCTAATT
              [C,G]
              ATAGTGTGTATCTTCCATATTTACCTGCCTGTCATGCCAAGAAATGCCACACTAAACAGA
              CTCCTACTTACCCCCTTATAGACCTATGCAAGTACTTCTGGAAGCAGAATTACTAGGTCA
              TTGAATGTACATATACTTAACTTGACCAATTGGTGCAGGTTTGCTCTTCAAAATGGCTGA
              CTCAGTGTGCACGCCCATCTACAATGCATGAGGATTTCTATGTCCCCACATCTAACCAAC
              ACTTAGTGTCTTAGTATGTTTAGGCTACTACAACAAAAAATACCATAGGCTGGGTATCTT

6815     AATCATTCTATGTTTCATGTGGTATTCTTTTGTTTGTATTCATTCTTACAAAAATATGTT
              TTGCTATTTTGCGTACACTTGCTTTTAACTTACATTTTGTGTTATAAATCACTTTTGTTT
              CATCTCTTTTTACTGAGAACTTTTTAAAAGATATATGTTACTAAATATACCTTTAGTTTA
              TTGCTGTTAGCTGCTAATTCATAGTGTGTATCTTCCATATTTACCTGCCTGTCATGCCAA
              GAAATGCCACACTAAACAGACTCCTACTTACCCCCTTATAGACCTATGCAAGTACTTCTG
              [G,C]
              AAGCAGAATTACTAGGTCATTGAATGTACATATACTTAACTTGACCAATTGGTGCAGGTT
              TGCTCTTCAAAATGGCTGACTCAGTGTGCACGCCCATCTACAATGCATGAGGATTTCTAT
              GTCCCCACATCTAACCAACACTTAGTGTCTTAGTATGTTTAGGCTACTACAACAAAAAAT
              ACCATAGGCTGGGTATCTTAAACAACAAACAATTATTTCTCATAGTTCTGGAGGCTGAAG
              ATTCCAAGATGAAGATGATCAAGGCTCTAGCAGATGTCTGGTGAGAGCCTGCTTCCTGGT

6994     ATTGCTGTTAGCTGCTAATTCATAGTGTGTATCTTCCATATTTACCTGCCTGTCATGCCA
              AGAAATGCCACACTAAACAGACTCCTACTTACCCCCTTATAGACCTATGCAAGTACTTCT
              GGAAGCAGAATTACTAGGTCATTGAATGTACATATACTTAACTTGACCAATTGGTGCAGG
              TTTGCTCTTCAAAATGGCTGACTCAGTGTGCACGCCCATCTACAATGCATGAGGATTTCT
              ATGTCCCCACATCTAACCAACACTTAGTGTCTTAGTATGTTTAGGCTACTACAACAAAAA
              [A,G]
              TACCATAGGCTGGGTATCTTAAACAACAAACAATTATTTCTCATAGTTCTGGAGGCTGAA
```

FIGURE 3-24

```
              GATTCCAAGATGAAGATGATCAAGGCTCTAGCAGATGTCTGGTGAGAGCCTGCTTCCTGG
              TTCATAGAATACCATCTTGCTGTGTCCCTCATGGCAGAAGCCATAAGAGAACTTTCTTTT
              GTAAGGACACTAATGACTTTCATGAGAACTCCACCCTCATGACCTAACTATCCTCCAAAG
              GCCCCATCTCCTCTATCATCGGTTTGGGAGTTAAGGTCTCAAAATATAAATTTCAGGGGA

12478      TTCTCATTTCCCTGTATCAGTTTTTGGTGAGGAAGGCAAAGGTAGGAGGAACTGTAATAG
              AGAAAGATGAAGGAAGCTGATGGATATATTGACATGTGTATGTACATCTAGTGTGAACAA
              TCTATAGTTGGAAGAAAGGTGTGGATGGGTATGCTTTTTGAGGGAAGTTTTTGAGAAAAG
              AAGTAATATGAACTATTTCTAAATTTCCTGATAAAGTTGTAAATACAGCATAGTCTTCAC
              AGGAGAATCTATTTAGTTTATCATCATCATTCAGCAAATACAGCATGATGTTAGGCACTA
              [T,C]
              AAAAGGCTAAGAAAAATGATTCTCTCTCTCTCATAAACTAATCCAATTTAGAGATTTAGA
              AGACAACAAATCTGGAGAGGACATGAACCTTCTAAATAATGACCTTCCCTTGCTTTGGGT
              ATCCTGGTTTTAAATATTTTTAGTACAGCTTTAAATAGATCCAAATGAGATATTTTCCTC
              TTTTACAAAAGCAATTCAAAGATCTAGGTTTTTGTTGTACACTGAGAATTAATACTTTTT
              TCTTTAAAATCCTTAATTGCAAATCTTTAAATTCTATAAATATTTTGCCTTGTGATCTCA

13493      GATCCAAAAAAAAAAAAAAAAACACCTAGAGTTTTATACAGATATGATACGAACTTAAAAG
              GACTGCACTAAAAACTACCAAGATTATGATTCTTATTTTTGGAGAGTAAAGAAAATAGGC
              TGCCTTTGGAGAGGGGTGCAACAGTTTCTGATCCTCTTACAAACTGCTTGCTGCCCATCA
              GTGGGTAGGAGGTCTTAGTGAGAACCTACCTGCATGCTCATCCTGAGGTAGGCACTGTGA
              AGGCGTTAACAGGCTCTGAAGCTACATGGCCCTGGTTTCAGTGAACTCTGTGGTGTCAAC
              [T,G,A,C]
              TGGGCAAGTCACTTCCTCTTCTATGAAACGTGAATAATCATAGTACTCACCTTAGAGGGC
              TGATTTGAAAGCAAATGAGCTCAAACACAATGACATCTGTGCTTGGTGCATATATGGCAG
              ACAACAGTGATTCCCACTATTATAATTATTACAGTCTTACCAAGGAGGAGCTTTCCACAA
              ATAATCAATTACCTAAAATGTCCAAAAACAGGAAAAAAAAAATCTCTTCCGATAATTCATG
              TGTAATTTTCTTTTTTCTCTAGGAGCATTGATCTCAACCTGATGTAAAGCAAGCACTTTA

13522      GTTTTATACAGATATGATACGAACTTAAAAGGACTGCACTAAAAACTACCAAGATTATGA
              TTCTTATTTTTGGAGAGTAAAGAAAATAGGCTGCCTTTGGAGAGGGGTGCAACAGTTTCT
              GATCCTCTTACAAACTGCTTGCTGCCCATCAGTGGGTAGGAGGTCTTAGTGAGAACCTAC
              CTGCATGCTCATCCTGAGGTAGGCACTGTGAAGGCGTTAACAGGCTCTGAAGCTACATGG
              CCCTGGTTTCAGTGAACTCTGTGGTGTCAACTTGGGCAAGTCACTTCCTCTTCTATGAAA
              [C,G,A,T]
              GTGAATAATCATAGTACTCACCTTAGAGGGCTGATTTGAAAGCAAATGAGCTCAAACACA
              ATGACATCTGTGCTTGGTGCATATATGGCAGACAACAGTGATTCCCACTATTATAATTAT
              TACAGTCTTACCAAGGAGGAGCTTTCCACAAATAATCAATTACCTAAAATGTCCAAAAAC
              AGGAAAAAAAAATCTCTTCCGATAATTCATGTGTAATTTTCTTTTTTCTCTAGGAGCATT
              GATCTCAACCTGATGTAAAGCAAGCACTTTAAAAAGTCTTATAAAATTTTCCTGGTAAAT

13916      AACAGTGATTCCCACTATTATAATTATTACAGTCTTACCAAGGAGGAGCTTTCCACAAAT
              AATCAATTACCTAAAATGTCCAAAAACAGGAAAAAAAAATCTCTTCCGATAATTCATGTG
              TAATTTTCTTTTTTCTCTAGGAGCATTGATCTCAACCTGATGTAAAGCAAGCACTTTAAA
              AAGTCTTATAAAATTTTCCTGGTAAATGCAAAACTTTCTGATAAATAAATTCTCACCTTT
              TTATCAATTTGTTAATTCAACAAAAATATACTACATACCAACAGCATGCAAAGCACTATG
```

FIGURE 3-25

[T,C]
TAGATTTTATAGACTATGAAAAGATAAATTGCCATCTCTATGCATAAAGGGTTTGCCATT
TAATAAAAGAGACTATATATTTGCATAAATATATAGTGAATATATTGCATAAATATATAA
TATATGTTTACATTAAAGAATAAAAGGTATAAGAGGGATAAGAAAAATTGAGACAGAGGG
AAGACAGGTCAGTTTGAGATTAACGAATATCCCCAAAGAAGGTATTATCTGAGATTGGCC
TTGAAGGATAGTTGTGATTCAGGAACACAGAACTTGCAGAATGAGAAGGTTGTTACAGAC

13974    ATAATCAATTACCTAAAATGTCCAAAAACAGGAAAAAAAAATCTCTTCCGATAATTCATG
TGTAATTTTCTTTTTTCTCTAGGAGCATTGATCTCAACCTGATGTAAAGCAAGCACTTTA
AAAAGTCTTATAAAATTTTCCTGGTAAATGCAAAACTTTCTGATAAATAAATTCTCACCT
TTTTATCAATTTGTTAATTCAACAAAAATATACTACATACCAACAGCATGCAAAGCACTA
TGCTAGATTTTATAGACTATGAAAAGATAAATTGCCATCTCTATGCATAAAGGGTTTGCC
[A,G]
TTTAATAAAAGAGACTATATATTTGCATAAATATATAGTGAATATATTGCATAAATATAT
AATATATGTTTACATTAAAGAATAAAAGGTATAAGAGGGATAAGAAAAATTGAGACAGAG
GGAAGACAGGTCAGTTTGAGATTAACGAATATCCCCAAAGAAGGTATTATCTGAGATTGG
CCTTGAAGGATAGTTGTGATTCAGGAACACAGAACTTGCAGAATGAGAAGGTTGTTACAG
ACCAAAGGAACAGCCTGAGAGGCGTGAGTATGCAGGAAAATGAGGGCCATGCCTGAAAGT

15081    AATGGCTGGGCGAGTCTGTTTGTTTGAGTTGACAGCCTCTCCCTCACTCTTTCATTAAAT
ATCCAACTAACCTTCAATTGCCCTCTTGGAACTTAATCTCAGTGTAATTTCCAGCATGTC
AAAATTATCAAGCAGAAAGAGATACTACCCTGAAAGAGGGTCTTTTGTTCAATGCTAGGA
GACAAACTCCAACTACAAAATTCTAGAAATGCCCTAAAGAGAGAGATAGGATAGATTTAC
AAATTGCTAATGCTATTAGGTTGTATAGATAACAATAGATTTATAACAACCTGGCACACA
[G,A]
CTTTAAATATATAAGTTTCTCTGAAACTTCTGGGAACTTGGAATGCCAGAACGTTGGCAA
AAAGAATGCTTCTAATAATGAAAGCCATCATCTGCCATGGAAACAATTTCAGGGTCTTTA
GAAAGCTAGTTTATACATAAGCTCCATTCTACAATAAAACTTATGTTCATGTTTTTTCTG
ATTTTCCTCCTGCTGTAAATTCATTTTATCAGAATTCTTTTTACCAGTCCCTCTGCCCCA
TTTCTCAAAGCGTTGTCCTCAGACTACCTGTATCACCTAAAGATTCTAAGGCCTCCTCCG

15907    AAACTTCATCCAATGCCTTCACCAAAAAGTTACAAATGGCCAGGAATCAAATGTGGTTGA
ACTTATTCAGAGGGTAATTACAAAACAAACTTCTTTAAATACCCAACTGCTATTTGCTTT
TTTCCTTCTAAATTGTATCACTTCTCTCCCTGTTCCATTTTGTTTGCCTTTTTATTTTTT
GGAATCCCTCACCTCCATACTGAGTAGTAGAGCTGGCTGTGGGTGATGAGAGAGAAATTG
TTATAACAAAGTCACCCTTTCAAAAACATGTCTTCCAAAAGAATTTTGTTTCTAGCAGAT
[A,G]
AACCCCACACCACCTCAGCTAAATGGGGCTTTCTTTATTTAAGTACCAATAAAGACATAT
TTTGGATACTAGCAATTTATTTTCCAAATGCTATCTTTGATCTTAAGTTTAAGGCTATTA
CCAAATCTATATCTCTACAAGTTTTATACTTTAGGTCAATAAATTACTTGATAACTTATT
ACTATGTGTTCTACAAAAGAAACCGAAGTAAAATTTACATCACATTTAACAGGGTGGTTG
TGTGATTGAGTGGGAAGAGGCGGACCCTACAGATAGAAGACTTGGGTTTCAGTCCCAGCT

17884    AAGACTGGAGGGAAAAGGAACAAAGGAGACAGGGACTCTCATGTATTGTATGTCTCCATG
GACTAGGCTTTTGGCTAGAATTTTTCATAAACATTACCTTTAAAGCAGTCTTGAAGTATA
GGGCTGACCACCGTTTTGTCAACAAAAAGACTAAGATTCAGGAAGGGTAAGAAATATGTT

FIGURE 3-26

```
          CAAAGTTCACCAACTGACAGTTTCCCAAAGTGACAGAACCAGGAATCAAACCCCATTAAC
          TTATTGTGAGGCCTGGAACCTACCAGAACCCATGACGTGGGGAAAACCCAGCAGCTTGTC
          [G,A]
          TTGCATGCACCAAGTTATATTATGTTGACAATTATATTATTTCAACCACGTTAAGCAGGC
          AAACTTGGCTATAAAATGGGTTCACAAATTTTACCTGTAATGTAACCGAATGACATAAGG
          CATGCCTAAACAAAAAGATATTCCTGTTGTAATAAATTTTCTTTCTGTCATGGTGGAGGG
          GGAAGACTCATATCAGTTGCAGATATTGCTCAGAAGTTTCAATTGTGTTATTTTGAAAAA
          CTACATAGCAGAACACGCATGTCATATACACAAATCCATGAGCCTGTATGACTCATATTT

17908     GGAGACAGGGACTCTCATGTATTGTATGTCTCCATGGACTAGGCTTTTGGCTAGAATTTT
          TCATAAACATTACCTTTAAAGCAGTCTTGAAGTATAGGGCTGACCACCGTTTTGTCAACA
          AAAAGACTAAGATTCAGGAAGGGTAAGAAATATGTTCAAAGTTCACCAACTGACAGTTTC
          CCAAAGTGACAGAACCAGGAATCAAACCCCATTAACTTATTGTGAGGCCTGGAACCTACC
          AGAACCCATGACGTGGGGAAAACCCAGCAGCTTGTCGTTGCATGCACCAAGTTATATTAT
          [G,T]
          TTGACAATTATATTATTTCAACCACGTTAAGCAGGCAAACTTGGCTATAAAATGGGTTCA
          CAAATTTTACCTGTAATGTAACCGAATGACATAAGGCATGCCTAAACAAAAAGATATTCC
          TGTTGTAATAAATTTTCTTTCTGTCATGGTGGAGGGGGAAGACTCATATCAGTTGCAGAT
          ATTGCTCAGAAGTTTCAATTGTGTTATTTTGAAAAACTACATAGCAGAACACGCATGTCA
          TATACACAAATCCATGAGCCTGTATGACTCATATTTCTTAAAGATAAAGAAAAATAATAT

20551     ATTATACCATTATCACTTCCCTCAATTAAGGAGAACAAACCTTTATCAAGGTCTATCTCT
          ATGGCCTTTACCTTAAGTAACTAATTTCTTTTTATATTCCAGTGACGTACGCAAATTCAC
          CTTTATAGAAGTGAAATTCACACAAAAAGAGTTGAGGAATTCAGTAATTAAAAGGAGCTA
          AGAATCAAATTTAAATCTCTAATTTCTTAAAAGGCTCCAATTAAAAAAGGTTTCTATAGT
          CAAACACATCTTAAAAATTCTGGCTTTGATACTCGTTTCTTGGAAATTCTTCCTTATAGT
          [T,C,G]
          TCATATTAAAAATTCTAAGGCAGCCAGCTAGAGAGAAACTTGTTTACCCTCGTCCGCTAA
          GCTGTTTGCACAGCATCTTCTTCCAACAGACAAGTATAGATTTCTCCTACAAATTTCAAT
          GGATACCAGACCTAAGTGTTACAGAAGAGATTCAGGGCAAGCGATTTTTATCAGACATGA
          AACAGGACACTCTGCCCTTGTAAGGGTCTAGCTGACACTTCAAGAGGAAACCAGATAAGG
          AAGTAAAAAATGTGAGGTAATGGAATGGGCAGATGTTTGCTGATGTGAGAACGAGTCAGC

21222     TCTTTGTTAGATGGGGAAGCAAATGAATAGAAGTTGTGAAACAATGGGCATTCTGATAAT
          TTACATGATGCTTTCTGTGTAATTTCCAATAAATAGTTAATTTGTCAGGAATGTAAAAGC
          CTGAACTATCTGAAACCAGAGTAAAGCATAAATTGTTCATTGGCTGCCTGGTCTTTTTGT
          TTTTTGTAGGCTCAGCTTCTAAACTTCAGCTTATTTTAATAATTGTACTAAATTAAATGG
          TAGGATATGCTAATGGAGAACCTGATTTGAGAGTCACCTGAGGCTGGGCATGGTGGCTCA
          [G,T,A]
          GCCTATAATTCCAGCACTTTGGGAGGCCGAGGCGGGTGGATCACCTGAGGTCAGGAGTTC
          AAGACCAGCCTGGCCAATATGGTGAAACCCCGTCTCTTCTAAAAATACAAAATATTAGTC
          AGGCCTGGTGACGGGCACCTGTAATCCCAGCTACTTGGGAGACTGAGGGGGAAGAATCAC
          TTGAACCCGGGAGGCGGAGGTTGCAGTGAGCCAAGATCGCGCCACTGCACTCAAGCCTGG
          GCTTGACAGAGCAAGACTCCATCTCCAAAAAAATAAAAAATAAAAGAGTTACCTGACCAA
```

FIGURE 3-27

| | |
|---|---|
| 21232 | ATGGGGAAGCAAATGAATAGAAGTTGTGAAACAATGGGCATTCTGATAATTTACATGATG<br>CTTTCTGTGTAATTTCCAATAAATAGTTAATTTGTCAGGAATGTAAAAGCCTGAACTATC<br>TGAAACCAGAGTAAAGCATAAATTGTTCATTGGCTGCCTGGTCTTTTTGTTTTTTGTAGG<br>CTCAGCTTCTAAACTTCAGCTTATTTTAATAATTGTACTAAATTAAATGGTAGGATATGC<br>TAATGGAGAACCTGATTTGAGAGTCACCTGAGGCTGGGCATGGTGGCTCAAGCCTATAAT<br>[G,A,T]<br>CCAGCACTTTGGGAGGCCGAGGCGGGTGGATCACCTGAGGTCAGGAGTTCAAGACCAGCC<br>TGGCCAATATGGTGAAACCCCGTCTCTTCTAAAAAATACAAAATATTAGTCAGGCCTGGTG<br>ACGGGCACCTGTAATCCCAGCTACTTGGGAGACTGAGGGGGAAGAATCACTTGAACCCGG<br>GAGGCGGAGGTTGCAGTGAGCCAAGATCGCGCCACTGCACTCAAGCCTGGGCTTGACAGA<br>GCAAGACTCCATCTCCAAAAAAATAAAAAATAAAAGAGTTACCTGACCAATTCTAACTCC |
| 21353 | GAAACCAGAGTAAAGCATAAATTGTTCATTGGCTGCCTGGTCTTTTTGTTTTTTGTAGGC<br>TCAGCTTCTAAACTTCAGCTTATTTTAATAATTGTACTAAATTAAATGGTAGGATATGCT<br>AATGGAGAACCTGATTTGAGAGTCACCTGAGGCTGGGCATGGTGGCTCAAGCCTATAATT<br>CCAGCACTTTGGGAGGCCGAGGCGGGTGGATCACCTGAGGTCAGGAGTTCAAGACCAGCC<br>TGGCCAATATGGTGAAACCCCGTCTCTTCTAAAAAATACAAAATATTAGTCAGGCCTGGTG<br>[C,T,A]<br>CGGGCACCTGTAATCCCAGCTACTTGGGAGACTGAGGGGGAAGAATCACTTGAACCCGGG<br>AGGCGGAGGTTGCAGTGAGCCAAGATCGCGCCACTGCACTCAAGCCTGGGCTTGACAGAG<br>CAAGACTCCATCTCCAAAAAAATAAAAAATAAAAGAGTTACCTGACCAATTCTAACTCCA<br>CTAAGTCACCACAGGACCACCCAAATAATTGGCTCATGCCTTTGTCTTCATTTTCTCATC<br>TGTAAAATTCCAATGGTAATGTTTGTTCTTCCTGAAATCACAGAGAGATTATAACGATAT |
| 21904 | CAATGGTAATGTTTGTTCTTCCTGAAATCACAGAGAGATTATAACGATATACAAGGAAAT<br>AGAAAACACAATGTGAAATAAAGAGGCTGTTACTAATGAGAAAACTATTATGTTGTGCAT<br>ATGCTTTGGAAACCTGAAATCATTAATTTGAGTGATTGACTAGTAGCAGAAAGATAGATC<br>CTTGAAAGTTTCAGAATGTTCAATGTAGAAAGAACAGTGTTTGTTAGTGATATGGGAGCC<br>TAGGGGGTGTTGCTTTTCTGGCCAGAAACCTCTGTGGCCAGTGGTTGGTGCCTTTGCCCA<br>[C,T,A]<br>GTTTTGCTCTGGCCCACTGGGCTTGTTCTGCCCACTTGACCTGGCAGACTGTGCCCACCT<br>TCCGCTACCAGCCTGGATCCCATGCCCACCAAGGCCAACCCAGGCATGGAGCTGTGAGGG<br>TTGTCTGAGCGAGCACAGGGTCTGGCCACTGCCCACAGCCAGGCACACTGGCTGCAGCAT<br>GACGGGCAGCTCCAGGCACTGGCACAGGTGTGCTGTCTCTCTGTGAGGCTGTGGCTGGAC<br>AAAGCTCACTGCAAGCAGCTTCCCTGGCAGGCACCTGGGAATGTGGTGGCACCCAGGAAG |
| 22132 | GATATGGGAGCCTAGGGGGTGTTGCTTTTCTGGCCAGAAACCTCTGTGGCCAGTGGTTGG<br>TGCCTTTGCCCAAGTTTTGCTCTGGCCCACTGGGCTTGTTCTGCCCACTTGACCTGGCAG<br>ACTGTGCCCACCTTCCGCTACCAGCCTGGATCCCATGCCCACCAAGGCCAACCCAGGCAT<br>GGAGCTGTGAGGGTTGTCTGAGCGAGCACAGGGTCTGGCCACTGCCCACAGCCAGGCACA<br>CTGGCTGCAGCATGACGGGCAGCTCCAGGCACTGGCACAGGTGTGCTGTCTCTCTGTGAG<br>[T,C,G]<br>CTGTGGCTGGACAAAGCTCACTGCAAGCAGCTTCCCTGGCAGGCACCTGGGAATGTGGTG<br>GCACCCAGGAAGCTTGGAGATGCCAGGAACTGCAGGGTCCCAAAGAGGGAGTCACAACCC<br>TGGCTTGGGGAGCTCCCAGGTCTGGGATCCCTAAAGGGCTGCAGCTTTTCTCTCTTTTTA |

FIGURE 3-28

```
          CCCACAATGTGGCCAGCAAGGGGTATGTTTCATTCCTGTTTGTGTTACAGCTCTTTTAGT
          CTTGCTATTTGGCAGGTCCTGAGTTCTTGTCCTGAGACCAAGAAGAATGAGGTATGCAGA

22369     ACACTGGCTGCAGCATGACGGGCAGCTCCAGGCACTGGCACAGGTGTGCTGTCTCTCTGT
          GAGGCTGTGGCTGGACAAAGCTCACTGCAAGCAGCTTCCCTGGCAGGCACCTGGGAATGT
          GGTGGCACCCAGGAAGCTTGGAGATGCCAGGAACTGCAGGGTCCCAAAGAGGGAGTCACA
          ACCCTGGCTTGGGGAGCTCCCAGGTCTGGGATCCCTAAAGGGCTGCAGCTTTTCTCTCTT
          TTTACCCACAATGTGGCCAGCAAGGGGTATGTTTCATTCCTGTTTGTGTTACAGCTCTTT
          [T,A,G,C]
          AGTCTTGCTATTTGGCAGGTCCTGAGTTCTTGTCCTGAGACCAAGAAGAATGAGGTATGC
          AGACAAGTGGAGGGTGAGCAAGACGAAGAAAGGTTTACTGAGCAAGAGAACAGCTCACAG
          GAGACCCACAGTGGGCAGCTCCTCTTCATAGCCAGGGTGTCCCAACAAGTGTCCAGCTCC
          TAGCAAAGAGGAGGCCCTGGAGGTAGAAGCTCCTCTCTGCAGGCAGGTTGTCCTGTTGAG
          TGTTCAGCTTTCAGCACACAGTAGGCAGTAGGCCCTAGAGTGGTCTATCTCCTCTCTGCA

22742     GGTGAGCAAGACGAAGAAAGGTTTACTGAGCAAGAGAACAGCTCACAGGAGACCCACAGT
          GGGCAGCTCCTCTTCATAGCCAGGGTGTCCCAACAAGTGTCCAGCTCCTAGCAAAGAGGA
          GGCCCTGGAGGTAGAAGCTCCTCTCTGCAGGCAGGTTGTCCTGTTGAGTGTTCAGCTTTC
          AGCACACAGTAGGCAGTAGGCCCTAGAGTGGTCTATCTCCTCTCTGCAGGCAGGTAGTCC
          CATGGTCTCCCAGTCACCTCTCCATCTGCAAGGGTCCAATGCTGCCTCCAGCACCTCTCT
          [-,G]
          CCCACCCCTCCGTGCCTGACCAAGCTGCTCCCCCACCAGTGGGCAACTCAGCCCAGCCCC
          ATTGTGGTAGCTCCCAGGGTGGCAGGCTCTGGGGGGCTCCCAGGGATGGGCTCCAAGGAC
          TGTCCACCTTCTCCCCACGCCCTCCCTGCAGTGGCCATGGTCAAGAATGGCAATGTGGGG
          CCAGGTTCCGGAGCAGGAGAGGCTCCAGGCCTGGGAGCAGGTCCTGCCTGGTCACGTGAG
          GTTGGGGGTGGCACAGTCGGCTGCCTCAGGGATGTGGGACACAGGGGACCCACCACCATC

22882     CTCTCTGCAGGCAGGTTGTCCTGTTGAGTGTTCAGCTTTCAGCACACAGTAGGCAGTAGG
          CCCTAGAGTGGTCTATCTCCTCTCTGCAGGCAGGTAGTCCCATGGTCTCCCAGTCACCTC
          TCCATCTGCAAGGGTCCAATGCTGCCTCCAGCACCTCTCTGCCCACCCCTCCGTGCCTGA
          CCAAGCTGCTCCCCCACCAGTGGGCAACTCAGCCCAGCCCCATTGTGGTAGCTCCCAGGG
          TGGCAGGCTCTGGGGGGCTCCCAGGGATGGGCTCCAAGGACTGTCCACCTTCTCCCCACG
          [C,T]
          CCTCCCTGCAGTGGCCATGGTCAAGAATGGCAATGTGGGGCCAGGTTCCGGAGCAGGAGA
          GGCTCCAGGCCTGGGAGCAGGTCCTGCCTGGTCACGTGAGGTTGGGGGTGGCACAGTCGG
          CTGCCTCAGGGATGTGGGACACAGGGGACCCACCACCATCACTGCTACTCCCGCATCCGC
          TCCTGCTACCACTGCTCCAGACAGCCTGTAGCTGCCATCACTAGCACTTAAGAAAGGCAC
          ATTCAGTGGACAGCTCAGGAAAATCTTTACGTCAATTTTTTTATAGGCAAAAACATTGTTT

23316     GTGGGACACAGGGGACCCACCACCATCACTGCTACTCCCGCATCCGCTCCTGCTACCACT
          GCTCCAGACAGCCTGTAGCTGCCATCACTAGCACTTAAGAAAGGCACATTCAGTGGACAG
          CTCAGGAAAATCTTTACGTCAATTTTTTTATAGGCAAAAACATTGTTTCCTGGGCAAACAA
          AATTTATGGACTACCAATAAATAGAAAACTGTAGAGATTCTAGATTAAGTCTAGAAATAA
          TCCTGTAGCCCAAGATTTATTTATAATTTGTCAAGAATCTGTATTTTGTTTTGACAAAAA
          [A,-]
          AAAACTGTGTGGTGTGGGTCCTTCAGGAGACACAGTGTGACAAAGCAAAGCTAAAATCAA
```

FIGURE 3-29

```
           CTTCTTTGCATTGCAAACACCAAGGCTGTAGTCAAGCAGCTCACTGCCTATGTGTCAGAT
           GACTTTGCTTCATTTTTCATCATGATACTTGTAGTCTATAGAGCCCTGAATATTAACTAG
           CTTTCTCCCAACTCAGAACCGTGTTAGGAGGTGGTTGCTTTCAAAACTAAAGTGTTAATG
           TTTATTTCCATTTCTATACCAGGAAAGTAAAAATCTTTGGTCAAAATTAGAAATCTTTAA

23867    TTTCTATACCAGGAAAGTAAAAATCTTTGGTCAAAATTAGAAATCTTTAACAACTAGTTA
           CTTGTGTATTGACAGTTTGTTTCCAGGTGTAATCATTCTCCCTTAAAATCCGGTTATATT
           CACGACCATTATACTTATCCTGGTATCATTCCTGGAAATGGCTAACTTGCATCCTGCTCA
           GACTAAGTTGACAAAGTTTCAATTGAAGAATTCTAACTTTATGCTATTTTCCACTTTATT
           GCATTACAAAGGACAAAATATATAGTTTTCTTAAAAATGAAATAAATTTACTGCCTTAAA
           [A,G,C]
           TACATTTGACGGTAAACTGAGTTCCTTCCATAGAATAACCACTAACAGCAATCGATGGTC
           CTGAGCAATTGACTCTTCACCATACAATGATTTGGGATGCCTTTAAGGGTATATTTGAAT
           TGAATATTTTCAAAAGCTCCCACTTTGTAGAGTTTATCATCACTAGTTTCCCCAGTGGAA
           TTTGTAGAAAGTTAGTAGAATGAAACAATCTTATTTTGTATAATGAGGAATAGAATACTG
           AGAATGTGTCTGAGAAACATGGCACTGGTAGGAAAAAGTAAACAGTTTATTCTCATCTGC

23954    TGTAATCATTCTCCCTTAAAATCCGGTTATATTCACGACCATTATACTTATCCTGGTATC
           ATTCCTGGAAATGGCTAACTTGCATCCTGCTCAGACTAAGTTGACAAAGTTTCAATTGAA
           GAATTCTAACTTTATGCTATTTTCCACTTTATTGCATTACAAAGGACAAAATATATAGTT
           TTCTTAAAAATGAAATAAATTTACTGCCTTAAACTACATTTGACGGTAAACTGAGTTCCT
           TCCATAGAATAACCACTAACAGCAATCGATGGTCCTGAGCAATTGACTCTTCACCATACA
           [A,G]
           TGATTTGGGATGCCTTTAAGGGTATATTTGAATTGAATATTTTCAAAAGCTCCCACTTTG
           TAGAGTTTATCATCACTAGTTTCCCCAGTGGAATTTGTAGAAAGTTAGTAGAATGAAACA
           ATCTTATTTTGTATAATGAGGAATAGAATACTGAGAATGTGTCTGAGAAACATGGCACTG
           GTAGGAAAAAGTAAACAGTTTATTCTCATCTGCTCAATAAGCTAAGTCATTTTAACTTGA
           AAATCATCAAAATTTTCATGAAACCTTCCACCAACTTTATTTTTTCCCCAGCTTTAGTAAG

26548    AGTGCCAGAAATTAGACCAGGAGTTGGTGGTACCATTGTGAATAAAACATGATCCCTGCT
           CTAAAATTAGAATTCCAAAGTAGAGAAAGATATAAATAAATCAGGAAGTATGAAAATAAT
           GTGATTAATGCTATGACAGAGGAAGTGCATAGTGCTATGAGAGTTGATCAGAGAGTCAGC
           TAACCTGTTCTCACACAGTAAGAAAGTGAACCCTGAAATGTGAGAGAGAAGAGGCCATGA
           ATCCAGTGACAGGTGGGGTAAGTGTCCTGGGCAGGAGGAGTAGTATACGAAAATGTCTTC
           [G,A]
           GGCAAGTAAGAATGGGGTCATTTCCTGTAATTACAAGATGTTTCTTATAACTTAATGATC
           TCATCTTTTTTCAGGTTGTGGTAAACGAGTTGTTCCATTAAACGTCAACAGAATAGCATC
           TGGAGTCATTGCACCCAAGGCGGCCTGGCCTTGGCAAGCTTCCCTTCAGTATGATAACAT
           CCATCAGTGTGGGGCCACCTTGATTAGTAACACATGGCTTGTCACTGCAGCACACTGCTT
           CCAGAAGTAAGTTATTGACCTTAAGTTAGAACCCACTTCTGCTAAAAAGCCCTGAGTTTT

26573    GGTGGTACCATTGTGAATAAAACATGATCCCTGCTCTAAAATTAGAATTCCAAAGTAGAG
           AAAGATATAAATAAATCAGGAAGTATGAAAATAATGTGATTAATGCTATGACAGAGGAAG
           TGCATAGTGCTATGAGAGTTGATCAGAGAGTCAGCTAACCTGTTCTCACACAGTAAGAAA
           GTGAACCCTGAAATGTGAGAGAGAAGAGGCCATGAATCCAGTGACAGGTGGGGTAAGTGT
           CCTGGGCAGGAGGAGTAGTATACGAAAATGTCTTCAGGCAAGTAAGAATGGGGTCATTTC
```

FIGURE 3-30

[T,A,G,C]
TGTAATTACAAGATGTTTCTTATAACTTAATGATCTCATCTTTTTTCAGGTTGTGGTAAA
CGAGTTGTTCCATTAAACGTCAACAGAATAGCATCTGGAGTCATTGCACCCAAGGCGGCC
TGGCCTTGGCAAGCTTCCCTTCAGTATGATAACATCCATCAGTGTGGGGCCACCTTGATT
AGTAACACATGGCTTGTCACTGCAGCACACTGCTTCCAGAAGTAAGTTATTGACCTTAAG
TTAGAACCCACTTCTGCTAAAAAGCCCTGAGTTTTGTCATATTCTTGGTAACAATTAATG

27400   TAATCTTTTGTCAAACAATGCTCTCCACTTAAAACTAGTGTCTGTTTCTGCCAAACACTT
        GGGCCAGTCTCATACTGATCTTAAATAATCAAACTAATTCCAAAGTAAAATGGAAATTTT
        CAATAAATGCCGGAAGTTGGTAACCGTGATGATGGAGAACTGCAGATCAAATTTAGAGCA
        TTGACATATCAAGATCTGTGGAATCAGAACAGTTTACAACCAAAATGAGAGATTGCTAGC
        ATGATAAAGACAGGCACTTCAAAAGAGATTCCTCGGAGTATCAAAGGATTCATAGAGGCC
        [A,G,C]
        TTGGGCCACTCAATGTGACCTTCCCATAATAGAGCATCTCTTCACAATAGTGACACAAAA
        GACAAAGCTGAAGTGAAGAATAGCAAATTGTGCTATCCTATAATTGTTTCTGAATGCATA
        CATTTTATTAAATATATGATTAAATGACTTTTTATAACTTTTAATCTTACTTTTCAAGAT
        AATAACCAGTCATTTTTATCACTATTACATTTAGAATTTTAGATTTGTTTCTAAGTAGAT
        TAACTGTATCGCCTTTCTTCTTCATTGCCAATTATTACAGTAATAACAAAGACTTCTTGA

27788   TTGTGCTATCCTATAATTGTTTCTGAATGCATACATTTTATTAAATATATGATTAAATGA
        CTTTTTATAACTTTTAATCTTACTTTTCAAGATAATAACCAGTCATTTTTATCACTATTA
        CATTTAGAATTTTAGATTTGTTTCTAAGTAGATTAACTGTATCGCCTTTCTTCTTCATTG
        CCAATTATTACAGTAATAACAAAGACTTCTTGAGTATCTCTATATAATAGGTGGCAGCAG
        GATTTAGTGGGAAAAATATGTCCCAGGCAGTTGGAGAGCTGGGCAAATTATTGAACCTTA
        [G,-]
        TGTATTAGGTAATAGATAGGCTAGATCTTTTCACATTCTTTTTGACCTATAAAATTCTAA
        CTTTTGTTACTATAATAAATTTCATTTGCCTAGGAGCATAAATCTTTATAGAGACTCTTA
        ATATTCCAAAGAATATACATATTAAGAATCTAGGCTTGGCATGGTGGCTCATGCCTGTAA
        TCCCAGCATTTTGGGAGGCCGAGGCAAGAGGACCACTTGAGCTCAGGAGTTCAAGACCAG
        CTTGGGCAAGATAGTGAAACCCCATTGGGCATGGTGGTGCATACCTATCATCCCAGCTAC

28069   GGCAAATTATTGAACCTTAGTGTATTAGGTAATAGATAGGCTAGATCTTTTCACATTCTT
        TTTGACCTATAAAATTCTAACTTTTGTTACTATAATAAATTTCATTTGCCTAGGAGCATA
        AATCTTTATAGAGACTCTTAATATTCCAAAGAATATACATATTAAGAATCTAGGCTTGGC
        ATGGTGGCTCATGCCTGTAATCCCAGCATTTTGGGAGGCCGAGGCAAGAGGACCACTTGA
        GCTCAGGAGTTCAAGACCAGCTTGGGCAAGATAGTGAAACCCCATTGGGCATGGTGGTGC
        [T,G,A]
        TACCTATCATCCCAGCTACTTGGGAGGCTAACGCAGGAGGATCCCTTAAGCCCAGGAGTT
        TGAGGCTCCTGCAAGCTATGATTGCACCACTGCACTCCAGCCTGAGTGACAATGCAAGAC
        CCCATCTTAAAAAAATAGTAATATATTTTTAAAAATAATCTACATAAATTCTTAATGTTT
        GAAAGATGTGAGAGCTCAGTAAGCTGATATATTAGAAAGCCAGAAATCCCTTATGCTGGT
        GTCTGGTTTTTCAAAGTAATGGGAAACTTACTTTGCCAAAGTTAGCCATTTTTGTGGTAG

29269   CATATATGTGTGTGTGTATATATAAAAAAAAATATATATATATATATATATATATAATTA
        CCTCATTTTTCCAGAACCAACTTCCAGATGCCCTACCACATTGGTTCTTATTCTCTGAAC
        ATTCGAGACTTTGTCAGTGTCTTCCTTAAAATATGCTTCCAATAACTAAATACACCAAGA

FIGURE 3-31

```
         CAGATGTGTGACTAGTGTCACACATAACAAAATAAAGCAGGAAGTCTTCTGAAAAATACA
         AATAATGTAAATTGGTGGGAGACAGTGTTTTATAAAGGGAAGAGCAGAGAGAGGCAGGCA
         [C,G]
         ATATGTGATGTGAATCAAATAGTTTAACCTATCCAGGCTTTATTTTCCTTAAGTATAAAA
         CACAGTCTTTACTAGATGATCTTTCATTGCTACTAAATGATTTTTCCGATTCCTGTATGT
         ACCATAATCCACCCATTGCCCAAGCCCACAAGCTAGAAGTCAACCGCATTTACCACATTT
         GATCATCTCTCAAAGGACTATGCAGTCATCTAATAGACTTTACCACATCCATTCTTGACC
         TTCAAGAATCTACTCCCCAGAAAGAACAAACATGTTTTTTAAAAATGTAAATGAGACTAC

29537    TTTATAAAGGGAAGAGCAGAGAGAGGCAGGCAGATATGTGATGTGAATCAAATAGTTTAA
         CCTATCCAGGCTTTATTTTCCTTAAGTATAAAACACAGTCTTTACTAGATGATCTTTCAT
         TGCTACTAAATGATTTTTCCGATTCCTGTATGTACCATAATCCACCCATTGCCCAAGCCC
         ACAAGCTAGAAGTCAACCGCATTTACCACATTTGATCATCTCTCAAAGGACTATGCAGTC
         ATCTAATAGACTTTACCACATCCATTCTTGACCTTCAAGAATCTACTCCCCAGAAAGAAC
         [C,A]
         AACATGTTTTTTAAAAATGTAAATGAGACTACATTATTCTCTGGCTTAATTATCCAGTAG
         ATTCCCATATCACTTCAATAAAATTTAAGCACTTTATCATGACCTATAAAACACTCTAAA
         ATCTAGTCCCTGCTTACCTCTCCAAGCTCACCCCCAACCATTCTTTCCCTTGTGTTCTGA
         CTGCAGCCCATCCAACCCAAGACCTTGGGATTTTTGCCTGGAAACTTGTTTCCCTCATCT
         CCTCACACTGACCCTCTTTTACTATGTCTTAGCCCAAATGCGTTATCAAAATAATCATAA

29726    AAGTCAACCGCATTTACCACATTTGATCATCTCTCAAAGGACTATGCAGTCATCTAATAG
         ACTTTACCACATCCATTCTTGACCTTCAAGAATCTACTCCCCAGAAAGAACAAACATGTT
         TTTTAAAAATGTAAATGAGACTACATTATTCTCTGGCTTAATTATCCAGTAGATTCCCAT
         ATCACTTCAATAAAATTTAAGCACTTTATCATGACCTATAAAACACTCTAAAATCTAGTC
         CCTGCTTACCTCTCCAAGCTCACCCCCAACCATTCTTTCCCTTGTGTTCTGACTGCAGCC
         [T,G,C]
         ATCCAACCCAAGACCTTGGGATTTTTGCCTGGAAACTTGTTTCCCTCATCTCCTCACACT
         GACCCTCTTTTACTATGTCTTAGCCCAAATGCGTTATCAAAATAATCATAATGACCTGTT
         AGTACTCTATTCCGTTACCCTATTTTATTTTGTTCATAGCCTTTATCAATGTTTAAGATT
         ATTTATCTATTTGTTTGCTTGCTTTGATCCTTTTCCTTCTCTGGAATCTTATACTCCTGT
         GAGCAGGCACCTTAGGTCCTGTTCATCACTTTATCCCCAGCAGTTCAGATAAGGCTCAGC

30496    AACTATAACTGCAGCCAAGTATTCTCAGGATTGTATTTCTCTTATATTAGCCTAAATGCA
         ATTAATCTAGCTCATATACTTTGGGCAGCTTATATATATTCTGTTAATTTCTAACCTTTT
         CCAGGTATAAAAATCCACATCAATGGACTGTTAGTTTTGGAACAAAAATCAACCCTCCCT
         TAATGAAAAGAAATGTCAGAAGATTTATTATCCATGAGAAGTACCGCTCTGCAGCAAGAG
         AGTACGACATTGCTGTTGTGCAGGTCTCTTCCAGAGTCACCTTTTCGGATGACATACGCC
         [C,T,A]
         GATTTGTTTGCCAGAAGCCTCTGCATCCTTCCAACCAAATTTGACTGTCCACATCACAGG
         ATTTGGAGCACTTTACTATGGTGGTGGGTATCTCAGGATAGCTAACAGAGCGCTAAGCCC
         TGTCTAAGGCAATGTGATTTCATCTCCATCAATATTATCCTGACAGCCATTTCCACACAG
         TCTGGTTGGATTAGTTAGGGTTCTTACTTTGTGTGACAGAAATTCAATTCACATTAACCA
         GTGCAGAATAAAAAACAAAGAAACAAAAACTTCCACAAATTTGGCTCATGTAATTTGGAA
```

FIGURE 3-32

30695  AAGATTTATTATCCATGAGAAGTACCGCTCTGCAGCAAGAGAGTACGACATTGCTGTTGT
GCAGGTCTCTTCCAGAGTCACCTTTTCGGATGACATACGCCAGATTTGTTTGCCAGAAGC
CTCTGCATCCTTCCAACCAAATTTGACTGTCCACATCACAGGATTTGGAGCACTTTACTA
TGGTGGTGGGTATCTCAGGATAGCTAACAGAGCGCTAAGCCCTGTCTAAGGCAATGTGAT
TTCATCTCCATCAATATTATCCTGACAGCCATTTCCACACAGTCTGGTTGGATTAGTTAG
[A,C,G]
GTTCTTACTTTGTGTGACAGAAATTCAATTCACATTAACCAGTGCAGAATAAAAAACAAA
GAAACAAAAACTTCCACAAATTTGGCTCATGTAATTTGGAAGTCAAAAAAGTGTAGTAAG
TTTCACTTCAGACACAGGGGTTTATATGATGTCATCTGGCTCTGTGTCTCTGAATTTGAA
TTTTTTGCCCCTTCTTTTCTCTATGTTGGCTTCATTCAGAGGGATGCTAGCTTCACCTAG
TGTCAGAGGTGGCTAACAACACCTCAACACATCATCCTCAACAAAGAAAAAATACATAGA

30752  TGTGCAGGTCTCTTCCAGAGTCACCTTTTCGGATGACATACGCCAGATTTGTTTGCCAGA
AGCCTCTGCATCCTTCCAACCAAATTTGACTGTCCACATCACAGGATTTGGAGCACTTTA
CTATGGTGGTGGGTATCTCAGGATAGCTAACAGAGCGCTAAGCCCTGTCTAAGGCAATGT
GATTTCATCTCCATCAATATTATCCTGACAGCCATTTCCACACAGTCTGGTTGGATTAGT
TAGGGTTCTTACTTTGTGTGACAGAAATTCAATTCACATTAACCAGTGCAGAATAAAAAA
[T,G,C]
AAAGAAACAAAAACTTCCACAAATTTGGCTCATGTAATTTGGAAGTCAAAAAAGTGTAGT
AAGTTTCACTTCAGACACAGGGGTTTATATGATGTCATCTGGCTCTGTGTCTCTGAATTT
GAATTTTTTGCCCCTTCTTTTCTCTATGTTGGCTTCATTCAGAGGGATGCTAGCTTCACC
TAGTGTCAGAGGTGGCTAACAACACCTCAACACATCATCCTCAACAAAGAAAAAATACAT
AGAAAGGAATATTTATTTCTTTTCTTTGCCAGAATTCACATTAATTTCTATTGTTCCAGC

30849  ATCACAGGATTTGGAGCACTTTACTATGGTGGTGGGTATCTCAGGATAGCTAACAGAGCG
CTAAGCCCTGTCTAAGGCAATGTGATTTCATCTCCATCAATATTATCCTGACAGCCATTT
CCACACAGTCTGGTTGGATTAGTTAGGGTTCTTACTTTGTGTGACAGAAATTCAATTCAC
ATTAACCAGTGCAGAATAAAAAACAAAGAAACAAAAACTTCCACAAATTTGGCTCATGTA
ATTTGGAAGTCAAAAAAGTGTAGTAAGTTTCACTTCAGACACAGGGGTTTATATGATGTC
[A,T]
TCTGGCTCTGTGTCTCTGAATTTGAATTTTTTGCCCCTTCTTTTCTCTATGTTGGCTTCA
TTCAGAGGGATGCTAGCTTCACCTAGTGTCAGAGGTGGCTAACAACACCTCAACACATCA
TCCTCAACAAAGAAAAAATACATAGAAAGGAATATTTATTTCTTTTCTTTGCCAGAATTC
ACATTAATTTCTATTGTTCCAGCTGTGTCTAGGAGGACTCAGATTGAGTGGCTAACTCAA
ATATTCTTTATGCCTATGTAGCAAAATTTGCTTCAGTACTGAAGAAGCTAATTTAAGTGT

30900  AACAGAGCGCTAAGCCCTGTCTAAGGCAATGTGATTTCATCTCCATCAATATTATCCTGA
CAGCCATTTCCACACAGTCTGGTTGGATTAGTTAGGGTTCTTACTTTGTGTGACAGAAAT
TCAATTCACATTAACCAGTGCAGAATAAAAAACAAAGAAACAAAAACTTCCACAAATTTG
GCTCATGTAATTTGGAAGTCAAAAAAGTGTAGTAAGTTTCACTTCAGACACAGGGGTTTA
TATGATGTCATCTGGCTCTGTGTCTCTGAATTTGAATTTTTTGCCCCTTCTTTTCTCTAT
[G,A]
TTGGCTTCATTCAGAGGGATGCTAGCTTCACCTAGTGTCAGAGGTGGCTAACAACACCTC
AACACATCATCCTCAACAAAGAAAAAATACATAGAAAGGAATATTTATTTCTTTTCTTTG
CCAGAATTCACATTAATTTCTATTGTTCCAGCTGTGTCTAGGAGGACTCAGATTGAGTGG

FIGURE 3-33

```
        CTAACTCAAATATTCTTTATGCCTATGTAGCAAAATTTGCTTCAGTACTGAAGAAGCTAA
        TTTAAGTGTGATGGTGAATAAGAATAGTGTAGAGATAAATTGTCAAACTATTTGTCCCCT

30904   GAGCGCTAAGCCCTGTCTAAGGCAATGTGATTTCATCTCCATCAATATTATCCTGACAGC
        CATTTCCACACAGTCTGGTTGGATTAGTTAGGGTTCTTACTTTGTGTGACAGAAATTCAA
        TTCACATTAACCAGTGCAGAATAAAAAACAAAGAAACAAAAACTTCCACAAATTTGGCTC
        ATGTAATTTGGAAGTCAAAAAAGTGTAGTAAGTTTCACTTCAGACACAGGGGTTTATATG
        ATGTCATCTGGCTCTGTGTCTCTGAATTTGAATTTTTTGCCCCTTCTTTTCTCTATGTTG
        [G,T]
        CTTCATTCAGAGGGATGCTAGCTTCACCTAGTGTCAGAGGTGGCTAACAACACCTCAACA
        CATCATCCTCAACAAAGAAAAAATACATAGAAAGGAATATTTATTTCTTTTCTTTGCCAG
        AATTCACATTAATTTCTATTGTTCCAGCTGTGTCTAGGAGGACTCAGATTGAGTGGCTAA
        CTCAAATATTCTTTATGCCTATGTAGCAAAATTTGCTTCAGTACTGAAGAAGCTAATTTA
        AGTGTGATGGTGAATAAGAATAGTGTAGAGATAAATTGTCAAACTATTTGTCCCCTCTAA

31664   TGAGAAAATGCAAAAGGGCTTTCTGAGAATGACTAAATCTATTTGCAGGATTCTATACAA
        TTTATTTACATACAAGAAATTATAAAGAATAAGCTTTTGATTCTCAGTCTACCATTAAGG
        AACTAGGAATAACCTTTCACTCACATAGGCAGGAATCGGTTTTAGGGTCTCTAGATTTTT
        TCCAGATGTCCCATGTGGTTTTGTTTTATCTTATACAGAGTGAGACATGCATTGCTTTCT
        TTAAGGTTGTATTACCAATCACAGAAAATATTACCTATGGTTTATTAATTCTAGTAGATC
        [T,C]
        AGTGCTGCTGTAAGCCTGACACCTCCCTAGGTCTGCACTCTCTTGGATGGATTTTCTCTG
        AAGATAGGGCTTGCATTCTCTGCTTCATAGTGGTGGGAAAGACATCACAAATCCCCTTTG
        GCTTGGTGGGAAAAATCACTTTCAGGAGTTTGAGACTGGCACAGAAACATACCTGTCATA
        ATGCGCTGTGAGTGGCAACAGAATCTGACACTTATAGAGCACTCCACCCTACTTGAACAC
        GGCCTCTCTTGGTGAGTGACCCACAGGTGCTTTTAATCTATTAAATAGATTAAATTAACC

32014   GATTTTCTCTGAAGATAGGGCTTGCATTCTCTGCTTCATAGTGGTGGGAAAGACATCACA
        AATCCCCTTTGGCTTGGTGGGAAAAATCACTTTCAGGAGTTTGAGACTGGCACAGAAACA
        TACCTGTCATAATGCGCTGTGAGTGGCAACAGAATCTGACACTTATAGAGCACTCCACCC
        TACTTGAACACGGCCTCTCTTGGTGAGTGACCCACAGGTGCTTTTAATCTATTAAATAGA
        TTAAATTAACCTATCATTCTTAATCTGTTAAGTACATTAATAGATTAAAAGCAGCCATTC
        [T,C,G]
        TTACTCACCAAGAGAGGCTATATTCAAGTCTGTAAAGCAAACCTTAAGAAGTTTTTTAAA
        ATTGAAATTGTACAAAGTATATTCTCTGATCATAATGGAATCTAACTAGACATCAGTAAC
        AGAAAGATAACATAAAAATCCCCAAATGCTTACCAATTAAAAAACATATGTAAATAAAGA
        GAATATCTCGAAGAAATTTGTAAAAACAAATAGAACTAAATGAAAACAAAAATATATAAA
        TATATGCCAGATGCTGCTAAAATAGTGTAGAAAGGGAAATTTATAGAAAATGCATATTAT

32197   TTGAACACGGCCTCTCTTGGTGAGTGACCCACAGGTGCTTTTAATCTATTAAATAGATTA
        AATTAACCTATCATTCTTAATCTGTTAAGTACATTAATAGATTAAAAGCAGCCATTCGTT
        ACTCACCAAGAGAGGCTATATTCAAGTCTGTAAAGCAAACCTTAAGAAGTTTTTTAAAAT
        TGAAATTGTACAAAGTATATTCTCTGATCATAATGGAATCTAACTAGACATCAGTAACAG
        AAAGATAACATAAAAATCCCCAAATGCTTACCAATTAAAAAACATATGTAAATAAAGAGA
        [A,G]
        TATCTCGAAGAAATTTGTAAAAACAAATAGAACTAAATGAAAACAAAAATATATAAATAT
```

FIGURE 3-34

ATGCCAGATGCTGCTAAAATAGTGTAGAAAGGGAAATTTATAGAAAATGCATATTATAAG
GAAAGATATCAAATCAATAATTAAGTTCTCACTTCAAGAAACTAGAAAAATAAAAAATAA
ACCTAAAACAAACATAAGGAAGGAAATAATAAGAATAAGAATAGAAATGAATAAAATTAA
AAATAAACTATAGAAAATTGATAAATAAAAAGCTGATTATTTGATAAAATCAATATTTTG

33074　TCGGCTCACTGCAAACTCCGCCTCCCGGGTTCACGCCATTCTCCTGCCTCAGCCTCCCGA
GTAGCTGGGACTGCAGGCGCCCACCACCATGCCCGGCTAATTGTTTTGTAGTTTTAGTAA
AGAAGGGGTTTCACCGTGTTAGCCAGGATGGTTTTGATCTCCTGACCTCGTGATCCACCT
GCCTCGGCCTCCCAAAGTGCTGGGATTACAGGCGTGAGCCACCGCGCGCCAGGCCATGAA
TGTTTTTAATTGATGATATAGTAGGCAATATAAATGTGTGTGTGTGTGTGTGTGTGTGTG
[-,T]
ATAATATATATAAACCAATTGTATTCAAATAACAGAATAATTTGAAAAATCTCTTAGCAT
ATTTCTGAGTTACACACTTAAATCTTCCGAGCACTTTTAAATATGTGTTTACAAACATTT
CTTCAGAAATAAATCTTGGAAATCGTCTTCTAAAGAAACTGGTGTATTAGGGTTTTTTCA
AATGTACTTAGTTTTTTTTTTAATTGATGTATAAAATTGCATGTACTTACCATGTGCAAC
ATAATGTGTTGAAGTATAGTATATGTACACTGTGAGTGTTAAATCTAGTTAACTAAGAAG

33505　AAATCTTGGAAATCGTCTTCTAAAGAAACTGGTGTATTAGGGTTTTTTCAAATGTACTTA
GTTTTTTTTTTAATTGATGTATAAAATTGCATGTACTTACCATGTGCAACATAATGTGTT
GAAGTATAGTATATGTACACTGTGAGTGTTAAATCTAGTTAACTAAGAAGCGTCTTATTT
TACATAATTATCATTTTTGTGGCAAGAACACTTAATATCTACTCTTGTAGCGTTTCTCAA
GAATACGATATATCAACAGTAGGCAACCAGAAGCTGGGGGTCTTTACAGGGGAAGGAGTT
[C,T,A]
GGGAGATGCTGGTCAACAAATTCATATTTGCAGTTAGGAAGAAAAAGTTCAAGAGATCTC
TCATCCATCATGGTGACTATAGCTGATGATATATCGTATTCTTGTATTAGTTTTTTATAA
ATGTGTAACAAATAATCACAAACAGTTAAAACAGCACTCATTTATTTTTATCTCACTGTT
TTCATGAGTCAGACGTTCAGACACAGCTTAGTTGAGTCCTCTTCTCAGGGTCTCACCAAA
CTGTAATCAAGGTGTCAGCTGGGGTTGTGGCCACATCTGTGGCTCCTTTGAAGGTCTCCT

33551　TTCAAATGTACTTAGTTTTTTTTTTAATTGATGTATAAAATTGCATGTACTTACCATGTG
CAACATAATGTGTTGAAGTATAGTATATGTACACTGTGAGTGTTAAATCTAGTTAACTAA
GAAGCGTCTTATTTTACATAATTATCATTTTTGTGGCAAGAACACTTAATATCTACTCTT
GTAGCGTTTCTCAAGAATACGATATATCAACAGTAGGCAACCAGAAGCTGGGGGTCTTTA
CAGGGGAAGGAGTTAGGGAGATGCTGGTCAACAAATTCATATTTGCAGTTAGGAAGAAAA
[A,T]
GTTCAAGAGATCTCTCATCCATCATGGTGACTATAGCTGATGATATATCGTATTCTTGTA
TTAGTTTTTTATAAATGTGTAACAAATAATCACAAACAGTTAAAACAGCACTCATTTATT
TTTATCTCACTGTTTTCATGAGTCAGACGTTCAGACACAGCTTAGTTGAGTCCTCTTCTC
AGGGTCTCACCAAACTGTAATCAAGGTGTCAGCTGGGGTTGTGGCCACATCTGTGGCTCC
TTTGAAGGTCTCCTCAAGGTTTGCTGGCAGAATTCCTTTACTCGCAGCTGTAGAATGCAT

33801　AGTTAGGGAGATGCTGGTCAACAAATTCATATTTGCAGTTAGGAAGAAAAAGTTCAAGAG
ATCTCTCATCCATCATGGTGACTATAGCTGATGATATATCGTATTCTTGTATTAGTTTTT
TATAAATGTGTAACAAATAATCACAAACAGTTAAAACAGCACTCATTTATTTTTATCTCA
CTGTTTTCATGAGTCAGACGTTCAGACACAGCTTAGTTGAGTCCTCTTCTCAGGGTCTCA
CCAAACTGTAATCAAGGTGTCAGCTGGGGTTGTGGCCACATCTGTGGCTCCTTTGAAGGT

FIGURE 3-35

[C,A,G,T]
TCCTCAAGGTTTGCTGGCAGAATTCCTTTACTCGCAGCTGTAGAATGCATGCCAGCTTGC
TGCTTTAACTCTTTAGGAAAGTGTCTCAACTCCAGCAAGGCTCGCCCTTTTTGAAATGGC
TCAGCTGATTAGGTCAGGCCCACCTTTGATAATCTCCTTTTGATGAATTCAAAGTCAAAC
TCATTAGAGGTCTTAATCGCATCTGTAAAATTCCCTCATCTTGGCCATATAACATAACCT
AATCATGAGAATGGCATCCCTCATATTCACAGATCCTGCCCATATTTGGGAGGAGGGGAA

34648   TATATGTATATTTCACATATATCTTATATATGTGAAAGCTCATCATAAACTTTAAATAAT
AAAATAAATGTACATAGTATTATAGGCATTTTATCAAGCCAATGGAGAAAACCATCTAGG
CATGCAGAGTTTCTGGGAACAATCTGGAACCCACAAATAAAAGCTTTACAAAAGATAAAA
GGCCTTCCTGAAATATATAAGCTGATTATTTTTAAGGTTAGATTTTACCAGGAAAAAGAA
TCCAAATGGCTTTCTTGCTTTGAGAAGTTTTTATAAAAATGTGATTGGACAATAATTATC
[T,C,G]
TTAGATGTGCCAGATTTAACCAGAAATTCTTTTTTCTAGAAACTGCTTATATTAACTTCA
TTCTGTATTGACAATTTTACCATGAAAAAAATATTAGGAAAGTCTTCTCACTTCACTCTA
GCCAAAGATGCTGATTGTAAATACTAGAATAACTCTATTTTTCCTTAAGGGGAATCCCAA
AATGATCTCCGAGAAGCCAGAGTGAAAATCATAAGTGACGATGTCTGCAAGCAACCACAG
GTGTATGGCAATGATATAAAACCTGGAATGTTCTGTGCCGGATATATGGAAGGAATTTAT

34754   GAAAACCATCTAGGCATGCAGAGTTTCTGGGAACAATCTGGAACCCACAAATAAAAGCTT
TACAAAAGATAAAAGGCCTTCCTGAAATATATAAGCTGATTATTTTTAAGGTTAGATTTT
ACCAGGAAAAAGAATCCAAATGGCTTTCTTGCTTTGAGAAGTTTTTATAAAAATGTGATT
GGACAATAATTATCGTTAGATGTGCCAGATTTAACCAGAAATTCTTTTTTTCTAGAAACTG
CTTATATTAACTTCATTCTGTATTGACAATTTTACCATGAAAAAAATATTAGGAAAGTCT
[G,T]
CTCACTTCACTCTAGCCAAAGATGCTGATTGTAAATACTAGAATAACTCTATTTTTCCTT
AAGGGGAATCCCAAAATGATCTCCGAGAAGCCAGAGTGAAAATCATAAGTGACGATGTCT
GCAAGCAACCACAGGTGTATGGCAATGATATAAAACCTGGAATGTTCTGTGCCGGATATA
TGGAAGGAATTTATGATGCCTGCAGGGTAAGTTGGAGGGATTTTTTTATATTACTAACTC
AAAAATTTGTATCTGGCTTAGAATATATTATATGTTCTTTACATAAGGACAAAACATAGA

34867   AGATTTTACCAGGAAAAAGAATCCAAATGGCTTTCTTGCTTTGAGAAGTTTTTATAAAAA
TGTGATTGGACAATAATTATCGTTAGATGTGCCAGATTTAACCAGAAATTCTTTTTTCTA
GAAACTGCTTATATTAACTTCATTCTGTATTGACAATTTTACCATGAAAAAAATATTAGG
AAAGTCTTCTCACTTCACTCTAGCCAAAGATGCTGATTGTAAATACTAGAATAACTCTAT
TTTTCCTTAAGGGGAATCCCAAAATGATCTCCGAGAAGCCAGAGTGAAAATCATAAGTGA
[T,C]
GATGTCTGCAAGCAACCACAGGTGTATGGCAATGATATAAAACCTGGAATGTTCTGTGCC
GGATATATGGAAGGAATTTATGATGCCTGCAGGGTAAGTTGGAGGGATTTTTTTATATTA
CTAACTCAAAAATTTGTATCTGGCTTAGAATATATTATATGTTCTTTACATAAGGACAAA
ACATAGATATCATGTCAGCTCAAAAAAGTTACAAATGCAAATTTCACAGCACAAATACT
TTTAAATGTTTTATTAAGATAAATGAAGTAAGAGTTTCTCTGATGCTATCAAACAAACAA

35013   GTATTGACAATTTTACCATGAAAAAAATATTAGGAAAGTCTTCTCACTTCACTCTAGCCA
AAGATGCTGATTGTAAATACTAGAATAACTCTATTTTTCCTTAAGGGGAATCCCAAAATG
ATCTCCGAGAAGCCAGAGTGAAAATCATAAGTGACGATGTCTGCAAGCAACCACAGGTGT

FIGURE 3-36

ATGGCAATGATATAAAACCTGGAATGTTCTGTGCCGGATATATGGAAGGAATTTATGATG
CCTGCAGGGTAAGTTGGAGGGATTTTTTTATATTACTAACTCAAAAATTTGTATCTGGCT
[C,T]
AGAATATATTATATGTTCTTTACATAAGGACAAAACATAGATATCATGTCAGCTCAAAAA
AGTTACAAATGCAAATTTCACAGCACAAAATACTTTTAAATGTTTTATTAAGATAAATGA
AGTAAGAGTTTCTCTGATGCTATCAAACAAACAAAATTAGAATTTCTTAACCAGAAATCC
AAAGATTAATAAAGCAGTTTATTTTCTCAAGCGGCTCACATTCAAGAAAGAAAATAATCA
TAAACAGAGAAGTATAAAGTGATGTTATGAATAATATAATGAAAAGCAAATATTTTTCTT

35225    GCCGGATATATGGAAGGAATTTATGATGCCTGCAGGGTAAGTTGGAGGGATTTTTTTATA
TTACTAACTCAAAAATTTGTATCTGGCTTAGAATATATTATATGTTCTTTACATAAGGAC
AAAACATAGATATCATGTCAGCTCAAAAAAGTTACAAATGCAAATTTCACAGCACAAAAT
ACTTTTAAATGTTTTATTAAGATAAATGAAGTAAGAGTTTCTCTGATGCTATCAAACAAA
CAAAATTAGAATTTCTTAACCAGAAATCCAAAGATTAATAAAGCAGTTTATTTTCTCAAG
[C,A,G,T]
GGCTCACATTCAAGAAAGAAAATAATCATAAACAGAGAAGTATAAAGTGATGTTATGAAT
AATATAATGAAAAGCAAATATTTTTCTTGAAGGAAACATTTTTGGAACAAGTATCAGAGA
GATGAGACGTAAATAAGGCCTGAAGAATAAATAACATCCAATTTCAGAATAAGAAAATAA
TGTTATAGAAAAGACAAAAAGCATAGCCAAAATTATGAAGGTGTGAAATTACAATTCATA
TCTGAGGGAACTCCAAGTAATTGGTTGGGTCTCAGCATGAGGAGGATGAGAAGAGAAACA

35517    TTCTCAAGCGGCTCACATTCAAGAAAGAAAATAATCATAAACAGAGAAGTATAAAGTGAT
GTTATGAATAATATAATGAAAAGCAAATATTTTTCTTGAAGGAAACATTTTTGGAACAAG
TATCAGAGAGATGAGACGTAAATAAGGCCTGAAGAATAAATAACATCCAATTTCAGAATA
AGAAAATAATGTTATAGAAAAGACAAAAAGCATAGCCAAAATTATGAAGGTGTGAAATTA
CAATTCATATCTGAGGGAACTCCAAGTAATTGGTTGGGTCTCAGCATGAGGAGGATGAGA
[A,C,T,G]
GAGAAACAAGTAGATAACCATGAGAAGGTGGATTAGGCCATGTTGTGATTCCATGGGCCC
TCCCCAGTGCCCTCATCTGCCTTCTAACATGGATGTTTTCCAGCGAAGGTACGTTTCTTC
CTGGAGACACTTGCTTTTTAACATGAGATACTTTAGAACTCTAAGGAGGCCACTCTATGT
GGAAATGATGGAATGGTATTGATATCAGGTGGCAGAAAGTCCTGTCCAGAGTCCCACAAA
CTGTACCACATGTGCGACCTCTATCAGAAAAGGAGCAGGGACCTATGTGACATAGAGGCT

36885    TAAGAAAACTAGAGGATAAGCTCAGGAGATCCAACACCAAATGAATAGGAGCTCTGAAAA
CATAAAACGCGAGTGTACAATATAAAAAAAAATAAAGAATGCTCCTAGTTCTGAAGCTTA
CATGCATCCTATTGAAGAAAAGGTCCAAGTAGTGCTGGGCACAATAAATGAAGTACTTCT
TTCCAAGACATACCATCATAAAGGGTCAGAAGCCAGGGATAAGGAGAACAATCTTAAAAC
TTTGAAGGAAGAACCATCAGAACTACATAGAACTCCTCAACAGTAACTCTAGAAGGTAGA
[C,G]
GATGGTGGAAAACACATTCAAATTTCAAAGGGAAGATTATTTCAACCTAGATTCCTACCC
ATGCTAACTAAATATCAACTGTGAGGGTGGAATTAAGAAGTTTAGACAAGCAATGACTGA
AAAAAATGTACTTCTGATACCCTACTTCTTAGGAAACTACTTGAGAGGGTACCTCAGCAA
AATGAGGGAATAAATCAAGAAAGTGGAAGACGTAAGACCTGAAACTGTTAGTCCAACACT
AAAGAGTGGTATCAGATAATCCCAACACCATAGCTCTGCACCAGGCTTAAAGTAACCAGC

FIGURE 3-37

38527  AAGAAAGCTGTATGCAGGTCATATATGCATGAGAATTCAACTATTTAGTGGGTGTAGTAC
AACAAAGTGATATTAAATTACTGGATCTAGTAACATGAAACACACAACGTAAGTTATTTA
GAATCACTTTAATCAACCAATAATCCTTAGCCAATTTATAAGGGACTTTTATTTGTAAAG
TAATGGATCTGGCTTGAAAAATACGGTAGAGATACTTAGCTCTTTAAATCACGAATGTTG
AAGTACCAGTGAGACTCAATACATATTTTTGAAGATAGTCCATGGGATTTTTAGAATGTC
[G,A]
TTGTCAAGGGTCTCCTTTTAACTGAGAAACTTTTTGAACTCACAAAGTGTTCAAGAAACC
CTTGTATAATTCCCTACATTTCTCTCGAGCTCACAAATACTTTTTTTCTTTTTCCTTAT
TCAATCAGATTTTCCAAAGTACCTTTCCACCATAAGAAATGAATTTTCTACTTCTACACC
CATTTGAGAGACACCAATAAAAGAAAGTCATATGTAGGAAACAAAGTCTGATAGTAAAAC
AAGCCAGAGATCTTCTAACTTTTTTTAGTTATAAAACCTCTAATTTTTGGTGACTTTTCT

FIGURE 3-38

SEQUENCE LISTING

```
<160> NUMBER OF SEQ ID NOS: 4

<210> SEQ ID NO 1
<211> LENGTH: 1225
<212> TYPE: DNA
<213> ORGANISM: Homo sapien

<400> SEQUENCE: 1
cgcccttatg ctgaagccat ggatgattgc cgttctcatt gtgttgtccc tgacagtggt    60
ggcagtgacc ataggtctcc tggttcactt cctagtattt gaccaaaaaa aggagtacta   120
tcatggctcc tttaaaattt tagatccaca aatcaatttc aatttcggac aaagcaacac   180
atatcaactt aaggacttac gagagacgac cgaaaatttg gtggatgaga tatttataga   240
ttcagcctgg aagaaaaatt atatcaagaa ccaagtagtc agactgactc cagaggaaga   300
tggtgtgaaa gtagatgtca ttatggtgtt ccagttcccc tctactgaac aaagggcagt   360
```

```
aagagagaag aaaatccaaa gcatcttaaa tcagaagata aggaatttaa gagccttgcc      420
aataaatgcc tcatcagttc aagttaatgc aatgagctca tcaacagggg agttaactgt      480
ccaagcaagt tgtggtaaac gagttgttcc attaaacgtc aacagaatag catctggagt      540
cattgcaccc aaggcggcct ggccttggca agcttccctt cagtatgata acatccatca      600
gtgtggggcc accttgatta gtaacacatg gcttgtcact gcagcacact gcttccagaa      660
gtataaaaat ccacatcaat ggactgttag ttttggaaca aaaatcaacc ctcccttaat      720
gaaaagaaat gtcagaagat ttattatcca tgagaagtac cgctctgcag caagagagta      780
cgacattgct gttgtgcagg tctcttccag agtcaccttt tcggatgaca tacgccggat      840
ttgtttgcca gaagcctctg catccttcca accaaatttg actgtccaca tcacaggatt      900
tggagcactt tactatggtg gggaatccca aaatgatctc cgagaagcca gagtgaaaat      960
cataagtgac gatgtctgca agcaaccaca ggtgtatggc aatgatataa aacctggaat     1020
gttctgtgcc ggatatatgg aaggaattta tgatgcctgc aggggtgatt ctgggggacc     1080
tttagtcaca agggatctga agatacgtg tatctcatt ggaattgtaa gctggggaga     1140
taactgtggt caaaaggaca agcctggagt ctacacacaa gtgacttatt accgaaactg     1200
gattgcttca aaaacaggca tctaa                                          1225
```

<210> SEQ ID NO 2
<211> LENGTH: 405
<212> TYPE: PRT
<213> ORGANISM: Homo sapien

<400> SEQUENCE: 2

```
Met Leu Lys Pro Trp Met Ile Ala Val Leu Ile Val Leu Ser Leu Thr
  1               5                  10                  15

Val Val Ala Val Thr Ile Gly Leu Leu Val His Phe Leu Val Phe Asp
             20                  25                  30

Gln Lys Lys Glu Tyr Tyr His Gly Ser Phe Lys Ile Leu Asp Pro Gln
         35                  40                  45

Ile Asn Phe Asn Phe Gly Gln Ser Asn Thr Tyr Gln Leu Lys Asp Leu
     50                  55                  60

Arg Glu Thr Thr Glu Asn Leu Val Asp Glu Ile Phe Ile Asp Ser Ala
 65                  70                  75                  80

Trp Lys Lys Asn Tyr Ile Lys Asn Gln Val Val Arg Leu Thr Pro Glu
                 85                  90                  95

Glu Asp Gly Val Lys Val Asp Val Ile Met Val Phe Gln Phe Pro Ser
            100                 105                 110

Thr Glu Gln Arg Ala Val Arg Glu Lys Lys Ile Gln Ser Ile Leu Asn
        115                 120                 125

Gln Lys Ile Arg Asn Leu Arg Ala Leu Pro Ile Asn Ala Ser Ser Val
    130                 135                 140

Gln Val Asn Ala Met Ser Ser Ser Thr Gly Glu Leu Thr Val Gln Ala
145                 150                 155                 160

Ser Cys Gly Lys Arg Val Pro Leu Asn Val Asn Arg Ile Ala Ser
                165                 170                 175

Gly Val Ile Ala Pro Lys Ala Ala Trp Pro Trp Gln Ala Ser Leu Gln
            180                 185                 190

Tyr Asp Asn Ile His Gln Cys Gly Ala Thr Leu Ile Ser Asn Thr Trp
        195                 200                 205

Leu Val Thr Ala Ala His Cys Phe Gln Lys Tyr Lys Asn Pro His Gln
```

```
                210                 215                 220
Trp Thr Val Ser Phe Gly Thr Lys Ile Asn Pro Leu Met Lys Arg
225                 230                 235                 240

Asn Val Arg Arg Phe Ile Ile His Glu Lys Tyr Arg Ser Ala Ala Arg
                245                 250                 255

Glu Tyr Asp Ile Ala Val Val Gln Val Ser Ser Arg Val Thr Phe Ser
                260                 265                 270

Asp Asp Ile Arg Arg Ile Cys Leu Pro Glu Ala Ser Ala Ser Phe Gln
            275                 280                 285

Pro Asn Leu Thr Val His Ile Thr Gly Phe Gly Ala Leu Tyr Tyr Gly
        290                 295                 300

Gly Glu Ser Gln Asn Asp Leu Arg Glu Ala Arg Val Lys Ile Ile Ser
305                 310                 315                 320

Asp Asp Val Cys Lys Gln Pro Gln Val Tyr Gly Asn Asp Ile Lys Pro
                325                 330                 335

Gly Met Phe Cys Ala Gly Tyr Met Glu Gly Ile Tyr Asp Ala Cys Arg
                340                 345                 350

Gly Asp Ser Gly Gly Pro Leu Val Thr Arg Asp Leu Lys Asp Thr Trp
            355                 360                 365

Tyr Leu Ile Gly Ile Val Ser Trp Gly Asp Asn Cys Gly Gln Lys Asp
        370                 375                 380

Lys Pro Gly Val Tyr Thr Gln Val Thr Tyr Tyr Arg Asn Trp Ile Ala
385                 390                 395                 400

Ser Lys Thr Gly Ile
            405

<210> SEQ ID NO 3
<211> LENGTH: 38844
<212> TYPE: DNA
<213> ORGANISM: Homo sapien

<400> SEQUENCE: 3
ttatattcat aaaagtaggc agtaagttga agatttattc atataggatt tagtagctgc      60
agctttaacc tgtggcttct gtagcttttg taatctggca gtgcgcatct gctatattat     120
ctaaatgttt cctcaaaagg agaaacactc taacaactta tcaccctagt ctgctggcca     180
ccattttccc tcagatgctc acagcttctt ccgtgggatt tgaagatatg acttccatga     240
cacttgatca gtatgtcaat gggtattgaa ccactcttca gctctgatcc cacggttcag     300
ttcctttcag tgtgactatg tgtcttggtg gtgggagatg tgattctttt atctactttc     360
tccatttatc ttactcagag gaactgtgct ctaataggga aatagattga aagcttataa     420
atttccttga gttttaactt ttctcctttg gtctttttttt cttttcaaat gacttgaaga     480
cacattgata agattctatg agaaaatgaa gagttgaaca aattgaatat gtatgagtga     540
atgaatagat taatacataa atgataaatt tattaaataa tttgaacgaa atcaatcgag     600
aggcaccgag aataaatttg tgtcctagaa gtaagaagac ctgagtttga gataactagt     660
agttctatta tactggagaa attacttaat catcactgga cttcattttt ctcatatgga     720
aagtaattca atcacactaa acaatcttta aggtctcctt cacttataaa tgtatgtttt     780
agccatttta ggaggttaaa taatgtcatg tcccatggga cttctgtttg ttgttctatt     840
caagcatgtt agcttgtttc tatcacagga cctgctgcct ttccgcagcc agttctctag     900 attatttttta atcagtcggt gcacacatgg tcaatattta ctcaatagaa ttcaggtttc     960
ccaaattcca tgaggattct tgattaattt tattacttat gccaaaacta ttatcttctt    1020
```

-continued

```
aactattttta ggtccaaaca gttttaactt ttatcctggc atttatatat aaaaaacttt    1080
tgtaagaccg ggtgcagtgg ctcatgcctg taatcccagc actttgggag gccgaggtgg    1140
gtggatcacc aggtcaggag atggagacca tcctggctaa caccatgaaa ccctgtttct    1200
actaaaaata caaaaaatta gccgggcgtg gtggtggacg cctttagtcc cagctattca    1260
ggaggctgag gcaggagaat ggcgtgaacc tgggaggcag agcttgcagt gagcagagat    1320
cacaccactg cactccagcc tggcagcctg gatgacacag cgagactccg tctcaaaaaa    1380
aaaaaaaaaa aaagaaaaa aactgttttta tagtcaaaag aaaaactttc tataaatcaa    1440
ccaatcctgt gaagaaaata tgaaaaatat cctctgtttc caaaaaatt taggctatca    1500
atatatacac ataaagagat aaactctgat aaattggata aataaaattc actataatag    1560
caagttttag agaacaagca cgggagttag tcgacctggg cccttaaaca gatatcctct    1620
ctctcatcct gtgttatttc ctgtgtaatg ttggtatcat tcctgcctga ctctcataga    1680
tttatatgat tcctactctg tccaggtgcc ttattgggtc ttagcggtaa aaagatgaac    1740
aaggctaatg cagcccattg agaagctatc tgtaagtgaa catacatgca aactaatact    1800
tgattcaatg tgagaagcac tgttgctgat cataggtgcc agaagaacag caaagagtta    1860
ttttttcctc caaaattgtg gaaaaatttt tatccccggt gtgatgcaat ataaaataca    1920
cagcaccacc tttgaagtat tcttgccaaa tgaatttaac caaaatctaa tcaagacttc    1980
agagctaaag aaaatctaaa ggtaatccaa tttataggaa atgagggata taaaagaaca    2040
agttaaataa taccacagga aagcattcag acaagtccag aaagtaagat attctaaagg    2100
atgtttagct tgatctcttc aacagtcaat gtcattaaaa actaaaaaag aagcaggact    2160
cttttagatt aaaagagatt aaaaaggcat aacaaacaag tgcactgcat ggtcctcgat    2220
tatgtcttgg cttttacaaa tcatgtgtaa ttataatgaa accatggagg gaacttgaag    2280
atggactggg tattagatga tatggcagaa atatcattaa ttttttagga gtgttaagag    2340
tatcatggtt atgttggata tatcctaatt gtctataata atgatttggt aaaaagtcac    2400
gatgttttat ttcacattaa aatatagcag cagaaaaaat aaatgagcca atacagtaa    2460
aattttcaac aattgatata ataatgtgat atatatatgg atgttcaatt atactattct    2520
tagtaatttt ttatgtctga acattttcat aatacttaaa aataaaagat aaaagataaa    2580
aataaatgag ataatagatt taaaatcact ttgtaaactc taaaaggata gacagataaa    2640
agagataaca aagtgctgga gaaggagga atggtccctt ttcaagcatg tatgccacct    2700
tggaccatgc tgctaagaga aaccattcct gaccaccaca aagaggccac caaatgcctc    2760
taaaatagaa agcaggagca acattaggat tcccagatcc tgatatttt tttttaacac    2820
atcttctcag accaagatga cattgaacaa aattaaagac ctttttgcag ggaaaggtag    2880
gctacagcaa cttgaacttg tctaaggaga gctggaaaac ctgcaagcat tgctatctga    2940
gagtaaccag tgggcccttc cttttctcag gacagtggga tttggcaccc gaagcagaaa    3000
tgctgaagcc atggatgatt gccgttctca ttgtgttgtc cctgacagtg gtggcagtga    3060
ccataggtct cctggttcac ttcctagtat ttggtaggta aaattaaaga tttcactcta    3120
tttgatttta ttttttctgca aagctccatt tacatatatg taaatgtaac ttcatctaaa    3180
aaattgcaca tttaccttca aatttccaca gagtatattt aactgtttca gtcatttcat    3240
caacaaacaa gtactaaatt cttattatat gtgagtactt ttctggatat tcaagataca    3300
gctttaagca aagtagacag atttctaatt tccttagagc tctcaaccca gaattctttt    3360
```

```
gagaatctac acaaaaagat caaaaattgt aattgtctga aacttactag taattataat    3420
aaacaactca tcacttatta tatattaaaa tgaaaagcta tgataaatta gttattaaaa    3480
ttggctcttt tactcatgaa ccatcatttt ctgtccaaca tttctaaggc aaaagaaaaa    3540
cacttgtcta ataaaataag gaatttcaaa atgattgaaa acctatacgt atgacacaat    3600
attatcattt attttagag aaaaaaaatt ttactctttc caaaacaata ttcaggatt    3660
atatttttat caactaatat atttgtaatt acacaaataa tgcacttcaa gattctcttt    3720
ttacattcag tctcttttctg gggagaatgc aagccattta cattttttca caaatctcta    3780
caatgtgact ctcacatgga tgtatgtgat aaaacaaata actcaggctg ctcactttaa    3840
cgctcttatc tgctgtcacc ttcacagagt caatggggga gcaaagactc tacttggagc    3900
cttaaagggc ttaagatcat agtcctaggc cttatatgat aaccccagct gtagtttata    3960
ccattggcaa aagattctca ggtcacttta tttggttgca taaaagtctc tttacaatga    4020
gagtaaggtt tgttaacagt atggattata tgggtaagta atcaggatgt ccaaaaatgt    4080
attacaaggt ccagagattt cccacttaag acatatgcct tcctgatatc cctgtttctt    4140
tccttggttt gtagtctcga aacccactcc ctcttccctg agccaggctt ctcaaggatt    4200
gaggttgttt tgtattttc ccattctcta tctttaactc tgtatctttc ttactccctc    4260
tgggccttac tcctcagatt accaaattcc ttaggagtct caactgcttt cctttcttac    4320
atttcctaat agatttatcc ctgtttcatg ctcgtcttgt cttcaatctc agacagctct    4380
tctctacact ttcttttcag gtttttctta gtgtgcctgg ctctcttgtt aaaaatcaaa    4440
attcacaagg acattcactt atctctactt ccactagagt gtatgatggt acacatttca    4500
actcagcaag gagcaatgta gcaatgaaat gttcaagctc tacagctaga ctggatttaa    4560
aacttggaca ggccacctac tagttacaga acaatttact taatgcctct gtgccttaat    4620
ttccttatct gtaaaatgaa ggtgatacca atcttagaga gctggtgtgg ggattaaatg    4680
ggctaataca taaaaagtgc acaggacagt gcctgccata ttgtagaaac tcaataaatg    4740
gcagctatta taattgatat aaaacattaa ctgttatttt ttaaataaaa ctcaattatg    4800
aagaggctca gggacatatt caagatttat attggcccca ttgtaattga gttctgaaat    4860
ctttgtccaa accatttagt ttcctatttt tcatttccat tgcagaccaa aaaaaggagt    4920
actatcatgg ctcctttaaa attttagatc cacaaatcaa taacaatttc ggacaaagca    4980
acacatatca acttaaggac ttacgagaga cgaccgaaaa tttggtgagt caggtaaact    5040
tcttttatc atagaataat gcaagtggaa gggattttgt ggatcatttc tccatttcta    5100
aaaacatgat tttcagaccg ccaacattag aatcatcttg cagattgcta ggccccatcc    5160
cagacctgct taatcagagt atgatgagat gggtaggtgg ggagaggaga gtaagggaat    5220
ctgcatgtct aacaaatggg tgattctaat aagcctctct ttctaactca gctaccttat    5280
ttaaaggtaa gagaattgag gccaagatat cctagcccgt ttcttcccca attccaccac    5340
gtttcccctg tagaaaagcc taatcatacc aaaactagtt tttataagtc cacacacttg    5400
tttgtaagac cacattttaa gatttgtagt attttcagaa tttacgttca tcttgtaagt    5460
atattgataa agacaaaaaa ccagacttat tttgtagtaa tcaagtcaaa tgctaataat    5520
tttgttaaag ctaaagtgca agactgctcc caaaaagaaa aaaagcacac tcagttgtat    5580
aatcattcca ctcagaatgc ccatgaactc tcactcaaaa actaggttca aattaatttt    5640
tctaacaagg aagcacagaa gcagagactt atttttaaaaa gaaagaaatg acaaatgtat    5700
tggtttgttt taatcaaaga accatttta agacactttc tttcccaaat catctaccat    5760
```

-continued

```
tttttcctgt catcatttgc tctttgtcca tagtatacct aatggcatca tatttacaat      5820
aatattgtag agtttataat ctctattttc agttaacatt aaatcattca caatttctta      5880
attttgtggt ttcatctttc ccaaccaata attaatgtct acagattgat atagattctg      5940
cattctttca catgcagagc atcttataaa agagcatttg caatcagttc ttaagttatg      6000
ctaggatgaa cggggagcct gcaccaatac acccaaatac cttctctact cctccagtcc      6060
taagtgactc cacataacct cctcgatgca aaagagaaa actcttaact tgccttagtt       6120
aaaaagataa acacaccttt gaatgatgga aaatgttaca atttactggg aaattttgaa      6180
atttgtttca tttatatttt atggccaaca ttactgctac tgttgttgtt gtaagttaac      6240
taggcaattc tgtctttact gaagtaaacg acaagaatg caataggtct aaaagaagt        6300 gagagaaatg cagaggtgca tgttgaacag aaactctatt taaaagtgga gttttaagtt     6360
tcacctaagc atgtgttcct tcaaaggcta aggctaagtt aagtaaggac acattatcat     6420
catgggtacc tgcaaggccc ttctctggtt gtcattattt atttatcctc ctttatcacc     6480
atagcataag ccccttaccct ccccccttgc aggaaatcat tctatgtttc atgtggtatt    6540
cttttgtttg tattcattct tacaaaaata tgttttgcta ttttgcgtac acttgctttt    6600
aacttacatt ttgtgttata atcacttttt gtttcatctc tttttactga aactttttta    6660
aaagatatat gttactaaat atacctttag tttattgctg ttagctgcta attcatagtg     6720
tgtatcttcc atatttacct gcctgtcatg ccaagaaatg ccacactaaa cagactccta    6780
cttaccccct tatagaccta tgcaagtact tctggaagca gaattactag gtcattgaat    6840
gtacatatac ttaacttgac caattggtgc aggtttgctc ttcaaaatgg ctgactcagt     6900
gtgcacgccc atctacaatg catgaggatt tctatgtccc cacatctaac caacacttag    6960
tgtcttagta tgtttaggct actacaacaa aaataccat aggctgggta tcttaaacaa      7020
caaacaatta tttctcatag ttctggaggc tgaagattcc aagatgaaga tgatcaaggc    7080
tctagcagat gtctggtgag agcctgcttc ctggttcata gaataccatc ttgctgtgtc    7140
cctcatggca gaagccataa gagaactttc ttttgtaagg acactaatga ctttcatgag    7200
aactccaccc tcatgaccta actatcctcc aaaggcccca tctcctctat catcggtttg    7260
ggagttaagg tctcaaaata taaatttcag gggaacacaa acattcagtc cacagcactt    7320
ggtattattt ggctttctaa atttgccacc ctaatatgta taaagtagta ttttatttgt     7380
gatttaattt gcatgtttct aattactaat gagtttgtgc attgttacgt ataattatta   7440
acttttggta ctttcatttc tataaattgc ctgtacatat tatttgccta ttttttctgtt  7500 aaacttgctt tttcacctta tttgtattgc tttgcagaag ttctttacat tttctggata    7560
ttgatagtgt gttggttgtg gacactgcgc ttatccattc tgtcttctac taatatggac    7620
cgtgttgttc tttatgaaac cgaaatctgt aactgaagta atcatttttt cactgttttg    7680
ccttatgatt gtattttgaa gcttttcttt aagaagtcct tcttcccttc taagacataa    7740
aaatatttta ctatgttact tattaacctt atagttttat cttttacatt aggtctccaa    7800
tacatgtgga atccaccttt ggatgtgtta ggtagattca gttttttaat tcatatagtg    7860
agccagtttt tgaatataac tagttaaaat atcttggctt ttcctaatat atggtattat    7920
tattgagttc attgcatgca tttcttggca cctgggtctt gcagaaaagg aaacatgaat    7980
ctgtctcctc aaattgcttc caatctttt ggaaagatgt gagtaacaca catggaattg      8040
aatatcatga catgatataa ttaagggcta aattacatgt tgaggacagt aagtacagaa    8100
```

-continued

```
aaacttcaaa accaaacaag ggttcccatg gtcagaaaag ctttatatt attttaccttt    8160
tgtttaaatg agacaggtgt ttttctcctc ccatcccgca ccaggttagc tttagaagaa    8220
ttacaggaag agtttatgcc tcatcctgag ccacacctgt ttgttgttgc taaatcccaa    8280
tgaatacaac cagattcttc tctctgtcct atatgggtgc taattagaca accaaggaag    8340
aacaggttgc acgtcctgtt cttcctcaca ttgggctttta ctgatttgaa tgcaaattga    8400
gatgcaaaag taaaaatgag ttcatattta gatattgcta taatccgccc ctgttccctg    8460
agatagtgga gcagacatat ctcatctctc atatcattct tcagagaagg gtccattaat    8520
cagacattac tgatgtctga ttactgccgg ctggccatcc tgcaggtgga gaagcatggc    8580
atccagcaga aactgacagc atgcactttg agggagggaa ggataagcca ggaatttatg    8640
ctgaataagc tgcctaagta tacatgttca ataagttcta ggggaagtca caaatactta    8700
tgaaaggaga aacataacta tgtgcaattg agctttatgt ctcttcatgt gttgcatgtt    8760
caaaaaatgg tggcattagc atgatccaag ggtggagttt tcagccattt gatgttcaaa    8820
ggtgaagcag aggacacaaa acccttacta tgcatcctct gtgagtcagc caaaaccagt    8880
ctggactgct agctagatta acaaagaaaa aagagaaag aagatacaaa taagcacgat     8940
cagaaatgat agaggtaaca ttacaaccaa tcccacagaa atacaaaaga tcgtctgaga    9000
ctcttatgaa cacttctatg tagataaact agaaaatcta gaggaaatgg gtaaattcct    9060
ggaaaaacac aatcttccaa gattgaatca gaaagaaatt gaaaccctga acagaccaat    9120
attgagttca tacttaaatc agtaatttaa aaaacttacc agccaaaagg aaaaaaaaag    9180
gcccaaacta gatggattca cagccaaatt ctaccagacg tacaagaaat agctaggacc    9240
aattctagtg aaactattcc aaagaattga gaagagactt cttcttaaat cattctatga    9300
agtcagcatt accctaacgc caaaacctca caaagacaga atgaaaaaag aaaattacag    9360
gccaatatcc ctgatgaaca tagatataaa atcctcaac caaataccag caaaccaaat    9420
ccagcagcac atcaaaaagt taattttcca aaatcaagta ggctttattt ctgtgatgca    9480
agactggttc aacatatgta aatcaataaa tgcgatttac cacataaacc gaattaaaaa    9540
caaaaatcat acaattagcc aggcatggtg gctcacactt gtaatcccag cactttggga    9600
gaccatggtg ggcaaattac ctgaggtcag aagttcgaga ccaacctggc caacatggtg    9660
aaaccccatc tgtattaaaa atacgaaaat tagccgggca tggtggcagg tgcctgtaat    9720
cccagctact cggagggctg aggcaggaga atcacttgaa cccaggaggc agaggttgca    9780
gtgagccgag atcgtgccat tgcactccag cctgggtgac agagcaaaaa tccatctcaa    9840
aaaaattaaa aatttaagaa aattaaaatc atacaatcat ctcaatatat gtagaaaaag    9900
cttttgataa aattaaacat cccttcataa taaaaacact tagactaggc atcgaagaaa    9960
catacttcaa aataataaga gccatctgtg acaaacccac agccatcatc acactgaatg   10020
ggcaaaagct ggaggcacta tccttaagaa cagggaaaaa gacaagaatg ttcactctca   10080
ctactcctat tcaacatagt actagaagtt ctagaaagag caatcgagca ggagaaagaa   10140
ggaaaatgca tccaaatacg aaaagaggaa gtcaaattat ctctctttac tgacaatatg   10200
attatatgcc tagaaaaccc taaagacttt acaaaaagtt tccaaaactg ataaacaact   10260
tcagtaaagt ttcaggatac aaaatcaatg tacaaaattc agtagcattt ctaaacaata   10320
atgtccaagc tgagaaccaa atcaagaaca caatcccatt ttcaatagcg acacacacac   10380
acaaatgaaa tacctaggaa tacatctaac caaggaggta aaagatctct ataaggaaa    10440
taaaaaaaca ctattgaaag aaatcggaga tgacacaaat gaatgcaaaa acattccatg   10500
```

```
ctcatggatt ggaagaatca atattgttaa aatgtcccta ctgcccagag caatctacag    10560
attcaatgct attcctatca aactaccaac ataattttcc acacaaagtt agaaaaagct    10620
tttgtaaatt tcatatggta caaaaaaaaa agccccaat agccaaagga ctcctaataa     10680 aaagaacag agccagaggc ctcacattat ctgacttcaa actatacttt aaggctacag     10740
taatcaaaac agaatggcat tggtcaaaaa cagacatata aaccaataga acagaataga    10800
gaacccagaa ataaagccac acatctacag ccatcagata ttcaataaaa ttaacaaaaa    10860
taagcaatgg ggagagaact ttctattcaa taaatggtgc tggaatagct agctagtcag    10920
aagcagaaaa atgaaattgg actcctatca ctaaatacaa aaactaactc aagatgcagt    10980
aaagaattaa atgtaagacc acaaacaatt aatacaagaa ccctagaaga aaacctagga    11040
aatactgttg tagacatcag tcttggcaca gaatttagga ctaagtcctc aaaagcaact    11100
gcaacaaaaa caaaaattga taagttggac ctaattaaac taaagaactt ctgcacaata    11160
aaagaaacta tcaacagagt aaacaaacaa cctacagact gggagaaaat atttgcaaac    11220
tatgcatctg aaaggtcta atgtccagaa tctgtaaaga acttaaacaa ctcaacaagc     11280
aaaagaaacc aagtaacgcc attaaaaagt aggcaaagaa catgaacaga tgcttcacaa    11340
aagaagacat acaacgcagt caagaaacat atgaacaaat gctccacatc actaattatc    11400
caagtaatgc aaatcaaaac tacagtgaga taatatctca taccagttac aatggctatt    11460
attaaagatt aaaaaaataa catgctgatg agactgcgga ggaaagagaa tgcttaaata    11520
ctgttggaaa cgtaaatggg ttcagccact gtggaaagca gtttggagac ttctcaaagt    11580
acttaaaatg gaactactat tcaacctagc aatcctactt actgggtgta tacccaaagg    11640
agtataaact ttttttcccag aaagacagct gcactctcac attaattacc acagtattca    11700
caatagcaaa gatgtggaat caacctagat atccatcaat ggtggattgg acaaagaaac    11760
tgtgagatat atatgtatat atctctat ataccatgga atactatgta gccataaaaa      11820
aggatgaaat catgtccttt gcagcaacat ggatgtaaca ccacaaggaa ggcacttta    11880 tctcctcttt acaggtaaga gaaccaagct tctgaaatta aggtccatag ctggaaaatg    11940
atggagggga gatttgaagt catctaggca actccacaca tgtgctcttt ccactaaatt    12000
gttctactgt caggaaggga ctcagctaag acagaagata aaattattaa aatctaaatc    12060
aattcttctc tcatttcatt ttttaaatcc atgaagatta taaatcctct atgctgtgct    12120
agctaacttt tcttgacag atacattagg tatacttatt agagaaaaat attctctttc    12180
tcatttccct gtatcagttt ttggtgagga aggcaaaggt aggaggaact gtaatagaga    12240
aagatgaagg aagctgatgg atatattgac atgtgtatgt acatctagtg tgaacaatct    12300
atagttggaa gaaaggtgtg gatgggtatg cttttgagg gaagttttg agaaaagaag     12360 taatatgaac tatttctaaa tttcctgata aagttgtaaa tacagcatag tcttcacagg    12420
agaatctatt tagtttatca tcatcattca gcaaatacag catgatgtta ggcactataa    12480
aaggctaaga aaaatgattc tctctctctc ataaactaat ccaatttaga gatttagaag    12540
acaacaaatc tggagaggac atgaaccttc taaataatga ccttcccttg ctttgggtat    12600
cctggtttta aatattttta gtacagcttt aaatagatcc aaatgagata ttttcctctt    12660
ttacaaaagc aattcaaaga tctaggtttt tgttgtacac tgagaattaa tacttttttc    12720
tttaaaatcc ttaattgcaa atctttaaat tctataaata ttttgccttg tgatctcaga    12780
aatataagcc aatttgggat atggatatct aatatattgc tacttgttac acgtgagtag    12840
```

```
tgacagatgt ctgtccattt ctttctgaca ttccacaaag aaacactgaa gaaggaccag    12900
tgcaatcaaa gaaatgactg atggcatcac aaaatatcac atcccatttg atgatctgat    12960 taccttttg tttagggtga tcagaaagtc acagtttcat ggcaccctcc acacccacac     13020
accttgtatg acactggatc caactgcttt ctccaataga cacagcactt aaagatgtgg    13080
cagttaggct tgaccccaag aaggccaaaa agccttctgt gagcatcact cagtgctcag    13140
gttgactaag ctctatccag gcttgagaga atggttcata gctgacttct tggatccaaa    13200
aaaaaaaaaa aaacacctag agttttatac agatatgata cgaacttaaa aggactgcac    13260
taaaaactac caagattatg attcttattt ttggagagta aagaaaatag gctgcctttg    13320
gagaggggtg caacagtttc tgatcctctt acaaactgct tgctgcccat cagtgggtag    13380
gaggtcttag tgagaaccta cctgcatgct catcctgagg taggcactgt gaaggcgtta    13440
acaggctctg aagctacatg gccctggttt cagtgaactc tgtggtgtca acttgggcaa    13500
gtcacttcct cttctatgaa acgtgaataa tcatagtact caccttagag ggctgatttg    13560
aaagcaaatg agctcaaaca caatgacatc tgtgcttggt gcatatatgg cagacaacag    13620
tgattcccac tattataatt attacagtct taccaaggag gagctttcca caataatca     13680 attacctaaa atgtccaaaa acaggaaaaa aaatctctt ccgataattc atgtgtaatt      13740
ttcttttttc tctaggagca ttgatctcaa cctgatgtaa agcaagcact ttaaaaagtc    13800
ttataaaatt ttcctggtaa atgcaaaact ttctgataaa taaattctca cctttttatc    13860
aatttgttaa ttcaacaaaa atatactaca taccaacagc atgcaaagca ctatgctaga    13920
ttttatagac tatgaaaaga taaattgcca tctctatgca taaagggttt gccatttaat    13980
aaaagagact atatatttgc ataaatatat agtgaatata ttgcataaat atataatata    14040
tgtttacatt aaagaataaa aggtataaga gggataagaa aaattgagac agagggaaga    14100
caggtcagtt tgagattaac gaatatcccc aaagaaggta ttatctgaga ttggccttga    14160
aggatagttg tgattcagga acacagaact tgcagaatga gaaggttgtt acagaccaaa    14220
ggaacagcct gagaggcgtg agtatgcagg aaaatgaggg ccatgcctga agtactggt     14280 ggtgttgaag atggagccag gcaagttggt cacagaggga gaggaccttg aatgtctaac    14340
attgtggaca gaggctcaaa ggctcaaatt ccctattttt accttgagtt caatccttgt    14400
ggcaatgaaa cctcagtgaa gctttattta aggctaaaag tgtcttttaa aaatccctct    14460
tatataatat cctttgcatg ttactcttgt tgtaattagg agaaagcaat aggatctaaa    14520
gttttttttc acagcatggt tttggtttct ttaattctaa ggagctcacc tggtgttacg    14580
ttggaaaaaa cagcttttat atctcattta tattccatat gccagtctgc agtgacatat    14640
ctatctgagg tttacagtgt tagccacaaa acactcccta agtgaataca ttgactgctg    14700
taaggggagc cagtcaggaa gcacctgcag agaaaagcag gcaacatgta taaacagagt    14760
taattcagga atgaaagctg aatggctggg cgagtctgtt tgtttgagtt gacagcctct    14820
ccctcactct ttcattaaat atccaactaa ccttcaattg ccctcttgga acttaatctc    14880
agtgtaattt ccagcatgtc aaaattatca agcagaaaga gatactaccc tgaaagaggg    14940
tcttttgttc aatgctagga gacaaactcc aactacaaaa ttctagaaat gccctaaaga    15000
gagagatagg atagatttac aaattgctaa tgctattagg ttgtatagat aacaatagat    15060
ttataacaac ctggcacaca gctttaaata tataagttc tctgaaactt ctgggaactt      15120
ggaatgccag aacgttggca aaaagaatgc ttctaataat gaaagccatc atctgccatg    15180
gaaacaattt cagggtcttt agaaagctag tttatacata agctccattc tacaataaaa    15240
```

```
cttatgttca tgtttttttct gattttcctc ctgctgtaaa ttcattttat cagaattctt    15300
tttaccagtc cctctgcccc atttctcaaa gcgttgtcct cagactacct gtatcaccta    15360
aagattctaa ggcctcctcc gatgtagtaa atgagacttt tctagagaga gagtcctaga    15420
attttataaa gaaggatcct ttttattatt gtgatcacca aagttacttc tgcctagatt    15480
cttctcatgt tatttttaca gctcctatct tcccagacaa cctaacaatt caaagataaa    15540
attggtgctt ggtttagaca ttcatagcag gcacggtgcc agattgatga tgtcatccag    15600
agtcaaaaac ttcatccaat gccttcacca aaaagttaca aatggccagg aatcaaatgt    15660
ggttgaactt attcagaggg taattacaaa acaaacttct ttaaatacccc aactgctatt    15720 tgcttttttc cttctaaatt gtatcacttc tctccctgtt ccattttgtt tgccttttta    15780
ttttttggaa tccctcacct ccatactgag tagtagagct ggctgtgggt gatgagagag    15840
aaattgttat aacaaagtca cccttcaaa acatgtctt ccaaaagaat tttgtttcta    15900
gcagataaac cccacaccac ctcagctaaa tggggctttc tttatttaag taccaataaa    15960
gacatatttt ggatactagc aatttatttt ccaaatgcta tctttgatct taagtttaag    16020
gctattacca aatctatatc tctacaagtt ttatacttta ggtcaataaa ttacttgata    16080
acttattact atgtgttcta caaaagaaac cgaagtaaaa tttacatcac atttaacagg    16140
gtggttgtgt gattgagtgg gaagaggcgg accctacaga tagaagactt gggtttcagt    16200
cccagcttac tagtatctgc gtgatgccag ggaaattcac ataatgcctc tgagtcacag    16260
atttctaaca ggaatgaaga tacttcttcg cagaattgtc attagagtta aagaagataa    16320
caaataatgt ggttcctgat gaggtattta tgaattcctg agcatgctaa ggaagttata    16380 acttgttttct tgatccctga aacagctttc cctatatttg tgtgtgtgtg tgtgtgtgtg    16440
tttcagtcat gcaagttggt ttttcttctc attccttgag aatttaggat attttgtgcg    16500
cacatttggt tcttctgtcc aacatgaact gtagtacctt acccacattg agatgacact    16560
atttctacca agtgagtgct aggggatact gcaagccgaa tgccaggtgt gagagaccac    16620
agcatcacaa taccgtggca gtagattaaa gctgtgcata tggactaaaa gcagtggctt    16680
tgcttctcct accttggtga cataaactga gtaacaaatt tgacctaata ctggaatacc    16740
acctaattct ttttttcctcc ctgatttacc ctagagtcca caattgacaa taatttaaaa    16800
attttggctc tctcttaaat ccctaatgcc tcctccttac accttacaag caaagacctg    16860
cagagctaag acctgtaatg ccaggatgga ggctagagga ccatcagcaa ttaactacca    16920
aaacttaccc aacattttat atctgtttaa ccttcatagc cttatgagta gcagatcaat    16980
atctttgttt tacaggttag aaaactgagg ctcaaattga ttcagtaact ttgccaagat    17040
tgcccagttt gggaaaagta gtatacgctc aaatccagga ctgaggcagg gttttctttg    17100
tcaccactca aagcctctct gaatatccta tctctgctct gtatctctct gctactcctt    17160
ctatggtgtt ttagcaagat atcttctact ccagaaacct actctagcac agtagaatta    17220
cttgggtagg ttttttaaaa atatgagtgc ctaggtcccc tctagaccaa tcgaaaccaa    17280
aattcttgga gaggatccct ggcatccata aatttttttta attcatcaaa tgattctgtt    17340
gcactgtgaa agctgagatc caccaattta aataatgatg ttagttctgt gaaaaaattt    17400
ttgattgctt taacatttaa tcaaggatat attcctatta taaatatat tattaacaca    17460 tagtttctct cttgttgtgt aacaggtgga tgagatattt atagattcag cctggaagaa    17520
aaattatatc aagaaccaag tagtcagact gacgtatgta tgtttgggca aggtggaat    17580
```

```
cacaagactg agggaaaag gaacaaagga gacagggact ctcatgtatt gtatgtctcc    17640
atggactagg cttttggcta gaattttca taaacattac ctttaaagca gtcttgaagt    17700 ataggctga ccaccgtttt gtcaacaaaa agactaagat tcaggaaggg taagaaatat     17760
gttcaaagtt caccaactga cagtttccca aagtgacaga accaggaatc aaaccccatt    17820
aacttattgt gaggcctgga acctaccaga acccatgacg tggggaaaac ccagcagctt    17880
gtcgttgcat gcaccaagtt atattatgtt gacaattata ttatttcaac cacgttaagc    17940
aggcaaactt ggctataaaa tgggttcaca aatttaccct gtaatgtaac cgaatgacat    18000
aaggcatgcc taaacaaaaa gatattcctg ttgtaataaa ttttctttct gtcatggtgg    18060 aggggaaga ctcatatcag ttgcagatat tgctcagaag tttcaattgt gttattttga     18120
aaaactacat agcagaacac gcatgtcata tacacaaatc catgagcctg tatgactcat    18180
atttcttaaa gataaagaaa ataatatat tcagattttg atttatttga agaaataat      18240 tatcccttc tcaccaatag actaataatg ctttgttggc aggtgtactc aaagttctct     18300
atgtcttgac tgagtaacta gtgacttccg taaggatttt ataacataaa ttgggtaatt    18360
cctacaatac ttaggaggga aaagcatat aaatgctaga actttctaga tttcatgttt      18420
tctgttttca aattctcctt taccatatta ttgtagcaac attattatac tcctgtgaac    18480
tcctttggat ggtagccatc actatataat acctggtaaa aatgttaatt cctcagattt    18540
aagaagtaaa attagtcatc tgtttgccaa tttgacataa aattctagtt atttagatct    18600
ttatattcca gagcctaaat gaacaaaaat acataaattg tctcagaatt tccttttagc    18660
caaaagattc agggagatgg gcctctagag ttttcacag tttttttttt ttttgtaaaa      18720 aaaaaaaaa aaaaaaaaag gagagataac agatcaatat atattagttt caaggttttt    18780 tgttttttt tttaaacaaa aacctgtaat tgcttttcct attttaacag tatttaaaag      18840
tttagttcct caggtaacag aacttgaacc tgtttatatg atcaaagttc aagaaattgg    18900
gcatgtttaa tttggagaag actcggggac cacaatattg ttgtcttcaa atatttgggc    18960
tagaggagga aattatttta tgtatgttcc aactggtaga cctaagcctt atggaatggg    19020
agatataggg agacatattt caactcaaaa tgatgaactc ttaaaagcag agctgaccaa    19080
agagaaacaa gcctctttag aaaattaaac ttactatctt tttaattact gcactgtcat    19140
tagagggcca attgtcatgg accctgtaga agtgattcag gtatcaaata tacaattgat    19200
tagcctaaga aaacatgaag gcttcttcta actctcagag cttgtaattt tgatgatgat    19260
tttttatatc tgtcattcct agctgctgta acaatccttc aaattaatgg gggaaatgca    19320
ctgaaaacat aatgaaagct agaagaggga acatatgaaa tgaccttggg tcagaatgac    19380
atgagaggat cagcacttga cactctcagc aactgaggga tcattcaggg gaggaagata    19440
caggtaagac tgaaggacaa ttccaggtgt attctttgaa aatgtaccTt tctttTgtgt    19500
gtcacagtcc agaggaagat ggtgtgaaag tagatgtcat tatggtgttc cagttcccct    19560
ctactgaaca aagggcagta agagagaaga aaatccaaag catcttaaat cagaagataa    19620
ggaatttaag agccttgcca ataaatgcct catcagttca agttaatggt aaggaggtcc    19680
ccttctatgt gatatgaagt tgtctattag gtccatgttt tgacgaatct caaatttatt    19740
tgtcattatt tccatttcaa ataatagcta gaattcagat gaaaaaattc aagttaaaga    19800
tgtgacattt caaggtgtat tagtctctaa cgtaagcatg tctgaagtta gtcatccagt    19860
ggtttttccg acagtaattg attggcactc atcccaaaat ataggcaagc atttacaact    19920
aacagagagt taatcccacc caggcactgc ctccatgact aagcaagtga aaatactagg    19980
```

```
ggtttagcaa taattgtttt tctgggtggg accttcctaa acacaaatt catgtgttgc    20040 catacttta ttgatagttt ctatatatgg tgatatacaa ttttgttag ctttttttcc    20100 tatgggcatt tgggaaaatg gcaagccaac tttgaagttg ttagagtcat tttaccatta    20160
atgctttaaa aatcacagtc taggaaaaca tcactgaaac tatgtgtaca ttgttccact    20220
tttctctttt tttttgttca cccttagccc attataccat tatcacttcc ctcaattaag    20280
gagaacaaac ctttatcaag gtctatctct atggccttta ccttaagtaa ctaatttctt    20340
tttatattcc agtgacgtac gcaaattcac ctttatagaa gtgaaattca cacaaaaaga    20400
gttgaggaat tcagtaatta aaaggagcta agaatcaaat ttaaatctct aatttcttaa    20460
aaggctccaa ttaaaaaagg tttctatagt caaacacatc ttaaaaattc tggctttgat    20520 actcgttct tggaaattct tccttatagt gtcatattaa aaattctaag gcagccagct    20580
agagagaaac ttgtttaccc tcgtccgcta agctgtttgc acagcatctt cttccaacag    20640
acaagtatag atttctccta caaatttcaa tggataccag acctaagtgt tacagaagag    20700
attcagggca agcgattttt atcagacatg aaacaggaca ctctgccctt gtaaggtctc    20760
agctgacact tcaagaggaa accagataag gaagtaaaaa atgtgaggta atggaatggg    20820
cagatgtttg ctgatgtgag aacgagtcag ctacttaggg aataaagctg aggacctctc    20880
ccagccagaa gggaggaacc tgacaagtgc ttaatccatc ttctttgtta gatggggaag    20940
caaatgaata gaagttgtga acaatgggc attctgataa tttacatgat gctttctgtg    21000
taatttccaa taaatagtta atttgtcagg aatgtaaaag cctgaactat ctgaaaccag    21060
agtaaagcat aaaattgttca ttggctgcct ggtctttttg tttttgtag gctcagcttc    21120 taaacttcag cttattttaa taattgtact aaattaaatg gtaggatatg ctaatggaga    21180
acctgatttg agagtcacct gaggctgggc atggtggctc aagcctataa ttccagcact    21240
ttgggaggcc gaggcgggtg gatcacctga ggtcaggagt tcaagaccag cctggccaat    21300
atggtgaaac cccgtctctt ctaaaaatac aaaatattag tcaggcctgg tgacgggcac    21360
ctgtaatccc agctacttgg gagactgagg ggaagaatc acttgaaccc gggaggcgga    21420
ggttgcagtg agccaagatc gcgccactgc actcaagcct gggcttgaca gagcaagact    21480
ccatctccaa aaaataaaa aataaaagag ttacctgacc aattctaact ccactaagtc    21540
accacaggac cacccaaata attggctcat gcctttgtct tcatttctc atctgtaaaa    21600 ttccaatggt aatgtttgtt cttcctgaaa tcacagagag attataacga tatacaagga    21660
aatagaaaac acaatgtgaa ataaagaggc tgttactaat gagaaaacta ttatgttgtg    21720
catatgcttt ggaaacctga aatcattaat ttgagtgatt gactagtagc agaaagatag    21780
atccttgaaa gtttcagaat gttcaatgta gaaagaacag tgtttgttag tgatatggga    21840
gcctaggggg tgttgctttt ctggccagaa acctctgtgg ccagtggttg gtgcctttgc    21900
ccaagttttg ctctggccca ctgggcttgt tctgcccact tgacctggca gactgtgccc    21960
accttccgct accagcctgg atcccatgcc caccaaggcc aacccaggca tggagctgtg    22020
agggttgtct gagcgagcac agggtctggc cactgcccac agccaggcac actggctgca    22080
gcatgacggg cagctccagg cactggcaca ggtgtgctgt ctctctgtga ggctgtggct    22140
ggacaaagct cactgcaagc agcttccctg gcaggcacct gggaatgtgg tggcacccag    22200
gaagcttgga gatgccagga actgcagggt cccaaagagg gagtcacaac cctggcttgg    22260
ggagctccca ggtctgggat ccctaaaggg ctgcagcttt tctctctttt tacccacaat    22320
```

```
gtggccagca agggqtatgt ttcattcctg tttgtgttac agctcttttta gtcttgctat    22380
ttggcaggtc ctgagttctt gtcctgagac caagaagaat gaggtatgca gacaagtgga    22440
gggtgagcaa gacgaagaaa ggtttactga gcaagagaac agctcacagg agacccacag    22500
tgggcagctc ctcttcatag ccagggtgtc ccaacaagtg tccagctcct agcaaagagg    22560
aggccctgga ggtagaagct cctctctgca ggcaggttgt cctgttgagt gttcagcttt    22620
cagcacacag taggcagtag gccctagagt ggtctatctc ctctctgcag gcaggtagtc    22680
ccatggtctc ccagtcacct ctccatctgc aagggtccaa tgctgcctcc agcacctctc    22740
tgcccacccc tccgtgcctg accaagctgc tcccccacca gtgggcaact cagcccagcc    22800
ccattgtggt agctcccagg gtggcaggct ctgggggget cccagggatg ggctccaagg    22860
actgtccacc ttctccccac gccctccctg cagtggccat ggtcaagaat ggcaatgtgg    22920
ggccaggttc cggagcagga gaggctccag gcctgggagc aggtcctgcc tggtcacgtg    22980
aggttggggg tggcacagtc ggctgcctca gggatgtggg acacagggga cccaccacca    23040
tcactgctac tcccgcatcc gctcctgcta ccactgctcc agacagcctg tagctgccat    23100
cactagcact aagaaaggc acattcagtg gacagctcag gaaaatcttt acgtcaattt    23160
tttataggca aaaacattgt ttcctgggca aacaaaattt atggactacc aataaataga    23220
aaactgtaga gattctagat taagtctaga aataatcctg tagcccaaga tttatttata    23280
atttgtcaag aatctgtatt ttgttttgac aaaaaaaaa ctgtgtggtg tgggtccttc    23340
aggagacaca gtgtgacaaa gcaaagctaa atcaacttc tttgcattgc aaacaccaag    23400
gctgtagtca agcagctcac tgcctatgtg tcagatgact ttgcttcatt tttcatcatg    23460
atacttgtag tctatagagc cctgaatatt aactagcttt ctcccaactc agaaccgtgt    23520
taggaggtgg ttgctttcaa aactaaagtg ttaatgttta tttccatttc tataccagga    23580
aagtaaaaat ctttggtcaa aattagaaat ctttaacaac tagttacttg tgtattgaca    23640
gtttgtttcc aggtgtaatc attctccctt aaaatccggt tatattcacg accattatac    23700
ttatcctggt atcattcctg gaaatggcta acttgcatcc tgctcagact aagttgacaa    23760
agtttcaatt gaagaattct aactttatgc tattttccac tttattgcat tacaaaggac    23820
aaaatatata gttttcttaa aaatgaaata aatttactgc cttaaactac atttgacggt    23880
aaactgagtt ccttccatag aataaccact aacagcaatc gatggtcctg agcaattgac    23940
tcttcaccat acaatgattt gggatgcctt taagggtata tttgaattga atattttcaa    24000
aagctcccac tttgtagagt ttatcatcac tagtttcccc agtggaattt gtagaaagtt    24060
agtagaatga aacaatctta ttttgtataa tgaggaatag aatactgaga atgtgtctga    24120
gaaacatggc actggtagga aaaagtaaac agtttattct catctgctca ataagctaag    24180
tcattttaac ttgaaaatca tcaaaatttt catgaaacct tccaccaact ttatttttcc    24240
ccagctttag taagatataa ttgacaaata aaaattgtat actgtataca acatgatgct    24300
ttgatacatg tatacaagtt taaatatttg tgtttcctta gtcaaactcc tcactttttt    24360
ggaagttgac agaatttaat cttggattgt gtccaataac tagcttttac cactattcag    24420
tatattttgg ataagaaaca cataacagtt tattctttaa aaaagcaatt ttactattta    24480
ggaactgtgt ttaaaaagca ttttaaatat catttatgca agagttttca aggttttttc    24540
attctaaacc ctttaaccaa aaaaaaaaaa aaaagatttt atgtgaaatt cgaagtaaat    24600
agaagagatc aaagcagatc tgttctggct gaggctgagt ttgagacctg taagacagtc    24660
tacttgccat atggcttggc tgtgtcccca cccaaatctc atctcgaatt gtagcccca    24720
```

```
taattcccac atgttgtgag agggacctgg tgggagataa attaaatcat gggtgcagtt   24780
tcccccatac tgttctatgg tagtgaatga gatctgatgg ttttataaga ggcttcccct   24840
ttcacttggc tcacattctc tgacttgctt gccaccatgt aagacatgcc ttttgccttc   24900
ctccatgatt gtgaggcctc cccagccaca tggaactctg agtccattaa acctcttttt   24960
ctttataaat tacccagtct cagatatgtc tttatcagca gtgtgaaaac aaactaatat   25020
aacctgtttc ctctgtccca tttatccatc ttctgaagtg gaatgcaaag aagctttacc   25080
ccgaactgct ggaaaaccat agttctctat taatacaaac tatttgtggg ctttagtcat   25140
ccactatttg tgccttactc acccattgct tgtgatagta tccacctaat tagaggctgc   25200
ctataagtct ctacaaaaac tgtacacaga tgttgttata tcagatagcc attctcctaa   25260
ttaatctata tgttcaactg tctagaatcc atatatggtc agtatcctct gattattcct   25320
ggtcattgag accaaccagg aaaatatcaa attatcacta tttgttttat cttctttttc   25380
agcaatgagc tcatcaacag gggagttaac tgtccaagca agtaagtcaa gttagcttat   25440
ataaacaagt tcaattttca catcagaaag gacatttttca aatatttgct catacttgcc   25500
catctgtcct ccagattttc tttgagagat aataactatt tgtacgatag atttaaatac   25560
attttttttc taactcatgg actgatcttt tagtcatgtt caagaaaaaa attgccatgg   25620
taaccttctg gggcaatttg aagaaagcat ttatttttga ttgggaatat tggacttgtt   25680
tttctaattt ttaaaaatgc cataaaatgt actttctgct acaaaataaa ataataagaa   25740
agtaatcaat aggaaggaca taaaacccat tgtctgtgac tgacaatttg tctgtgaaat   25800
atgctaaggt caggagttcg agaccagcct gaccaacatg gagaagaaaa cccatctcta   25860
ttaaaaatac aaaaattagc caggtgcggt ggcaggtgcc tgtagtccca gctacttggg   25920
aggctgaggc aggagaatca cttgaacctg ggaggcagag gttgcagtga gccaagattg   25980
caccactgca ctccagcctc agcgacagag tgagactcca tctcaaaaaa gaagaaaaaa   26040
atatgcttaa tagattcatc ttaatcgcta acagtggctt cattaaatca cttcaaatca   26100
ctgtggccta aattttgaaa gattttacaa aaaacagtga tgaatttgag caatgatgtt   26160
catgcatttg cctctgtgac ttgcaaacac cctaagtatt tttatccatg tgtttattca   26220
ttcaacaata tcttttaaca tctaccaagt gccagaaatt agaccaggag ttggtggtac   26280
cattgtgaat aaaacatgat ccctgctcta aaattagaat tccaaagtag agaaagatat   26340
aaataaatca ggaagtatga aaataatgtg attaatgcta tgacagagga agtgcatagt   26400
gctatgagag ttgatcagag agtcagctaa cctgttctca cacagtaaga aagtgaaccc   26460
tgaaatgtga gagagaagag gccatgaatc cagtgacagg tggggtaagt gtcctgggca   26520
ggaggagtag tatacgaaaa tgtcttcagg caagtaagaa tggggtcatt tcctgtaatt   26580
acaagatgtt tcttataact taatgatctc atctttttc aggttgtggt aaacgagttg    26640
ttccattaaa cgtcaacaga atagcatctg gagtcattgc acccaaggcg gcctggcctt   26700
ggcaagcttc ccttcagtat gataacatcc atcagtgtgg ggccaccttg attagtaaca   26760
catggcttgt cactgcagca cactgcttcc agaagtaagt tattgacctt aagttagaac   26820
ccacttctgc taaaaagccc tgagttttgt catattcttg gtaacaatta atgtctcaaa   26880
tattactgaa gtaaaataag aaaaagttat ttcaggttct tttctaaaat aatgttacac   26940
ttgcatactt aatcgaaat ttgatgggaa taagtaacag tcattatcct agtatccatc    27000
aatcatttcc tcaaagtttt taataaggaa actgtgtaaa gaaatcagaa ctattttgtg   27060
```

```
acatcctaac acaaaatatt cactaataac atgtaccatt aatcttttgt caaacaatgc   27120
tctccactta aaactagtgt ctgtttctgc caaacacttg ggccagtctc atactgatct   27180
taaataatca aactaattcc aaagtaaaat ggaaattttc aataaatgcc ggaagttggt   27240
aaccgtgatg atggagaact gcagatcaaa tttagagcat tgacatatga agatctgtgg   27300
aatcagaaca gtttacaacc aaaatgagag attgctagca tgataaagac aggcacttca   27360
aaagagattc ctcggagtat caaaggattc atagaggccc ttgggccact caatgtgacc   27420
ttcccataat agagcatctc ttcacaatag tgacacaaaa gacaaagctg aagtgaagaa   27480
tagcaaattg tgctatccta taattgtttc tgaatgcata cattttatta aatatatgat   27540
taaatgactt tttataactt ttaatcttac ttttcaagat aataaccagt catttttatc   27600
actattacat ttagaatttt agatttgttt ctaagtagat taactgtatc gcctttcttc   27660
ttcattgcca attattacag taataacaaa gacttcttga gtatctctat ataataggtg   27720
gcagcaggat ttagtgggaa aaatatgtcc caggcagttg gagagctggg caaattattg   27780
aaccttagtg tattaggtaa tagataggct agatcttttc acattctttt tgacctataa   27840
aattctaact tttgttacta taataaattt catttgccta ggagcataaa tctttataga   27900
gactcttaat attccaaaga atatacatat taagaatcta ggcttggcat ggtggctcat   27960
gcctgtaatc ccagcatttt gggaggccga ggcaagagga ccacttgagc tcaggagttc   28020
aagaccagct tgggcaagat agtgaaaccc cattgggcat ggtggtgcat acctatcatc   28080
ccagctactt gggaggctaa cgcaggagga tcccttaagc ccaggagttt gaggctcctg   28140
caagctatga ttgcaccact gcactccagc ctgagtgaca atgcaagacc ccatcttaaa   28200
aaaatagtaa tatatttta aaaataatct acataaattc ttaatgtttg aaagatgtga   28260
gagctcagta agctgatata ttagaaagcc agaaatccct tatgctggtg tctggttttt   28320
caaagtaatg ggaaacttac tttgccaaag ttagccattt ttgtggtaga tagttctatt   28380
tttgcaaata tctttatagc attgaacacc aaatctatac tctattaact tctaccatca   28440
atatttgttt ttcttttaat ctggaacaac aggaaccaat tttatttctt cattcatata   28500
acagctattc tttagtttct cttttcaga ccaaacataa aatgagggag aatatccaaa   28560
ccataagtga aaataaatat cattactgtg agctttagtt tgctaaggat aatgacctcc   28620
agccctatcc atgtccctgc aaagggcatg attttgttct ttttatggct gcatagcatt   28680
cccatggtgt atgtatacca catttctctt atccagtcta tcactaatgg gcatttaggt   28740
tgattctatg tctttgctat accgaagagt gctagaggga gaggatcagg aaaaataact   28800
aatgggtact aggcttaata cctgggtgat gaaataatat gtacaacaaa accccatgac   28860
acaagtttac ctgtgtaaca aacctgcaca tgtaaccctg aactttgaaa aagtatata   28920 tatgcacaca catatatatg catacatata tatgtgtgta tatatatgca tatatgtgtg   28980
tgtgtatata taaaaaaaaa tatatatata tatatatata tataattacc tcattttcc   29040 agaaccaact tccagatgcc ctaccacatt ggttcttatt ctctgaacat tcgagacttt   29100
gtcagtgtct tccttaaaat atgcttccaa taactaaata caccaagaca gatgtgtgac   29160
tagtgtcaca cataacaaaa taaagcagga agtcttctga aaaatacaaa taatgtaaat   29220
tggtgggaga cagtgtttta taagggaag agcagagaga ggcaggcaga tatgtgatgt   29280
gaatcaaata gtttaaccta tccaggcttt attttcctta agtataaaac acagtcttta   29340
ctagatgatc tttcattgct actaaatgat ttttccgatt cctgtatgta ccataatcca   29400
cccattgccc aagcccacaa gctagaagtc aaccgcattt accacatttg atcatctctc   29460
```

```
aaaggactat gcagtcatct aatagacttt accacatcca ttcttgacct tcaagaatct    29520
actccccaga aagaacaaac atgtttttta aaaatgtaaa tgagactaca ttattctctg    29580
gcttaattat ccagtagatt cccatatcac ttcaataaaa tttaagcact ttatcatgac    29640
ctataaaaca ctctaaaatc tagtccctgc ttacctctcc aagctcaccc ccaaccattc    29700
tttcccttgt gttctgactg cagcccatcc aacccaagac cttgggattt ttgcctggaa    29760 acttgttttcc ctcatctcct cacactgacc ctcttttact atgtcttagc ccaaatgcgt    29820
tatcaaaata atcataatga cctgttagta ctctattccg ttaccctatt ttattttgtt    29880
catagccttt atcaatgttt aagattattt atctatttgt ttgcttgctt tgatccttttt   29940 ccttctctgg aatcttatac tcctgtgagc aggcacctta ggtcctgttc atcactttat    30000
ccccagcagt tcagataagg ctcagcacac agatgctcag taaatatttg tggaagggat    30060
aaatgaatga tattttatgt gtattacagt tctaaaattc aatagttttg tattaaaatat   30120 cagttctaat atggcattta tatgatttta tctttcaaaa cattagcaat agattatatt    30180
taaatgataa aagaaaacta taactgcagc caagtattct caggattgta tttctcttat    30240
attagcctaa atgcaattaa tctagctcat atactttggg cagcttatat atattctgtt    30300
aatttctaac cttttccagg tataaaaatc cacatcaatg gactgttagt tttggaacaa    30360
aaatcaaccc tcccttaatg aaaagaaatg tcagaagatt tattatccat gagaagtacc    30420
gctctgcagc aagagagtac gacattgctg ttgtgcaggt ctcttccaga gtcaccttttt   30480 cggatgacat acgccagatt tgtttgccag aagcctctgc atccttccaa ccaaatttga    30540
ctgtccacat cacaggattt ggagcacttt actatggtgg tgggtatctc aggatagcta    30600
acagagcgct aagccctgtc taaggcaatg tgatttcatc tccatcaata ttatcctgac    30660
agccatttcc acacagtctg gttggattag ttagggttct tactttgtgt gacagaaatt    30720
caattcacat taaccagtgc agaataaaaa acaaagaaac aaaaacttcc acaaatttgg    30780
ctcatgtaat ttggaagtca aaaaagtgta gtaagtttca cttcagacac aggggtttat    30840
atgatgtcat ctggctctgt gtctctgaat ttgaattttt tgcccctttct tttctctatg    30900 ttggcttcat tcagagggat gctagcttca cctagtgtca gaggtggcta acaacacctc    30960
aacacatcat cctcaacaaa gaaaaaatac atagaaagga atatttattt cttttctttg    31020
ccagaattca cattaatttc tattgttcca gctgtgtcta ggaggactca gattgagtgg    31080
ctaactcaaa tattctttat gcctatgtag caaaatttgc ttcagtactg aagaagctaa    31140
tttaagtgtg atggtgaata agaatagtgt agagataaat tgtcaaacta tttgtcccct    31200
ctaaaagtat tcaacttgat atactaactt agtcttgtaa gaaataatga tgatttagtt    31260
actgaatgtt ctaggcaatc ttagtgagac acgctctgga ttctaacatg tggtccaggt    31320
acatatgtat aacaaagcta gaaagtttct ttaaacactgg gcttgagaaa atgcaaaagg    31380
gctttctgag aatgactaaa tctatttgca ggattctata caatttattt acatacaaga    31440
aattataaag aataagcttt tgattctcag tctaccatta aggaactagg aataaccttt    31500
cactcacata ggcaggaatc ggttttaggg tctctagatt ttttccagat gtcccatgtg    31560
gttttgtttt atcttataca gagtgagaca tgcattgctt tctttaaggt tgtattacca    31620
atcacagaaa atattaccta tggtttatta attctagtag atccagtgct gctgtaagcc    31680
tgacacctcc ctaggtctgc actctcttgg atggattttc tctgaagata gggcttgcat    31740
tctctgcttc atagtggtgg gaaagacatc acaaatcccc tttggcttgg tgggaaaaat    31800
```

-continued

```
cactttcagg agtttgagac tggcacagaa acatacctgt cataatgcgc tgtgagtggc    31860
aacagaatct gacacttata gagcactcca ccctacttga acacggcctc tcttggtgag    31920
tgacccacag gtgcttttaa tctattaaat agattaaatt aacctatcat tcttaatctg    31980
ttaagtacat taatagatta aaagcagcca ttcgttactc accaagagag gctatattca    32040
agtctgtaaa gcaaaccttt agaagttttt taaaattgaa attgtacaaa gtatattctc    32100
tgatcataat ggaatctaac tagacatcag taacagaaag ataacataaa aatccccaaa    32160
tgcttaccaa ttaaaaaaca tatgtaaata aagagaatat ctcgaagaaa tttgtaaaaa    32220
caaatagaac taaatgaaaa caaaatatat aaatatatg ccagatgctg ctaaaatagt     32280
gtagaaaggg aaatttatag aaaatgcata ttataaggaa agatatcaaa tcaataatta    32340
agttctcact tcaagaaact agaaaaataa aaaataaacc taaacaaac ataaggaagg     32400 aaataataag aataagaata gaaatgaata aaattaaaaa taaactatag aaaattgata    32460
aataaaaagc tgattatttg ataaaatcaa tattttgcta gaaatgtcat taagcatttt    32520
tacagaagat gagatatagc tcagggatgt ccagaattta tgggctatgc ttttcatgac    32580
ttggaataca ttttaccaac cagtttagtt tgctgaagaa gttgtggatt tgcactgtca    32640
cctacttaca atacttagat tgtcagtttc accttactct tctcaccatt attttatttt    32700 tattttatt tttattttta ttttgaaaca gagtctcgct ctgtctccca ggctggagtg    32760
cagtggcgtg atctcggctc actgcaaact ccgcctcccg ggttcacgcc attctcctgc    32820
ctcagcctcc cgagtagctg ggactgcagg cgcccaccac catgcccggc taattgtttt    32880
gtagttttag taaagaaggg gtttcaccgt gttagccagg atggttttga tctcctgacc    32940
tcgtgatcca cctgcctcgg cctcccaaag tgctgggatt acaggcgtga gccaccgcgc    33000
gccaggccat gaatgttttt aattgatgat atagtaggca atataaatgt gtgtgtgtgt    33060
gtgtgtgtgt gtgtataata tatataaacc aattgtattc aaataacaga ataatttgaa    33120
aaatctctta gcatatttct gagttacaca cttaaatctt ccgagcactt ttaaatatgt    33180
gtttacaaac atttcttcag aaataaatct tggaaatcgt cttctaaaga aactggtgta    33240
ttagggtttt ttcaaatgta cttagttttt tttttaattg atgtataaaa ttgcatgtac    33300
ttaccatgtg caacataatg tgttgaagta tagtatatgt acactgtgag tgttaaatct    33360
agttaactaa gaagcgtctt atttttacata attatcattt ttgtggcaag aacacttaat    33420
atctactctt gtagcgtttc tcaagaatac gatatatcaa cagtaggcaa ccagaagctg    33480
ggggtcttta caggggaagg agttagggag atgctggtca acaaattcat atttgcagtt    33540
aggaagaaaa agttcaagag atctctcatc catcatggtg actatagctg atgatatatc    33600
gtattcttgt attagttttt tataaatgtg taacaaataa tcacaaacag ttaaaacagc    33660
actcatttat ttttatctca ctgttttcat gagtcagacg ttcagacaca gcttagttga    33720
gtcctcttct caggtctcca ccaaactgta atcaaggtgt cagctgggt tgtggccaca     33780 tctgtggctc ctttgaaggt ctcctcaagg tttgctggca gaattccttt actcgcagct    33840
gtagaatgca tgccagcttg ctgctttaac tcttttaggaa agtgtctcaa ctccagcaag    33900
gctcgccctt tttgaaatgg ctcagctgat taggtcaggc ccacctttga taatctcctt    33960
ttgatgaatt caaagtcaaa ctcattagag gtcttaatcg catctgtaaa attccctcat    34020
cttggccata taacataacc taatcatgag aatggcatcc ctcatattca cagatcctgc    34080
ccatatttgg gaggagggga atcacacagg aatcttgggg actatcctag aattctgcca    34140
accatggggt catggtttcc caatcaatat atggtttggt ataaagaatc cctgaatgct    34200
```

```
tgtgctattc ttagttttct acgtagcctg ccataataat ggtttctaaa actcagaacc    34260
tagcttacag tctgcagcca ccaacttgta atacattgga agtgaaatca ttgccgttta    34320
atgcatttat atatatatga tgtataatat atgtatattt cacatatatc ttatatatgt    34380
gaaagctcat cataaacttt aaataataaa ataaatgtac atagtattat aggcatttta    34440
tcaagccaat ggagaaaacc atctaggcat gcagagtttc tgggaacaat ctggaaccca    34500
caaataaaag ctttacaaaa gataaaaggc cttcctgaaa tatataagct gattattttt    34560
aaggttagat tttaccagga aaagaatcc aaatggcttt cttgctttga aagttttta    34620 taaaaatgtg attggacaat aattatcgtt agatgtgcca gatttaacca gaaattcttt    34680
tttctagaaa ctgcttatat taacttcatt ctgtattgac aattttacca tgaaaaaat    34740 attaggaaag tcttctcact tcactctagc caaagatgct gattgtaaat actagaataa    34800
ctctattttt ccttaagggg aatcccaaaa tgatctccga gaagccagag tgaaaatcat    34860
aagtgacgat gtctgcaagc aaccacaggt gtatggcaat gatataaaac ctggaatgtt    34920
ctgtgccgga tatatggaag gaatttatga tgcctgcagg gtaagttgga gggattttt    34980 tatattacta actcaaaaat ttgtatctgg cttagaatat attatatgtt ctttacataa    35040
ggacaaaaca tagatatcat gtcagctcaa aaaagttaca aatgcaaatt tcacagcaca    35100
aaatactttt aaatgttta ttaagataaa tgaagtaaga gtttctctga tgctatcaaa    35160
caaacaaaat tagaatttct taaccagaaa tccaaagatt aataaagcag tttatttct    35220 caagcggctc acattcaaga aagaaaataa tcataaacag agaagtataa agtgatgtta    35280
tgaataatat aatgaaaagc aaatattttt cttgaaggaa acatttttgg aacaagtatc    35340
agagagatga gacgtaaata aggcctgaag aataaataac atccaatttc agaataagaa    35400
aataatgtta tagaaaagac aaaaagcata gccaaaatta tgaaggtgtg aaattacaat    35460
tcatatctga gggaactcca agtaattggt tgggtctcag catgaggagg atgagaagag    35520
aaacaagtag ataaccatga gaaggtggat taggccatgt tgtgattcca tgggccctcc    35580
ccagtgccct catctgcctt ctaacatgga tgttttccag cgaaggtacg tttcttcctg    35640
gagacacttg cttttaaca tgagatactt tagaactcta aggaggccac tctatgtgga    35700
aatgatggaa tggtattgat atcaggtggc agaaagtcct gtccagagtc ccacaaactg    35760
taccacatgt gcgacctcta tcagaaaagg agcagggacc tatgtgacat agaggctggg    35820
caaaagcagg atctggtcca cagccagcct cggttgctaa taatgtggag ggaggcaggc    35880
agaatttagg gattccaaca aaaggtccat accacgggga acaggtggaa ggtgcaggag    35940
tcttggagca gacaggaccg gggaattcag gtgaaccatg acattactga aaagccttag    36000
gagggattgg tggtcataga gatgcttcac tggattgggg agcagaggta aacttgctgc    36060
ctaactgtgc aaagtaagtg ataaaacaag gctttagtca tagaaaaata cagtaagtta    36120
tcagggcagc ggttcaggta caaggatcca agacaggaat acagtgattg taattgggc    36180 acatggtgag gggcctagtc tgatacaaca gaagtgcaag caccaccaac acctcgtctt    36240
tctccataag tctttctctc cagagccctc atgacctaat cacctcttct taagtcccat    36300
ctctcaacac tattgtattg gagattaagt ttccccaacc tatgaactct tgggctcaca    36360
ttcaaaccat agcaccaccc agcacaaaag cacagagctt ccaatctggt ttctagctcc    36420 atacccctaga accaaacagt aagaatcacc tctggaaatg tagcaataat ataatcataa    36480
tttttaaaat ccagtggaag gattggaaga taaaatcaag gaaatctctc agaaagaaca    36540
```

```
acaacaacaa aaaagacaca gaggagaaaa ataatcagaa aaattaagaa aactagagga    36600
taagctcagg agatccaaca ccaaatgaat aggagctctg aaaacataaa acgcgagtgt    36660
acaatataaa aaaaaataaa gaatgctcct agttctgaag cttacatgca tcctattgaa    36720
gaaaaggtcc aagtagtgct gggcacaata aatgaagtac ttctttccaa gacataccat    36780
cataaagggt cagaagccag ggataaggag aacaatctta aaactttgaa ggaagaacca    36840
tcagaactac atagaactcc tcaacagtaa ctctagaagg tagacgatgg tggaaaacac    36900
attcaaattt caagggaag attatttcaa cctagattcc tacccatgct aactaaatat    36960
caactgtgag ggtggaatta agaagtttag acaagcaatg actgaaaaaa atgtacttct    37020
gatacccctac ttcttaggaa actacttgag agggtacctc agcaaaatga gggaataaat    37080
caagaaagtg gaagacgtaa gacctgaaac tgttagtcca acactaaaga gtggtatcag    37140
ataatcccaa caccatagct ctgcaccagg cttaaagtaa ccagctcgaa tttgagcaga    37200
agtaagaaaa gattgtgtgt atgtgtatgt gtatgtgtgt atgtgtgtgt gtgtgtgtgt    37260
gtgtgttgat atggtggaac agcttcagag gaagtaaaag aactaacaag ctatctgatg    37320
tccttgaaca ttagtaaaca ttattgtgag gtgttggtag atcttttgga gcattcagca    37380
tttaccaggt acatagaaaa ctatccacat gaaaaaaaga gttgtgttat taattctagg    37440
aaagcaaaaa aagatttctg taatccaaat atgttacttg actcttcaat taataaaatt    37500
tacacactgg tactaaatgt aggctgttaa tttaaccaaa aatagagatg ctataatgta    37560
aagatgtggt gtggaaaagt tgcaaagaag ttgtaaaaca actaaatccc taactacgta    37620
agagaaaata aatatttact gtctaaacct agaagctgta atttgagcat attatctagt    37680
gataaggagt tagatactat aagaaatcat taaacaagca tgaagtggct acctcttgga    37740
gaacagcttg cgtgaggtaa catgggacat aactgctttt caagcctctt catgttttt    37800
cgttttgcc ttttttaact aagtgctgtt tactctaaca aaataaattt tatttttaa    37860
atgtgaaagt tgaaccttaa ggctctttgt aatattaaaa tccatgtctc aattaattat    37920
tctgtgttga tagtctatac atgtactgtc tagtaacaaa atatgtgatt catcaaaata    37980
tcttaaataa tgagctttat gtttagctaa ttttctttct tttttcttat gtttttattt    38040
ttagggtgat tctgggggac ctttagtcac aagggatctg aaagatacgt ggtatctcat    38100
tggaattgta agctggggag ataactgtgg tcaaaaggac aagcctggag tctacacaca    38160
agtgacttat taccgaaaact ggattgcttc aaaaacaggc atctaattca cgataaaagt    38220
taaacaaga aagctgtatg caggtcatat atgcatgaga attcaactat ttagtgggtg    38280
tagtacaaca aagtgatatt aaattactgg atctagtaac atgaaacaca caacgtaagt    38340
tatttagaat cactttaatc aaccaataat ccttagccaa tttataaggg acttttattt    38400
gtaaagtaat ggatctggct tgaaaaatac ggtagagata cttagctctt taaatcacga    38460
atgttgaagt accagtgaga ctcaatacat attttttgaag atagtccatg ggattttttag   38520
aatgtcgttg tcaagggtct ccttttaact gagaaacttt ttgaactcac aaagtgttca    38580
agaaccctt gtataattcc ctacatttct ctcgagctca caaatacttt ttttttcttt    38640
tccttattca atcagatttt ccaaagtacc tttccaccat aagaaatgaa ttttctactt    38700
ctacacccat ttgagagaca ccaataaaag aaagtcatat gtaggaaaca aagtctgata    38760
gtaaaacaag ccagagatct tctaactttt tttagttata aaacctctaa ttttttggtga    38820
cttttctaca cacacacaca cata                                            38844
```

<210> SEQ ID NO 4
<211> LENGTH: 407
<212> TYPE: PRT
<213> ORGANISM: Homo sapien

<400> SEQUENCE: 4

```
Glu Pro Trp Val Ile Gly Leu Val Ile Phe Ile Ser Leu Ile Val Leu
 1               5                  10                  15

Ala Val Cys Ile Gly Leu Thr Val His Tyr Val Arg Tyr Asn Gln Lys
            20                  25                  30

Lys Thr Tyr Asn Tyr Tyr Ser Thr Leu Ser Phe Thr Thr Asp Lys Leu
        35                  40                  45

Tyr Ala Glu Phe Gly Arg Glu Ala Ser Asn Asn Phe Thr Glu Met Ser
    50                  55                  60

Gln Arg Leu Glu Ser Met Val Lys Asn Ala Phe Tyr Lys Ser Pro Leu
65                  70                  75                  80

Arg Glu Glu Phe Val Lys Ser Gln Val Ile Lys Phe Ser Gln Gln Lys
                85                  90                  95

His Gly Val Leu Ala His Met Leu Leu Ile Cys Arg Phe His Ser Thr
            100                 105                 110

Glu Asp Pro Glu Thr Val Asp Lys Ile Val Gln Leu Val Leu His Glu
        115                 120                 125

Lys Leu Gln Asp Ala Val Gly Pro Pro Lys Val Asp Pro His Ser Val
    130                 135                 140

Lys Ile Lys Lys Ile Asn Lys Thr Glu Thr Asp Ser Tyr Leu Asn His
145                 150                 155                 160

Cys Cys Gly Thr Arg Arg Ser Lys Thr Leu Gly Gln Ser Leu Arg Ile
                165                 170                 175

Val Gly Gly Thr Glu Val Glu Glu Gly Glu Trp Pro Trp Gln Ala Ser
            180                 185                 190

Leu Gln Trp Asp Gly Ser His Arg Cys Gly Ala Thr Leu Ile Asn Ala
        195                 200                 205

Thr Trp Leu Val Ser Ala Ala His Cys Phe Thr Thr Tyr Lys Asn Pro
    210                 215                 220

Ala Arg Trp Thr Ala Ser Phe Gly Val Thr Ile Lys Pro Ser Lys Met
225                 230                 235                 240

Lys Arg Gly Leu Arg Arg Ile Ile Val His Glu Lys Tyr Lys His Pro
                245                 250                 255

Ser His Asp Tyr Asp Ile Ser Leu Ala Glu Leu Ser Ser Pro Val Pro
            260                 265                 270

Tyr Thr Asn Ala Val His Arg Val Cys Leu Pro Asp Ala Ser Tyr Glu
        275                 280                 285

Phe Gln Pro Gly Asp Val Met Phe Val Thr Gly Phe Gly Ala Leu Lys
    290                 295                 300

Asn Asp Gly Tyr Ser Gln Asn His Leu Arg Gln Ala Gln Val Thr Leu
305                 310                 315                 320

Ile Asp Ala Thr Thr Cys Asn Glu Pro Gln Ala Tyr Asn Asp Ala Ile
                325                 330                 335

Thr Pro Arg Met Leu Cys Ala Gly Ser Leu Glu Gly Lys Thr Asp Ala
            340                 345                 350

Cys Gln Gly Asp Ser Gly Gly Pro Leu Val Ser Asp Ala Arg Asp
        355                 360                 365

Ile Trp Tyr Leu Ala Gly Ile Val Ser Trp Gly Asp Glu Cys Ala Lys
    370                 375                 380
```

-continued

```
Pro Asn Lys Pro Gly Val Tyr Thr Arg Val Thr Ala Leu Arg Asp Trp
385                 390                 395                 400

Ile Thr Ser Lys Thr Gly Ile
                405
```

ISOLATED HUMAN PROTEASE PROTEINS, NUCLEIC ACID MOLECULES ENCODING HUMAN PROTEASE PROTEINS, AND USES THEREOF

RELATED APPLICATIONS

The present application is a divisional of U.S. application Ser. No. 09/734,675, filed on Dec. 13, 2000 and issued on Apr. 2, 2002 as U.S. Pat. No. 6,365,391, which claims priority to U.S. Provisional Application No. 60/235,557, filed on Sep. 27, 2000.

FIELD OF THE INVENTION

The present invention is in the field of protease proteins that are related to the serine protease subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases (Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner AP Press, NY 1998). Also, for a review of the various uses of proteases as drug targets, see: Weber M, Emerging treatments for hypertension: potential role for vasopeptidase inhibition; Am J Hypertens Nov. 12, 1999 (11 Pt 2):139S–147S; Kentsch M, Otter W, Novel neurohormonal modulators in cardiovascular disorders. The therapeutic potential of endopeptidase inhibitors, Drugs R D Apr. 1, 1999 (4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci Jun. 30 1999; 878:61–72; McKerrow J H, Engel J C, Caffrey C R, Cysteine protease inhibitors as chemotherapy for parasitic infections, Bioorg Med Chem Apr. 7, 1999 (4):639–44; Rice K D, Tanaka R D, Katz B A, Numerof R P, Moore W R, Inhibitors of tryptase for the treatment of mast cell-mediated diseases, Curr Pharm Des 1998 Oct. 4, 1998 (5):381–96; Materson B J, Will angiotensin converting enzyme genotype, receptor mutation identification, and other miracles of molecular biology permit reduction of NNT Am J Hypertens Aug. 11, 1998 (8 Pt2):138–142S Serine Proteases The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence GDSGGP which contains the active site serine; and 3) an N-terminal IIGG sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal IIGG sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsin-like serine proteases have been isolated from patients with chronic airway diseases and may play a role in respiratory diseases and host defense systems on the mucous membranes of the respiratory system (see Yamaoka et al, *J. Biol. Chem.* 273: 11895–11901, 1998 and Yasuoka et al., *Am. J Resp. Cell Molec. Biol.* 16: 300–308, 1997). Therefore, novel human serine protease proteins, and encoding genes, may be useful for screening for, diagnosing, preventing, and/or treating disorders such as respiratory diseases. For example, serine protease genes/proteins may be useful in drug development, such as by serving as novel drug targets for respiratory disease, and SNPs in serine protease genes may be useful markers for diagnostic kits for respiratory diseases.

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy CO et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha -2-macroglobulin are not measurable with antibody-based assays (Ohlsson K, Acta Gastroenterol Belg 1988; 51:3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton AC (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence HEXXH, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium*; Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from Aspergillus sojae (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from Aspergillus oryzae has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been devided into several distinct families based primarily on activity and structure: 1) water nucleophile; water bound by single zinc ion ligated to two His (within the motif HEXXH) and Glu, His or Asp; 2) water nucleophile; water bound by single zinc ion ligated to His, Glu (within the motif HXXE) and His; 3) water nucleophile; water bound by single zinc ion ligated to His, Asp and His; 4) Water nucleophile; water bound by single zinc ion ligated to two His (within the motif HXXEH) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (Homo sapiens), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diamninopimelate peptidase I (*Bacillus sphaericus*), vanY D-Ala-D-Ala carboxypeptidase (*Enterococcus faecium*), endolysin (bacteriophage A 118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (Pseudomonas sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgAl-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), IAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ssl (*Sulfolobus solfataricus*), FtsH endopeptidase (*Escherichia coli*), glutamyl aminopeptidase (*Lactococcus lactis*), cytophagalysin (Cytophaga sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol.Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Bums, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic Protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bilobed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO-NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), baciliform virus putative protease (rice tungro baciliform virus), aspergillopepsin II (*Aspergillus niger*), thermopsin (*Sulfolobus acidocaldarius*), nodavirus endopeptidase (flock house virus), pseudomonapepsin (Pseudomonas sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bsl endopeptidase (*Zea mays*), retrotransposon peptidase (Drosophila buzzatii), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis* omega virus), presenilin 1 (*Homo sapiens*).

Proteases and Cancer

Proteases are critical elements at several stages in the progression of metastatic cancer. In this process, the proteolytic degradation of structural protein in the basal membrane allows for expansion of a tumor in the primary site, evasion from this site as well as homing and invasion in distant, secondary sites. Also, tumor induced angiogenesis is required for tumor growth and is dependent on proteolytic tissue remodeling. Transfection experiments with various types of proteases have shown that the matrix metalloproteases play a dominant role in these processes in particular gelatinases A and B (MMP-2 and MMP-9, respectively). For an overview of this field see Mullins, et al., Biochim. Biophys. Acta 695, 177, 1983; Ray, et al., Eur. Respir. J. 7, 2062, 1994; Birkedal-Hansen, et al., Crit. Rev. Oral Biol. Med. 4, 197, 1993.

Furthermore, it was demonstrated that inhibition of degradation of extracellular matrix by the native matrix metalloprotease inhibitor TIMP-2 (a protein) arrests cancer growth (DeClerck, et al., Cancer Res. 52, 701, 1992) and that TIMP-2 inhibits tumor-induced angiogenesis in experimental systems (Moses, et al. Science 248, 1408, 1990). For a review, see DeClerck, et al., Ann. N. Y. Acad. Sci. 732, 222, 1994. It was further demonstrated that the synthetic matrix metalloprotease inhibitor batimastat when given intraperitoneally inhibits human colon tumor growth and spread in an orthotopic model in nude mice (Wang, et al. Cancer Res. 54, 4726, 1994) and prolongs the survival of mice bearing human ovarian carcinoma xenografts (Davies, et. al., Cancer Res. 53, 2087, 1993). The use of this and related compounds has been described in Brown, et al., WO-9321942 A2.

There are several patents and patent applications claiming the use of metalloproteinase inhibitors for the retardation of metastatic cancer, promoting tumor regression, inhibiting cancer cell proliferation, slowing or preventing cartilage loss associated with osteoarthritis or for treatment of other diseases as noted above (e.g. Levy, et al., WO-9519965 A1; Beckett, et al., WO-9519956 A1; Beckett, et al., WO-9519957 A1; Beckett, et al., WO-9519961 A1; Brown, et al., WO-9321942 A2; Crimmin, et al., WO-9421625 A1; Dickens, et al., U.S. Pat. No. 4,599,361; Hughes, et al., U.S. Pat. No. 5,190,937; Broadhurst, et al., EP 574758 A1; Broadhurst, et al., EP 276436; and Myers, et al., EP 520573 A1.

Protease proteins, particularly members of the serine subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the serine subfamily.

SUMMARY OF THE INVENTION

The present invention is based in part on the identification of amino acid sequences of human protease peptides and proteins that are related to the serine protease subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in humans in testis, placenta, fetal lung, fetal kidney, fetal heart, fetal brain, bone marrow, and in cancers.

DESCRIPTION OF THE FIGURE SHEETS

FIG. 1 provides the nucleotide sequence of a cDNA molecule that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in testis, placenta, fetal lung, fetal kidney, fetal heart, fetal brain, bone marrow, and in cancers.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. As indicated in FIG. 3, SNPs, including insertion/deletion polymorphisms ("indels"), were identified at 69 different nucleotide positions in and around the gene encoding the serine protease protein of the present invention.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the serine protease subfamily. Utilizing these sequences, additional genomic sequences were assembled and transcript and/or cDNA sequences were isolated and characterized. Based on this analysis, the present invention provides amino acid sequences of human protease peptides and proteins that are related to the serine protease subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the serine protease subfamily and the expression pattern observed. Experimental data as provided in FIG. 1 indicates expression in humans in testis, placenta, fetal lung, fetal kidney, fetal heart, fetal brain, bone marrow, and in cancers. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine family or subfamily of protease proteins.

Specific Embodiments

Peptide Molecules

The present invention provides nucleic acid sequences that encode protein molecules that have been identified as being members of the protease family of proteins and are related to the serine protease subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in humans in testis, placenta, fetal lung, fetal kidney, fetal heart, fetal brain, bone marrow, and in cancers. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al, *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol* 215:403–10 (1990)). BLAST nucleotide searches can be performed with the NBLAST program, score =100, wordlength =12 to obtain nucleotide sequences homologous to the nucleic acid molecules of the invention. BLAST protein searches can be performed with the XBLAST program, score =50, wordlength =3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. The gene provided by the present invention is located on a genome component that has been mapped to human chromosome 4 (as indicated in FIG. 3), which is supported by multiple lines of evidence, such as STS and BAC map data.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. The gene provided by the present invention is located on a genome component that has been mapped to human chromosome 4 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been identified in the gene encoding the protease protein of the present invention. SNPs, including indels (indicated by a "–"), were identified at 69 different nucleotide positions. Non-synonymous cSNPs were identified at position 30496. The changes in the amino acid sequence caused by these SNPs is indicated in FIG. 3 and can readily be determined using the universal genetic code and the protein sequence provided in FIG. 2 as a reference. SNPs outside the ORF and in introns may affect control/regulatory elements.

Paralogs of a protease peptide can readily be identified as having some degree of significant sequence homology/identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. The gene provided by the present invention is located on a genome component that has been mapped to human chromosome 4 (as indicated in FIG. 3), which is supported by multiple lines of evidence, such as STS and BAC map data.

FIG. 3 provides information on SNPs that have been identified in the gene encoding the protease protein of the present invention. SNPs, including indels (indicated by a "–"), were identified at 69 different nucleotide positions. Non-synonymous cSNPs were identified at position 30496. The changes in the amino acid sequence caused by these SNPs is indicated in FIG. 3 and can readily be determined using the universal genetic code and the protein sequence provided in FIG. 2 as a reference. SNPs outside the ORF and in introns may affect control/regulatory elements.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutarnate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol* 182: 626–646 (1990)) and Rattan et al. (*Ann. N. Y Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow. A large percentage of pharmaceutical agents are being developed that modulate the activity of protease proteins, particularly members of the serine subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in testis, placenta, fetal lung, fetal kidney, fetal heart, fetal brain, bone marrow, and in cancers. Such uses can readily be determined using the information provided herein, that which is known in the art, and routine experimentation.

The proteins of the present invention (including variants and fragments that may have been disclosed prior to the present invention) are useful for biological assays related to proteases that are related to members of the serine subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in humans in testis, placenta, fetal lung, fetal kidney, fetal heart, fetal brain, bone marrow, and in cancers. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in humans in testis, placenta, fetal lung, fetal kidney, fetal heart, fetal brain, bone marrow, and in cancers. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in testis, placenta, fetal lung, fetal kidney, fetal heart, fetal brain, bone marrow, and in cancers. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol* 23(10–11):983–985 (1996)), and Linder, M. W. (Clin. *Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in testis, placenta, fetal lung, fetal kidney, fetal heart, fetal brain, bone marrow, and in cancers. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in testis, placenta, fetal lung, fetal kidney, fetal heart, fetal brain, bone marrow, and in cancers. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in testis, placenta, fetal lung, fetal kidney, fetal heart, fetal brain, bone marrow, and in cancers. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in testis, placenta, fetal lung, fetal kidney, fetal heart, fetal brain, bone marrow, and in cancers. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As indicated in FIG. 3, SNPs, including insertion/deletion polymorphisms ("indels"), were identified at 69 different nucleotide positions in and around the gene encoding the transporter protein of the present invention.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene provided by the present invention is located on a genome component that has been mapped to human chromosome 4 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in humans in testis, placenta, fetal lung, fetal kidney, fetal heart, fetal brain, bone marrow, and in cancers. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in humans in testis, placenta, fetal lung, fetal kidney, fetal heart, fetal brain, bone marrow, and in cancers.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been identified in the gene encoding the protease protein of the present invention. SNPs, including indels (indicated by a "–") were identified at 69 different nucleotide positions. Non-synonymous cSNPs were identified at position 30496. The changes in the amino acid sequence caused by these SNPs is indicated in FIG. 3 and can readily be determined using the universal genetic code and the protein sequence provided in FIG. 2 as a reference. SNPs outside the ORF and in introns may affect control/regulatory elements. The gene provided by the present invention is located on a genome component that has been mapped to human chromosome 4 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., Appl. *Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been identified in the gene encoding the protease protein of the present invention. SNPs, including indels (indicated by a "–"), were identified at 69 different nucleotide positions. Non-synonymous cSNPs were identified at position 30496. The changes in the amino acid sequence caused by these SNPs is indicated in FIG. 3 and can readily be determined using the universal genetic code and the protein sequence provided in FIG. 2 as a reference. SNPs outside the ORF and in introns may affect control/regulatory elements.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in humans in testis, placenta, fetal lung, fetal kidney, fetal heart, fetal brain, bone marrow, and in cancers. Specifically, a virtual northern blot shows expression in cancers. In addition, PCR-based tissue screening panels indicate expression in testis, placenta, fetal lung, fetal kidney, fetal heart, fetal brain, and bone marrow. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in US Pat. No. 5,837,832, Chee et al., PCT application W095/11995 (Chee et al.), Lockhart, D. J. et al. (1996; *Nat. Biotech.* 14: 1675–1680) and Schena, M. et al. (1996; *Proc. Natl. Acad. Sci.* 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application W095/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been identified in the gene encoding the protease protein of the present invention. SNPs, including indels (indicated by a "–"), were identified at 69 different nucleotide positions. Non-synonymous cSNPs were identified at position 30496. The changes in the amino acid sequence caused by these SNPs is indicated in FIG. 3 and can readily be determined using the universal genetic code and the protein sequence provided in FIG. 2 as a reference. SNPs outside the ORF and in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual*. 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as *Drosophila*, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al, *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSecl (Baldari, et al., *EMBO J.* 6:229–234 (1987)), pMFa (Kujan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al, *EMBO J*. 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et a. *PNAS* 89:6232–6236 (1992). Another example of a recombinase system is the FLP recombinase system of *S cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an nucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide having an amino acid sequence consisting of SEQ ID NO:2.

2. An isolated polypeptide having an amino acid sequence comprising SEQ ID NO:2.

3. A composition comprising the polypeptide of claim 1 and a carrier.

4. A composition comprising the polypeptide of claim 2 and a carrier.

* * * * *